United States Patent
Greenhouse et al.

(10) Patent No.: US 6,852,726 B2
(45) Date of Patent: Feb. 8, 2005

(54) SUBSTITUTED INDOLES AS ALPHA-1 AGONISTS

(75) Inventors: Robert Greenhouse, Newark, CA (US); Saul Jaime-Figueroa, Fremont, CA (US); Lubica Raptova, Sunnyvale, CA (US)

(73) Assignee: Syntex LLC, Palo Alto, CA (US)

( * ) Notice: Subject to any disclaimer, the term of this patent is extended or adjusted under 35 U.S.C. 154(b) by 6 days.

(21) Appl. No.: 10/355,588

(22) Filed: Jan. 31, 2003

(65) Prior Publication Data

US 2003/0220319 A1 Nov. 27, 2003

Related U.S. Application Data

(60) Provisional application No. 60/353,508, filed on Feb. 1, 2002, and provisional application No. 60/418,492, filed on Oct. 15, 2002.

(51) Int. Cl.[7] ............... C07D 403/06; A61K 31/4178; A61K 31/506; A61P 11/02; A61P 13/02
(52) U.S. Cl. ............... 514/256; 514/402; 544/333; 548/311.4; 548/312.1
(58) Field of Search ............... 514/256, 402; 544/333; 548/311.4, 312.1, 312

(56) References Cited

U.S. PATENT DOCUMENTS

| | | | |
|---|---|---|---|
| 3,404,156 A | 10/1968 | Archer | |
| 3,689,655 A | 9/1972 | Rosenberg et al. | |
| 4,654,360 A | 3/1987 | Greenhouse et al. | |
| 5,095,031 A | 3/1992 | Brooks et al. | |
| 5,459,150 A | 10/1995 | Brooks et al. | |
| 5,952,362 A | 9/1999 | Cournoyer et al. | |
| 6,175,013 B1 | 1/2001 | Hipskind et al. | |
| 2001/0039255 A1 | 11/2001 | Brioni et al. | |

FOREIGN PATENT DOCUMENTS

| | | |
|---|---|---|
| EP | 0 538 000 A1 | 4/1993 |
| EP | 0 699 665 A1 | 3/1996 |
| EP | 0 924 209 A1 | 6/1999 |
| WO | WO 92/03132 | 3/1992 |
| WO | WO 94/14434 A1 | 7/1994 |
| WO | WO 97/00860 | 1/1997 |
| WO | WO 97/09308 | 3/1997 |

OTHER PUBLICATIONS

Civantos Calzada B, Aleixandre de Artinano A., Pharmacol Res. Sep. 2001;44(3):195–208.*
Roehrborn CG., Urology. Feb. 2002;59(2 Suppl 1):3–6.*
West, Anthony R., Solid State Chemistry and its Applications, Wiley, New York, 1988, pp. 358 & 365.*
Michael J. Bishop, Kevin A. Barvian, Judd Berman, Eric C. Bigham, Deanna T. Garrison, Michael J. Gobel, Stephen J. Hodson, Paul E. Irving, James A. Liacos, Frank Navas et al., Bioorganic & Medicinal Chemistry Letters, vol. 12, Issue 3, Feb. 11, 2002,.*
Dictionary of Organic Compounds, vol. 1, no author listed, Chapman and Hall, New York, 1982, pp. 1035, entry C–00549.*

* cited by examiner

Primary Examiner—Thomas C. McKenzie
(74) Attorney, Agent, or Firm—Robert C. Hall

(57) ABSTRACT

This invention relates to compounds which are alpha-1 receptor agonists, preferably alpha-1A/L receptor agonists, and which are represented by Formula I:

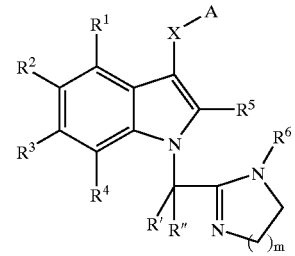

Formula I wherein X is $-S(O)_n-$ or $-C(O)-$, A is $C_{1-6}$alkyl, aryl, heteroaryl, hydroxyalkyl, or $-(CH_2)_p-NR^aR^b$, and the other substituents are as defined in the specification; or individual isomers, racemic or non-racemic mixtures of isomers, or pharmaceutically acceptable salts or solvates thereof. The invention further relates to pharmaceutical compositions containing such compounds, methods for their use as therapeutic agents, and methods of preparation thereof.

40 Claims, No Drawings

SUBSTITUTED INDOLES AS ALPHA-1 AGONISTS

CROSS-REFERENCE

This application claims the benefit of priority of U.S. Provisional Patent Applications Ser. No. 60/353,508, filed Feb. 1, 2002, and Ser. No. 60/418,492, filed Oct. 15, 2002, which are incorporated herein by reference in their entirety.

FIELD OF THE INVENTION

This invention relates to substituted indoles, especially certain 1-(imidazolin-2-ylmethyl)-3-alkylsulfonylindole derivatives, which are alpha-1 adrenergic agonists, preferably alpha-1A/L adrenergic agonists, and associated pharmaceutical compositions, methods for use as therapeutic agents, and methods of preparation thereof.

BACKGROUND OF THE INVENTION

Alpha-1 adrenergic receptors (interchangeably named alpha-1 adrenoceptors) are G-protein coupled transmembrane receptors that mediate various actions of the sympathetic nervous system through the binding of the catecholamines, epinephrine and norepinephrine (NE). Currently, several subtypes of the alpha-1 adrenergic receptors are known to exist for which the genes have been cloned: alpha-1A (previously known as alpha-1C), alpha-1B and alpha-1D. Recently the existence of a low affinity alpha-1 adrenoceptor for prazosin named alpha-1L, in human prostate has been determined. However, the gene for the alpha-1L adrenergic receptor subtype has yet to be cloned. The alpha-1 adrenoceptor plays a part in the sympathetic maintenance of smooth muscle tone and alpha-1 adrenergic agonists are known to increase muscle tone in the lower urinary tract necessary for urine storage and urine emptying thus making adrenergic receptors important targets for drug development in urinary dysfunction (Testa, R., *Eur. J. Pharmacol.*, 1993, 249, 307–315. Pharmacological studies resulting in the subdivision of alpha-1 adrenergic receptors have let to the suggestion that development of subtype-selective compounds may allow improved treatment with a lower incidence of side effects, and Tanaguchi et al., *Eur. J. Pharmacol*, 1996, 318, 117–122, have reported that compounds with selectivity for the alpha-1A receptor and to a lessen extent to the alpha-1L receptor over the alpha-1B and alpha-1D subtypes have selectivity for urethral over vascular tissue.

Certain alpha-1A agonists are known and are indicated to be useful in treating various disease states including urinary incontinence, nasal congestion, sexual dysfunction such as ejaculation disorders and priapism, and CNS disorders such as depression, anxiety, dementia, senility, Alzheimer's, deficiencies in attentiveness and cognition, and eating disorders such as obesity, bulimia, and anorexia, see for example U.S. Pat. No. 5,952,362 (Cournoyer et al.) which discloses a variety of alpha-1A/L agonists including some 2-imidazoline, 2-oxazoline, 2-thiazoline and 4-imidazole derivatives, but not any 1-(imidazolin-2-ylmethyl)-3-alkylsulfonylindole derivatives like those of the present invention.

Urinary incontinence is a condition defined as the involuntary loss of urine to such an extent as to become a hygienic or social concern to the patient. Stress urinary incontinence (SUI) occurs when the internal sphincter does not close completely. The primary symptom is minor leakage from activities, such as coughing, sneezing, laughing, running, lifting, or even standing, that apply pressure to a full bladder. Leakage stops when the activity stops. SUI is most common in women between the ages of 25 and 50, and many regularly exercising women have some degree of SUI.

The present methods to treat SUI include physiotherapy and surgery. Treatment with pharmaceuticals is limited to the use of non-selective adrenergic agonists. Only a limited number of pharmaceutical agents have been employed, with varying success, to treat stress incontinence.

Phenylpropanolamine, pseudoephrine and midodrine are considered first-line therapy for mild to moderate stress incontinence (Wein, supra; Lundberg (editor), *JAMA* 1989, 261(18):2685–2690). These agents are believed to work both by direct activation of alpha-1 adrenoceptors and indirectly by displacement of endogenous norepinephrine from sympathetic neurons following uptake into the nerve terminal (Andersson and Sjogren, *Progress in Neurobiology*, 1982, 71–89). Activation of alpha-1 adrenoceptors located on the smooth muscle cells of the proximal urethra and bladder neck (Sourander, *Gerontology* 1990, 36:19–26; Wein, supra) evokes contraction and an increase in urethral closure pressure.

The utility of phenylpropanolamine, pseudoephrine, and midodrine is limited by a lack of selectivity among the alpha-1 adrenoceptor subtypes and by the indirect action of these agents (i.e. activation of alpha-1, alpha-2, and beta-adrenoceptors in the central nervous system and periphery). As a result, any desired therapeutic effect of these agents may be accompanied by undesirable side effects such as an increase in blood pressure. The increase in blood pressure is dose-dependent and therefore limits the ability to achieve therapeutically effective circulating concentrations of these agents (Andersson and Sjogren, supra). Furthermore, in some patients these agents produce insomnia, anxiety and dizziness as a result of their central nervous system stimulant actions (Andersson and Sjogren, supra, Wein, supra).

Due to side effects and/or limited efficacy associated with the current available medicaments, there is an unmet medical need for useful compounds. A compound having the desired alpha-1A/L adrenergic agonist profile is desirable.

SUMMARY OF THE INVENTION

The invention provides compounds of the formula I:

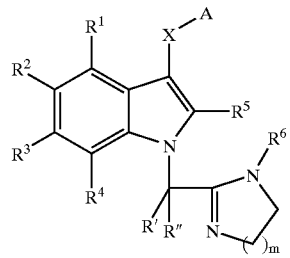

Formula I wherein:

X is —S(O)$_n$— or —C(O)—;

A is C$_{1-6}$alkyl, aryl, heteroaryl, hydroxyalkyl, or —(CH$_2$)$_p$—NR$^a$R$^b$;

R$^1$, R$^2$, R$^3$, and R$^4$ each independently is hydrogen, halogen, haloalkyl, C$_{1-6}$alkyl, hydroxy, C$_{1-6}$alkoxy, C$_{1-6}$alkylthio, C$_{1-6}$alkylsulfinyl, C$_{1-6}$alkylsulfonyl, C$_{1-6}$alkylsulfonylamino, C$_{1-6}$alkylaminosulfonyl, cyano, nitro, —NR$^a$R$^b$, phenyl, benzyl or benzyloxy, wherein said phenyl rings are optionally substituted with C$_{1-6}$alkyl, halogen, cyano, nitro, haloalkyl, or C$_{1-6}$alkoxy;

$R^5$ is hydrogen, $C_{1-6}$alkyl, $C_{1-6}$alkoxy, $C_{1-6}$alkoxyalkyl, $C_{1-6}$alkylthio, $C_{1-6}$alkylsulfinyl, $C_{1-6}$alkylsulfonyl, hydroxyalkyl, hydroxyalkylamino, halogen, haloalkyl, cyano, —$NR^aR^b$, —$NR^c$—$C_{1-6}$alkylene-$NR^aR^b$, or $R^5$ and A together form a $C_2$–$C_3$ alkylene radical;

$R^6$ is hydrogen or $C_{1-6}$alkyl;

R' and R" each independently is hydrogen or alkyl;

$R^a$, $R^b$, and $R^c$ each independently is hydrogen, alkyl, hydroxyalkyl, alkoxyalkyl, aminoalkyl, haloalkyl, alkenyl, alkynyl, cycloalkyl, cycloalkylalkyl, alkylthioalkyl, heterocyclyl, heterocyclylalkyl, aryl, arylalkyl, heteroaryl, heteroarylalkyl, or arylsulfonyl, or $R^a$ and $R^b$ together with the nitrogen they are attached to may also form a 5- to 7-membered non-aromatic heterocyclic ring optionally incorporating an additional ring heteroatom chosen from N, O, or S;

m is 1 or 2;

n is 0, 1 or 2 with the proviso that when n is 0, $R^5$ is not —$NR^aR^b$; and p is 0, 1 or 2;

or individual isomers, racemic or non-racemic mixtures of isomers, prodrugs, or pharmaceutically acceptable salts or solvates thereof.

Those skilled in the art will recognize that stereoisomers exist in some compounds of Formula I. Accordingly, the present invention includes all possible stereoisomers, and geometric isomers and includes not only racemic compounds but also the optically active compounds as well. Additionally when tautomers of the compounds of Formula I are possible, the present invention is intended to include all tautomeric forms of the compounds.

In a preferred embodiment, the invention further relates to pharmaceutical compositions containing a therapeutically effective amount of at least one compound of Formula I, or individual isomers, racemic or non-racemic mixtures of isomers, or pharmaceutically acceptable salts or solvates thereof, in admixture with at least one suitable carrier.

In another embodiment the method of treating a subject comprises administering to a subject having a disease state which is alleviated by treatment with an alpha-1A/L receptor agonist, a therapeutically effective amount of one or more compounds of Formula I.

In another embodiment, the method of treating a subject comprises administering to a subject having a disease state which is alleviated by treatment with an alpha-1A/L receptor agonist, a pharmaceutically effective amount of the pharmaceutical composition containing at least one compound of Formula I.

In a preferred embodiment, the subject has a disease state comprising urinary incontinence, nasal congestion, sexual dysfunction such as ejaculation disorders and priapism, and CNS disorders such as depression, anxiety, dementia, senility, Alzheimer's, deficiencies in attentiveness and cognition, and eating disorders such as obesity, bulimia, and anorexia.

In another embodiment the patient has a disease state selected from urge incontinence, stress incontinence, overflow incontinence and functional incontinence.

In another embodiment the patient has a disease comprising nasal congestion associated with allergies, colds, and other nasal disorders, as well as the sequelae of congestion of the mucous membranes (for example, sinusitis and otitis media). Another aspect of this invention involves methods for preventing or treating nasal congestion by administering a safe and effective amount of a subject compound to a mammal experiencing or at risk of experiencing nasal congestion. Such nasal congestion may be associated with human diseases or disorders which include, but are not limited to, seasonal allergic rhinitis, acute upper respiratory viral infections, sinusitis, perennial rhinitis, and vasomotor rhinitis. In addition, other disorders can be generally associated with mucous membrane congestion (for example, otitis media and sinusitis).

In still another preferred embodiment, the invention provides a process which comprises reacting a compound having a general Formula f

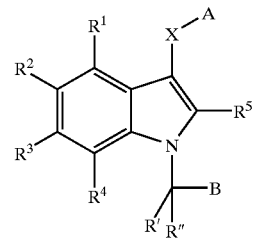

Formula f wherein B is a cyano or a carboxylic acid or ester group, and $R^1$, $R^2$, $R^3$, $R^4$, $R^5$, $R^6$, R', R", n, X, and A are as defined herein,
with an appropriate alkylene diamine to provide a compound of the general Formula I

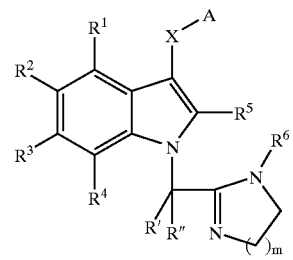

Formula I wherein $R^1$, $R^2$, $R^3$, $R^4$, $R^5$, $R^6$, R', R", n, m, and A are as defined herein.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear, branched or cyclic saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, cyclopropyl, isopropyl, isobutyl, sec-butyl, tert-butyl, pentyl, n-hexyl, octyl, dodecyl, and the like.

"Lower alkyl" means the monovalent linear or branched saturated hydrocarbon radical, consisting solely of carbon and hydrogen atoms, having from one to six carbon atoms inclusive, unless otherwise indicated. Examples of lower alkyl radicals include, but are not limited to, methyl, ethyl, n-propyl, isopropyl, sec-butyl, tert-butyl, n-butyl, n-pentyl, n-hexyl, and the like.

"Alkylene" means a linear saturated divalent hydrocarbon radical of one to six carbon atoms or a branched saturated divalent hydrocarbon radical of three to six carbon atoms. $C_2$–$C_3$ alkylenes include, by way of example, ethylene, 2,2-dimethylethylene, propylene, 2-methylpropylene, and the like.

"Alkoxy" means the radical —O—R, wherein R is a lower alkyl radical as defined herein. Examples of alkoxy radicals include, but are not limited to, methoxy, ethoxy, isopropoxy, and the like.

"Alkoxyalkyl" means a radical —$R^aR^b$ wherein $R^a$ is alkylene as defined herein and $R^b$ is alkoxy as defined herein.

"Alkenyl" means a linear monovalent hydrocarbon radical of two to six carbon atoms or a branched monovalent hydrocarbon radical of three to six carbon atoms, containing at least one double bond, e.g., ethenyl, propenyl, allyl and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl and the like.

"Aryl" means the monovalent cyclic aromatic hydrocarbon radical consisting of one or more fused rings in which at least one ring is aromatic in nature, which can optionally be substituted with hydroxy, cyano, lower alkyl, lower alkoxy, alkylthio, halo, haloalkyl, hydroxyalkyl, nitro, alkoxycarbonyl, amino, alkylamino, dialkylamino, aminocarbonyl, carbonylamino, aminosulfonyl, sulfonylamino, nitro, and/or alkylsulphonyl, unless otherwise indicated. Examples of aryl radicals include, but are not limited to, phenyl, naphthyl, biphenyl, indanyl, anthraquinolyl, and the like.

"Arylalkyl" and "aralkyl, which may be used interchangeably, mean a radical —$R^aR^b$ wherein $R^a$ is alkylene as defined herein and $R^b$ is aryl as defined herein.

"Heteroaryl" means the monovalent aromatic carbocyclic radical having one or more rings incorporating one, two, or three heteroatoms within the ring (chosen from nitrogen, oxygen, or sulfur) which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or alkylsulfonyl, unless otherwise indicated. Examples of heteroaryl radicals include, but are not limited to, imidazoyl, oxazoyl, thiazoyl, pyrazinyl, thiophenyl, furanyl, pyranyl, pyridinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, quinolinyl, isoquinolinyl, quinuclidinyl, naphtyridinyl, and the like.

"Arylsulfonyl" means a radical —S(O)$_2$R where R is an aryl group as defined herein.

"Heteroarylalkyl" means a radical —$R^aR^b$ wherein $R^a$ is alkylene as defined herein and $R^b$ is heteroaryl as defined herein.

"Cycloalkyl" means a saturated monovalent cyclic hydrocarbon radical of three to seven ring carbons. The cycloalkyl may be optionally substituted independently with one, two, or three substituents selected from alkyl, optionally substituted phenyl, or —C(O)R (where R is hydrogen, alkyl, haloalkyl, amino, acylamino, mono-alkylamino, di-alkylamino, hydroxy, alkoxy, or optionally substituted phenyl). More specifically, the term cycloalkyl includes, for example, cyclopropyl, cyclohexyl, phenylcyclohexyl, 4-carboxycyclohexyl, 2-carboxamidocyclohexyl, 2-dimethylaminocarbonyl-cyclohexyl, and the like.

"Cycloalkylalkyl" means a radical —$R^aR^b$ where $R^a$ is an alkylene group and $R^b$ is a cycloalkyl group as defined herein, e.g., cyclopropylmethyl, cyclopropylethyl, cyclobutylmethyl, cyclobutylethyl, cyclopentylmethyl, cyclopentylethyl, cyclohexylpropyl, 3-cyclohexyl-2-methylpropyl, and the like.

"Halogen" or "halo" means the radical fluoro, bromo, chloro, and/or iodo.

"Haloalkyl" means the lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Alkylthio" means the radical —SR, wherein R is a lower alkyl radical as defined herein. Examples of alkylthio radicals include, but are not limited to, methylthio, butylthio, and the like.

"Alkylthioalkyl" means a radical —$R^aR^b$ wherein $R^a$ is alkylene as defined herein and $R^b$ is alkylthio as defined herein.

"Alkylamino" means the radical —NHR, wherein R is a lower alkyl radical as defined herein. Examples of alkylamino radicals include, but are not limited to, methylamino, (1-ethyl)amino, and the like.

"Dialkylamino" means the radical —NR'R", wherein R' and R" are each independently lower alkyl radicals as defined herein. Examples of dialkylamino radicals include, but are not limited to, dimethylamino, methylethylamino, diethylamino, di(1-methylethyl)amino, and the like.

"Aminoalkyl" means a radical —$R^aR^b$ wherein $R^a$ is alkylene as defined herein and $R^b$ is —NH$_2$ or alkylamino or dialkylamino as defined herein.

"Alkylaminosulfonyl" means the radical —S(O)$_2$NR'R", wherein R' is lower alkyl as defined herein, and R" is hydrogen or lower alkyl as defined herein. Examples of alkylaminosulfonyl include, but are not limited to methylaminosulfonyl, dimethylaminosulfonyl, and the like.

"Alkylsulfonylamino" means the radical —NS(O)$_2$R', wherein R" is lower alkyl as defined herein. Examples of alkylsulfonylamino include, but are not limited to methylsulfonylamino, ethylsulfonylamino, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl.

"Hydroxyalkylamino means a radical —NRR' wherein R is hydrogen, alkyl or hydroxyalkyl, and R' is hydroxyalkyl as defined herein.

"Heterocyclyl" means a monovalent saturated moiety, consisting of one to three rings, incorporating one, two, or three heteroatoms (chosen from nitrogen, oxygen or sulfur). The heterocyclyl ring may be optionally substituted as defined herein. Examples of heterocyclyl moieties include, but are not limited to, piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a radical —$R^aR^b$ wherein $R^a$ is alkylene as defined herein and $R^b$ is heterocyclyl as defined herein.

"2-imidazoline" means the moiety designated by the structure:

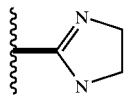

It is to be understood that the double bond in the 2-imidazoline may assume other resonance forms. The term 2-imidazoline includes all such resonance forms.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral compound" means a compound with one or more chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When chiral centers are present, the stereoisomers may be characterized by the absolute configuration (R or S) of the chiral centers. Absolute configuration refers to the arrangement in space of the substituents attached to a chiral center. The substituents attached to a chiral center under consideration are ranked in accordance with the *Sequence Rule* of Cahn, Ingold and Prelog. (Cahn et al. *Angew. Chem. Inter.*, 1966, Edit., 5, 385; errata 511; Cahn et al. *Angew. Chem.*, 1966, 78, 413; Cahn and Ingold, *J. Chem. Soc.* (London), 1951, 612; Cahn et al., *Experientia*, 1956, 12, 81; Cahn, J., *Chem. Educ.*, 1964, 41, 116).

"Tautomers" refers to compounds whose structures differ markedly in arrangement of atoms, but which exist in easy and rapid equilibrium. Compounds of Formula I contain groups that may exist in tautomeric equilibrium. It is to be understood that compounds of Formula I may be depicted as different tautomers.

It should also be understood that when compounds have tautomeric forms, all tautomeric forms are intended to be within the scope of the invention, and the naming of the compounds does not exclude any tautomer form.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Leaving group" means the group with the meaning conventionally associated with it in synthetic organic chemistry, i.e., an atom or group displaceable under alkylating conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Inert organic solvent" or "inert solvent" means the solvent inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" or "pro-drug" means a pharmacologically inactive form of a compound which must be metabolized in vivo, e.g., by biological fluids or enzymes, by a subject after administration into a pharmacologically active form of the compound in order to produce the desired pharmacological effect. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, sulfhydryl, carboxy or carbonyl group respectively. Examples of prodrugs include, but are not limited to, esters (e.g. acetate, dialkylaminoacetates, formates, phosphates, sulfates and benzoate derivatives) and carbamates of hydroxy functional groups (e.g. N,N-dimethyl-carbonyl), esters of carboxyl functional groups (e.g. ethyl esters, morpholinoethanol esters), N-acyl derivatives (e.g. N-acetyl), N-Mannich bases, Schiff bases and enaminones of amino functional groups, oximes, acetals, ketals, and enol esters of ketones and aldehyde functional groups in compounds of Formula I, and the like.

The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action*, by Richard B. Silverman, Academic Press, San Diego, 1992. Chapter 8: "Prodrugs and Drug delivery Systems" pp. 352–401; *Design of Prodrugs*, edited by H. Bundgaard, Elsevier Science, Amsterdam, 1985; *Design of Biopharmaceutical Properties through Prodrugs and Analogs*, Ed. by E. B. Roche, American Pharmaceutical Association, Washington, 1977; and *Drug Delivery Systems*, ed. by R. L. Juliano, Oxford Univ. Press, Oxford, 1980.

"Subject" means mammals and non-mammals. Mammals means any member of the Mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

"Pharmacological effect" as used herein encompasses effects produced in the subject that achieve the intended purpose of a therapy. For example, a pharmacological effect would be one that results in the prevention, alleviation or reduction of urinary incontinence in a treated subject.

"Disease state" means any disease, condition, symptom, or indication.

"Treating" or "treatment" of a disease state includes:

(1) preventing the disease state, i.e. causing the clinical symptoms of the disease state not to develop in a subject that may be exposed to or predisposed to the disease state, but does not yet experience or display symptoms of the disease state.

(2) inhibiting the disease state, i.e., arresting the development of the disease state or its clinical symptoms, or (3) relieving the disease state, i.e., causing temporary or permanent regression of the disease state or its clinical symptoms.

"$\alpha_1$-adrenergic receptors", "$\alpha_{1A}$-adrenergic receptors" (previously known as "$\alpha_{1C}$-adrenergic receptors"), or "$\alpha_{1L}$-adrenergic receptors", used interchangeably with "$\alpha_1$-adrenoceptors", "$\alpha_{1A}$-adrenoceptors" (previously known as "$\alpha_{1C}$-adrenoceptors receptors"), or "$\alpha_{1L}$-adrenoceptors", respectively, refers to a molecule conforming to the seven membrane-spanning G-protein receptors, which under physiologic conditions mediate various actions, for example, in the central and/or peripheral sympathetic nervous system through the binding of the catecholamines, epinephrine and norepinephrine.

"Agonist" means a molecule, such as a compound, a drug, an enzyme activator, or a hormone, that enhances the activity of another molecule or receptor site.

"Urinary Incontinence" is a condition characterized by the involuntary loss of urine, which is objectively demonstrable. It is both a social and hygienic problem. Stated simply, incontinence results from the failure of the bladder and/or the urethra to work properly, or when the coordination of their functions is defective. It is estimated that at least ten million Americans suffer from incontinence. While the prevalence of incontinence is two-fold higher in females, with the greatest incidence in postmenopausal women, it also affects males.

Urinary incontinence can be classified into four basic types: urge, stress, overflow and functional, and as used herein the term "urinary incontinence" encompasses all four types.

Urge incontinence (detrusor instability) is the involuntary loss of urine associated with a strong urge to void. This type of incontinence is the result of either an overactive or hypersensitive detrusor muscle. The patient with detrusor overactivity experiences inappropriate detrusor contractions and increases in intravesical pressure during bladder filling. Detrusor instability resulting from a hypersensitive detrusor (detrusor hyperreflexia) is most often associated with a neurological disorder.

Genuine stress incontinence (outlet incompetence) is the involuntary loss of urine occurring when increases in intra-abdominal pressure cause a rise in intravesical pressure which exceeds the resistance offered by urethral closure mechanisms. Stress incontinent episodes can result from normal activities such as laughing, coughing, sneezing, exercise, or, in severe stress incontinent patients, standing or walking. Physiologically, stress incontinence is often characterized by a descensus of the bladder neck and funneling of the bladder outlet. This type of incontinence is most common in multiparous women, as pregnancy and vaginal delivery can cause loss of the vesicourethral angle and damage to the external sphincter. Hormonal changes associated with menopause may exacerbate this condition.

Overflow incontinence is an involuntary loss of urine resulting from a weak detrusor or from the failure of the detrusor to transmit appropriate signals (sensory) when the bladder is full. Overflow incontinent episodes are characterized by frequent or continuous dribbling of urine and incomplete or unsuccessful voiding.

Functional incontinence, in contrast to the types of incontinence described above, is not defined by an underlying physiological dysfunction in the bladder or urethra. This type of incontinence includes the involuntary loss of urine resulting from such factors as decreased mobility, medications (e.g., diuretics, muscarinic agents, or alpha-1 adrenoceptor antagonists), or psychiatric problems such as depression or cognitive impairment.

"A method of treating or preventing incontinence" refers to the prevention of or relief from the symptoms of incontinence including involuntary voiding of feces or urine, and dribbling or leakage of feces or urine which may be due to one or more causes including, but not limited to, pathology altering sphincter control, loss of cognitive function, overdistention of the bladder, hyper-reflexia and/or involuntary urethral relaxation, weakness of the muscles associated with the bladder, or neurologic abnormalities.

Nomenclature

In general, the nomenclature used in this Application is based on AUTONOM™ v.4.0, a Beilstein Institute computerized system for the generation of IUPAC systematic nomenclature.

For example, a compound of Formula I wherein $S(O)_n$-A is alkylsulfonyl, m is 1, $R^2$ is fluoro, $R^1$, $R^3$, $R^4$, $R^5$, $R^6$, R' and R" are hydrogen, is named 1-(4,5-dihydro-1H-imidazol-2-ylmethyl)-5-fluoro-3-methanesulfonyl-1H-indole.

Preferred Compounds

Among compounds of the present invention set forth in the Summary of the Invention, certain compounds of Formula I, or individual isomers, racemic or non-racemic mixtures of isomers, or pharmaceutically acceptable salts or solvates thereof, are preferred:

A is preferably $C_{1-6}$alkyl, hydroxyalkyl, or —$NR^aR^b$;

$R^1$, $R^2$, $R^3$, and $R^4$ are each independently of each other in each occurrence, preferably selected from hydrogen, halogen, haloalkyl, $C_{1-6}$alkyl, hydroxy and $C_{1-6}$alkoxy, $C_{1-6}$alkylthio, $C_{1-6}$alkylsulfinyl, $C_{1-6}$alkylsulfonyl, $C_{1-6}$alkylsulfonylamino, $C_{1-6}$alkylaminosulfonyl, cyano, nitro, and —$NR^aR^b$; and more preferably from hydrogen and halogen;

$R^5$ is selected from hydrogen, $C_{1-6}$alkyl, $C_{1-6}$alkoxy, $C_{1-6}$alkylthio, $C_{1-6}$alkylsulfinyl, $C_{1-6}$alkylsulfonyl, halogen, haloalkyl, cyano, —$NR^aR^b$ and —$NR^c$—$C_{1-6}$alkyl-$NR^aR^b$; and more preferably is hydrogen or $C_{1-6}$alkyl;

$R^6$ is hydrogen or $C_{1-6}$alkyl; more preferably hydrogen;

R' and R" are each independently of each other in each occurrence hydrogen or alkyl; more preferably hydrogen;

$R^a$, $R^b$, and $R^c$ are each independently of each other in each occurrence hydrogen, alkyl, alkenyl, alkynyl, hydroxyalkyl or cycloalkylalkyl, or $R^a$ and $R^b$ may together may form a non-aromatic heterocyclic ring of 5- to 7-members that optionally includes one or more additional heteroatoms selected from O, N and S;

n is 0, 1 or 2 with the proviso that when n is 0, $R^5$ is not —$NR^aR^b$, more preferably n is 2;

m is 1 or 2, more preferably m is 1; and p is 0.

In certain embodiments, X is —$SO_2$— and A is $C_{1-6}$alkyl, and $R^5$ is hydrogen or methyl. In other embodiments, X is —C(O)— and A is —$(CH_2)_p$—$NR^aR^b$; more preferably A is —$NR^aR^b$, with $R^a$ and $R^b$ preferably being hydrogen, methyl or ethyl. $R^1$, $R^2$, $R^3$, and $R^4$ each independently may be hydrogen, halogen, haloalkyl, alkylsulfonyl or $C_{1-6}$alkyl. In some embodiments, one of $R^1$, $R^2$, $R^3$, and $R^4$ is halogen, haloalkyl, alkylsulfonyl or $C_{1-6}$alkyl, and the others are hydrogen.

A list of representative compounds is provided in Table 1. The structures in Table 1 in some instances are shown as hydrochloride or trifluoroacetic acid salts. The right-most column of Table 1 identifies the specific experimental examples (discussed below) associated with the preparation of the representative compounds.

TABLE 1

| Compound | Structure | Name (Autonom) | Example |
|---|---|---|---|
| 1 | 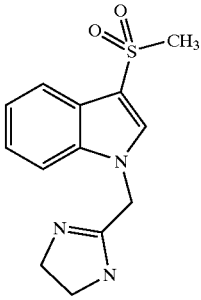 | 1-(4,5-Dihydro-1H-imidazol-2-ylmethyl)-3-methanesulfonyl-1H-indole | 3 |

TABLE 1-continued

| Compound | Structure | Name (Autonom) | Example |
|---|---|---|---|
| 2 | 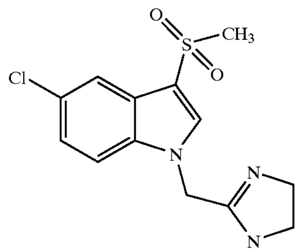 | 5-Chloro-1-(4,5-dihydro-1H-imidazol-2-ylmethyl)-3-methanesulfonyl-1H-indole | 3 |
| 3 | 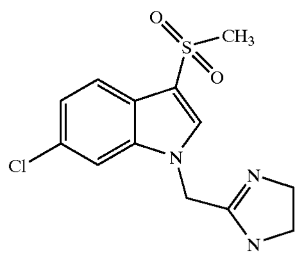 | 6-Chloro-1-(4,5-dihydro-1H-imidazol-2-ylmethyl)-3-methanesulfonyl-1H-indole | 3 |
| 4 | 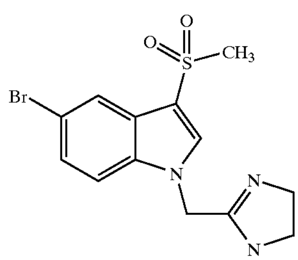 | 5-Bromo-1-(4,5-dihydro-1H-imidazol-2-ylmethyl)-3-methanesulfonyl-1H-indole | 2 |
| 5 | 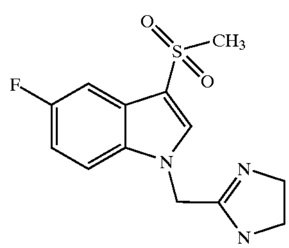 | 1-(4,5-Dihydro-1H-imidazol-2-ylmethyl)-5-fluoro-3-methanesulfonyl-1H-indole | 2 |
| 6 | 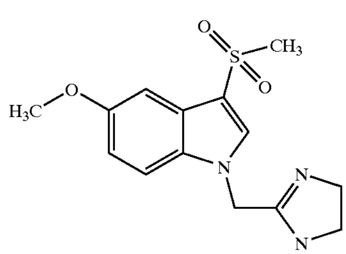 | 1-(4,5-Dihydro-1H-imidazol-2-ylmethyl)-3-methanesulfonyl-5-methoxy-1H-indole | 2 |
| 7 | 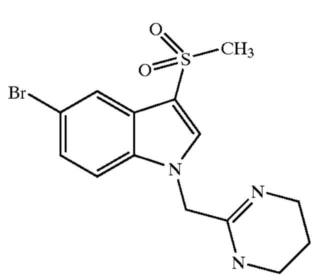 | 5-Bromo-3-methanesulfonyl-1-(1,4,5,6-tetrahydro-pyrimidin-2-ylmethyl)-1H-indole | 2 |

TABLE 1-continued

| Compound | Structure | Name (Autonom) | Example |
|---|---|---|---|
| 8 | 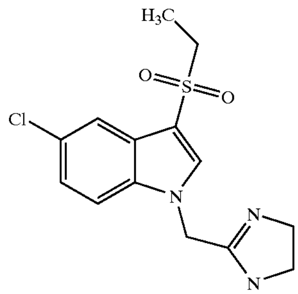 | 5-Chloro-1-(4,5-dihydro-1H-imidazol-2-ylmethyl)-3-ethanesulfonyl-1H-indole | 1 |
| 9 | 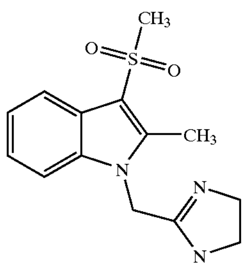 | 1-(4,5-Dihydro-1H-imidazol-2-ylmethyl)-3-methanesulfonyl-2-methyl-1H-indole | 1 |
| 10 | 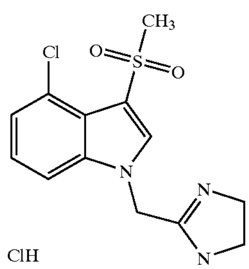 | 4-Chloro-1-(4,5-dihydro-1H-imidazol-2-ylmethyl)-3-methanesulfonyl-1H-indole; ClH | 1 |
| 11 | 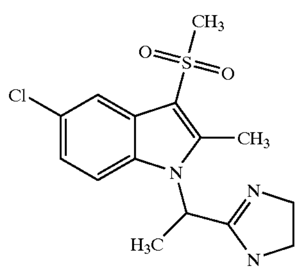 | 5-Chloro-1-[1-(4,5-dihydro-1H-imidazol-2-yl)-ethyl]-3-methanesulfonyl-2-methyl-1H-indole | 1 |
| 12 | 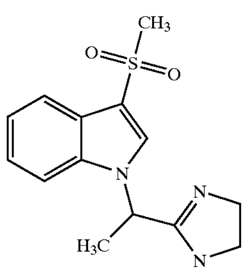 | 1-[1-(4,5-Dihydro-1H-imidazol-2-yl)-ethyl]-3-methanesulfonyl-2-methyl-1H-indole | 1 |

TABLE 1-continued

| Compound | Structure | Name (Autonom) | Example |
| --- | --- | --- | --- |
| 13 | 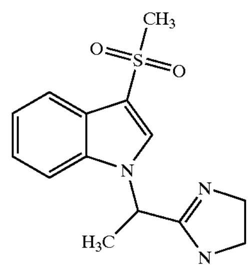 | 1-[1-(4,5-Dihydro-1H-imidazol-2-yl)-ethyl]-3-methanesulfonyl-1H-indole | 1 |
| 14 | 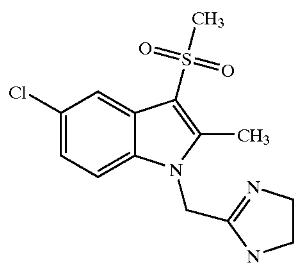 | 5-Chloro-1-(4,5-dihydro-1H-imidazol-2-ylmethyl)-3-methanesulfonyl-2-methyl-1H-indole | 1 |
| 15 | 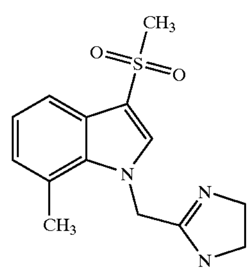 | 1-(4,5-Dihydro-1H-imidazol-2-ylmethyl)-3-methanesulfonyl-7-methyl-1H-indole | 2 |
| 16 | 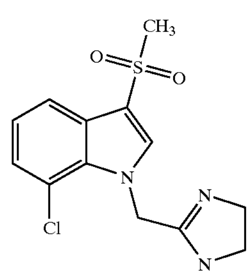 | 7-Chloro-1-(4,5-dihydro-1H-imidazol-2-ylmethyl)-3-methanesulfonyl-1H-indole | 2, 5 |
| 17 | 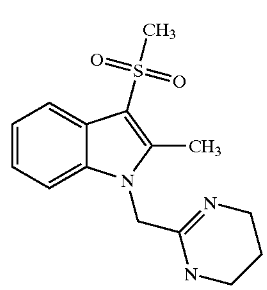 | 3-Methanesulfonyl-2-methyl-1-(1,4,5,6-tetrahydro-pyrimidin-2-ylmethyl)-1H-indole | 1 |

TABLE 1-continued

| Compound | Structure | Name (Autonom) | Example |
|---|---|---|---|
| 18 | 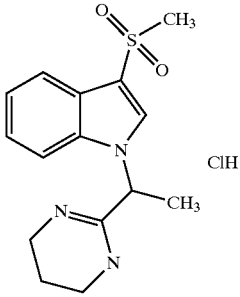 | 3-Methanesulfonyl-1-[1-(1,4,5,6-tetrahydro-pyrimidin-2-yl)-ethyl]-1H-indole | 1 |
| 19 | 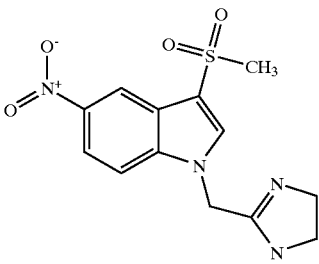 | 1-(4,5-Dihydro-1H-imidazol-2-ylmethyl)-3-methanesulfonyl-5-nitro-1H-indole | 2 |
| 20 | 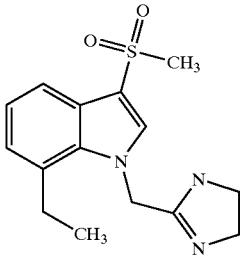 | 1-(4,5-Dihydro-1H-imidazol-2-ylmethyl)-7-ethyl-3-methanesulfonyl-1H-indole | 1 |
| 21 | 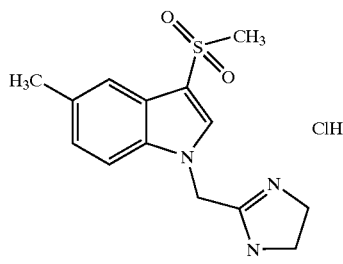 | 1-(4,5-Dihydro-1H-imidazol-2-ylmethyl)-3-methanesulfonyl-5-methyl-1H-indole | 1 |
| 22 | 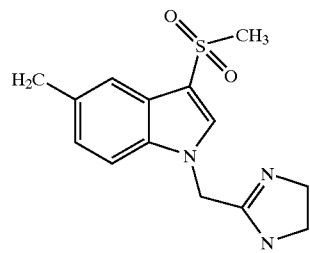 | 1-(4,5-Dihydro-1H-imidazol-2-ylmethyl)-3-methanesulfonyl-1H-indol-5-ylamine | 2 |

TABLE 1-continued

| Compound | Structure | Name (Autonom) | Example |
|---|---|---|---|
| 23 | 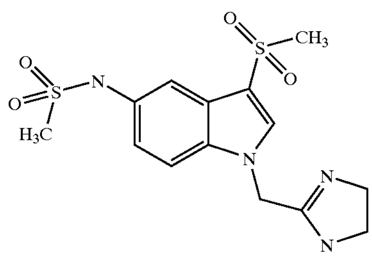 | N-1-(4,5-Dihydro-1H-imidazol-2-ylmethyl)-3-methanesulfonyl-1H-indol-5-yl]-methanesulfonamide | 2 |
| 24 | 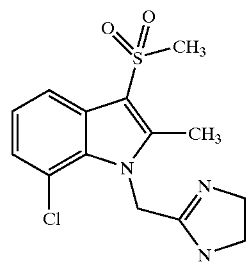 | 7-Chloro-1-(4,5-dihydro-1H-imidazol-2-ylmethyl)-3-methanesulfonyl-2-methyl-1H-indole | 4 |
| 25 | 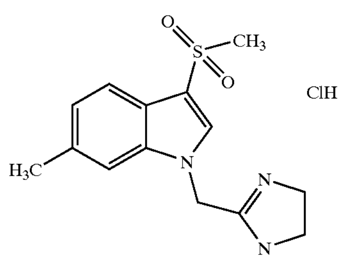 | 1-(4,5-Dihydro-1H-imidazol-2-ylmethyl)-3-methanesulfonyl-6-methyl-1H-indole | 1 |
| 26 | 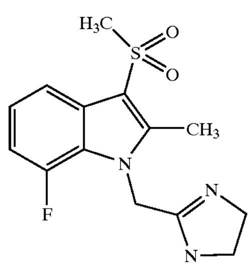 | 1-(4,5-Dihydro-1H-imidazol-2-ylmethyl)-7-fluoro-3-methanesulfonyl-2-methyl-1H-indole | 4 |
| 27 | 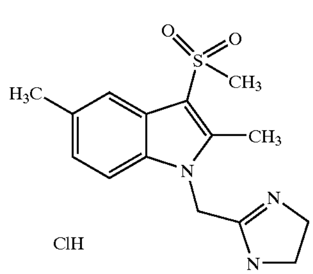 | 1-(4,5-Dihydro-1Hmidazol-2-ylmethyl)-3-methanesulfonyl-2,5-dimethyl-1H-indole | 1 |
| 28 | 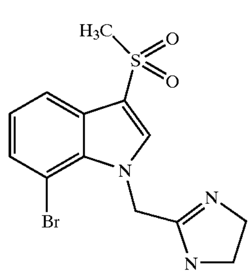 | 7-Bromo-1-(4,5-dihydro-1H-imidazol-2-ylmethyl)-3-methanesulfonyl-1H-indole | 2 |

TABLE 1-continued

| Compound | Structure | Name (Autonom) | Example |
|---|---|---|---|
| 29 | 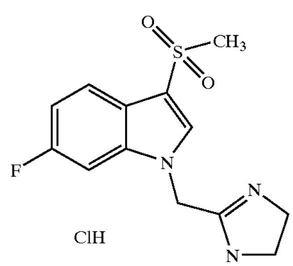 | 1-(4,5-Dihydro-1H-imidazol-2-ylmethyl)-6-fluoro-3-methanesulfonyl-1H-indole ClH | 1 |
| 30 | 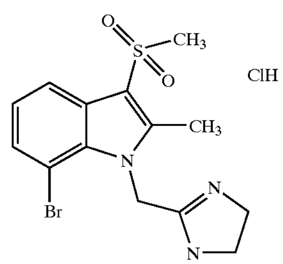 | 7-Bromo-1-(4,5-dihydro-1H-imidazol-2-ylmethyl)-3-methanesulfonyl-2-methyl-1H-indole ClH | 1 |
| 31 | 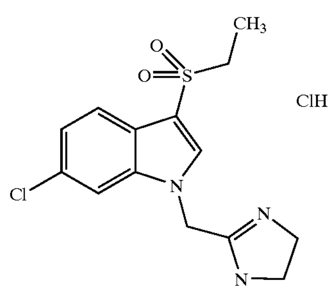 | 6-Chloro-1-(4,5-dihydro-1H-imidazol-2-ylmethyl)-3-ethanesulfonyl-1H-indole ClH | 1 |
| 32 | 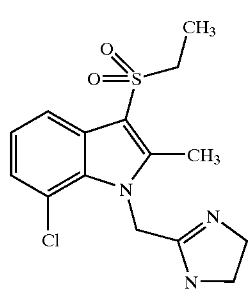 | 7-Chloro-1-(4,5-dihydro-1H-imidazol-2-ylmethyl)-3-ethanesulfonyl-2-methyl-1H-indole | 4 |
| 33 | 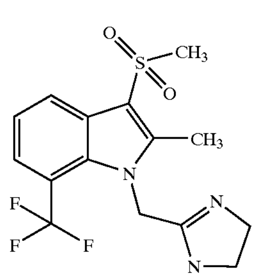 | 1-(4,5-Dihydro-1H-imidazol-2-ylmethyl)-3-methanesulfonyl-2-methyl-7-trifluoromethyl-1H-indole | 4 |

TABLE 1-continued

| Compound | Structure | Name (Autonom) | Example |
|---|---|---|---|
| 34 | 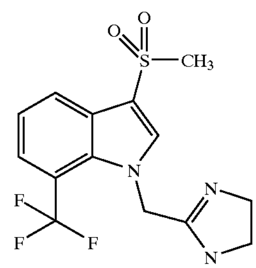 | 1-(4,5-Dihydro-1H-imidazol-2-ylmethyl)-3-methanesulfonyl-7-trifluoromethyl-1H-indole | 1 |
| 35 | 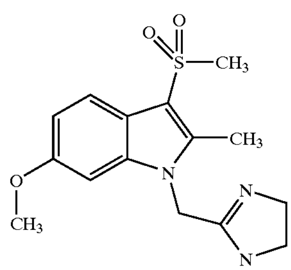 | 1-(4,5-Dihydro-1H-imidazol-2-ylmethyl)-3-methanesulfonyl-6-methoxy-2-methyl-1H-indole | 4 |
| 36 | ClH | 1-(4,5-Dihydro-1H-imidazol-2-ylmethyl)-3-methanesulfonyl-7-methoxy-1H-indole | 1 |
| 37 | 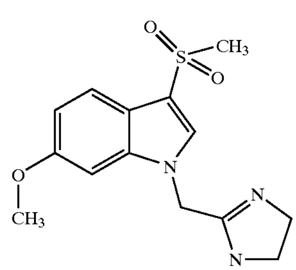 | 1-(4,5-Dihydro-1H-imidazol-2-ylmethyl)-3-methanesulfonyl-6-methoxy-1H-indole | 15 |
| 38 | 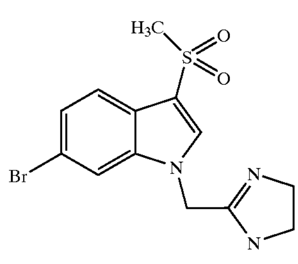 | 6-Bromo-1-(4,5-dihydro-1H-imidazol-2-ylmethyl)-3-methanesulfonyl-1H-indole | 1 |

TABLE 1-continued

| Compound | Structure | Name (Autonom) | Example |
|---|---|---|---|
| 39 | 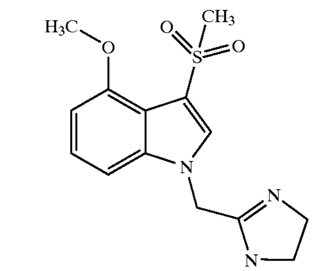 | 1-(4,5-Dihydro-1H-imidazol-2-ylmethyl)-3-methanesulfonyl-4-methoxy-1H-indole | 1 |
| 40 | 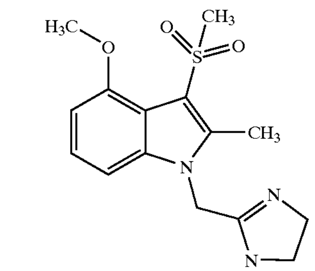 | 1-(4,5-Dihydro-1H-imidazol-2-ylmethyl)-3-methanesulfonyl-4-methoxy-2-methyl-1H-indole | 4 |
| 41 | 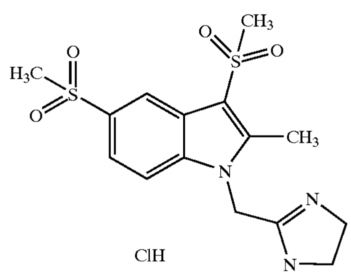 | 1-(4,5-Dihydro-1H-imidazol-2-ylmethyl)-3,5-bis-methanesulfonyl-2-methyl-1H-indole | 4 |
| 42 | 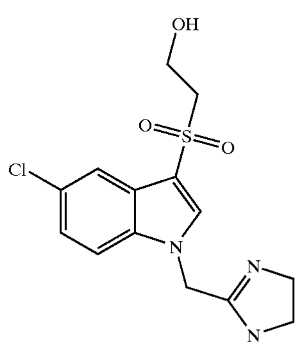 | 2-[5-Chloro-1-(4,5-dihydro-1H-imidazol-2-ylmethyl)-1H-indole-3-sulfonyl]-ethanol | 7 |
| 43 | 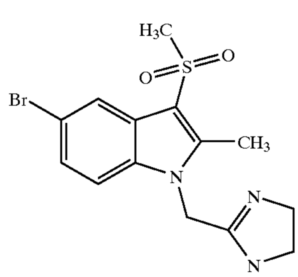 | 5-Bromo-1-(4,5-dihydro-1H-imidazol-2-ylmethyl)-3-methanesulfonyl-2-methyl-1H-indole | 1 |

TABLE 1-continued

| Compound | Structure | Name (Autonom) | Example |
|---|---|---|---|
| 44 | 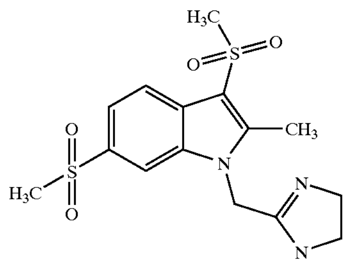 | 1-(4,5-Dihydro-1H-imidazol-2-ylmethyl)-3,6-bis-methanesulfonyl-2-methyl-1H-indole | 4 |
| 45 | 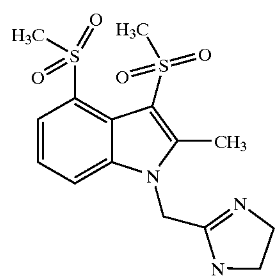 | 1-(4,5-Dihydro-1H-imidazol-2-ylmethyl)-3,4-bis-methanesulfonyl-2-methyl-1H-indole | 4 |
| 46 | 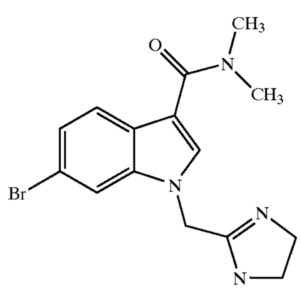 | 6-Bromo-1-(4,5-dihydro-1H-imidazol-2-ylmethyl)-1H-indole-3-carboxylic acid dimethylamide | 17 |
| 47 | 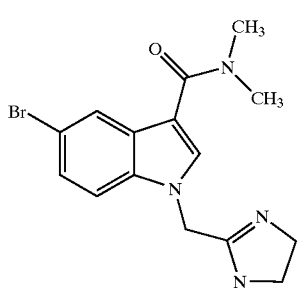 | 5-Bromo-1-(4,5-dihydro-1H-imidazol-2-ylmethyl)-1H-indole-3-carboxylic acid dimethylamide | 17 |
| 48 | 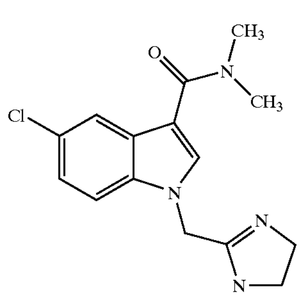 | 5-Chloro-1-(4,5-dihydro-1H-imidazol-2-ylmethyl)-1H-indole-3-carboxylic acid dimethylamide | 17 |

TABLE 1-continued

| Compound | Structure | Name (Autonom) | Example |
|---|---|---|---|
| 49 | 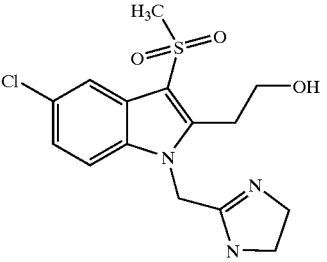 | 2-[5-Chloro-1-(4,5-dihydro-1H-imidazol-2-ylmethyl)-3-methanesulfonyl-1H-indol-2-yl]-ethanol | 10 |
| 50 | 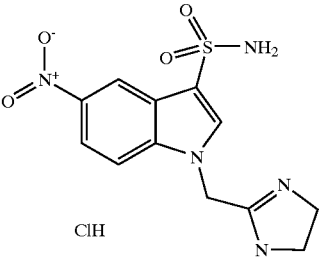 | 1-(4,5-Dihydro-1H-imidazol-2-ylmethyl)-5-nitro-1H-indole-3-sulfonic acid amide | 12 |
| 51 | 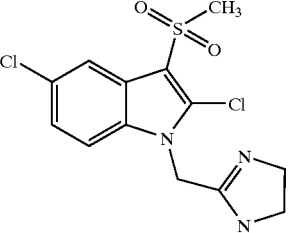 | 2,5-Dichloro-1-(4,5-dihydro-1H-imidazol-2-ylmethyl)-3-methanesulfonyl-1H-indole | 8 |
| 52 | 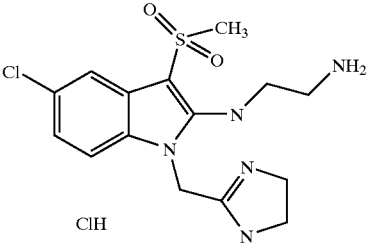 | N1-[5-Chloro-1-(4,5-dihydro-1H-imidazol-2-ylmethyl)-3-methanesulfonyl-1H-indol-2-yl]-ethane-1,2-diamine | 9 |
| 53 | 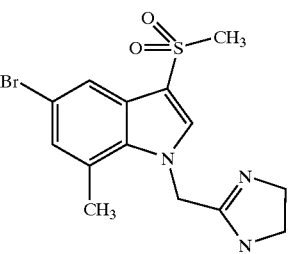 | 5-Bromo-1-(4,5-dihydro-1H-imidazol-2-ylmethyl)-3-methanesulfonyl-7-methyl-1H-indole | 1 |
| 54 | 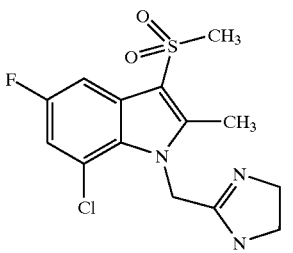 | 7-Chloro-1-(4,5-dihydro-1H-imidazol-2-ylmethyl)-5-fluoro-3-methanesulfonyl-2-methyl-1H-indole | 4 |

TABLE 1-continued

| Compound | Structure | Name (Autonom) | Example |
|---|---|---|---|
| 55 | 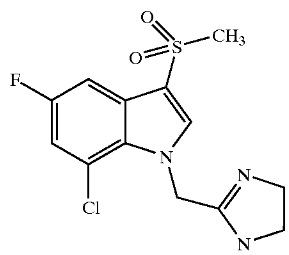 | 7-Chloro-1-(4,5-dihydro-1H-imidazol-2-ylmethyl)-5-fluoro-3-methanesulfonyl-1H-indole | 4 |
| 56 | 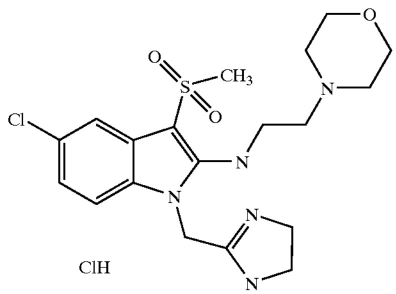 | [5-Chloro-1-(4,5-dihydro-1H-imidazol-2-ylmethyl)-3-methanesulfonyl-1H-indol-2-yl]-(2-morpholin-4-yl-ethyl)-amine | 9 |
| 57 | 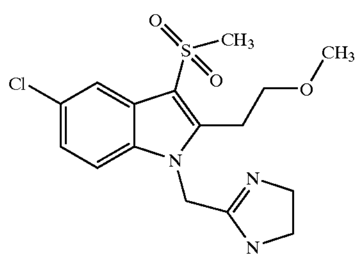 | 5-Chloro-1-(4,5-dihydro-1H-imidazol-2-ylmethyl)-3-methanesulfonyl-2-(2-methoxy-ethyl)-1H-indole | 11 |
| 58 | 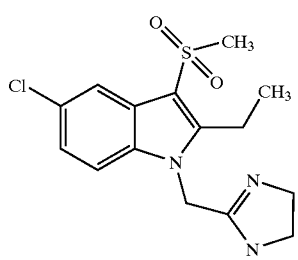 | 5-Chloro-1-(4,5-dihydro-1H-imidazol-2-ylmethyl)-2-ethyl-3-methanesulfonyl-1H-indole | 13 |
| 59 | 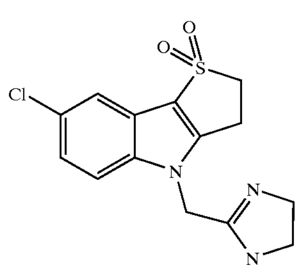 | 7-Chloro-4-(4,5-dihydro-1H-imidazol-2-ylmethyl)-3,4-dihydro-2H-thieno[3,2-b]indole 1,1-dioxide | 14 |

TABLE 1-continued

| Compound | Structure | Name (Autonom) | Example |
|---|---|---|---|
| 60 | 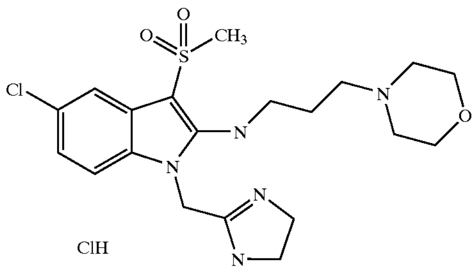 | [5-Chloro-1-(4,5-dihydro-1H-imidazol-2-ylmethyl)-3-methanesulfonyl-1H-indol-2-yl]-(3-morpholin-4-yl-propyl)-amine | 9 |
| 61 | 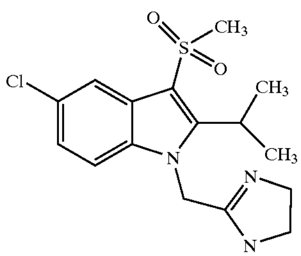 | 5-Chloro-1-(4,5-dihydro-1H-imidazol-2-ylmethyl)-2-isopropyl-3-methanesulfonyl-1H-indole | 13 |
| 62 | 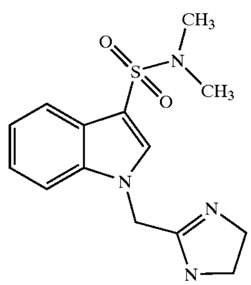 | 1-(4,5-Dihydro-1H-imidazol-2-ylmethyl)-1H-indole-3-sulfonic acid dimethylamide | 6 |
| 63 | 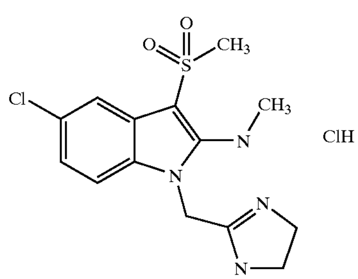 | [5-Chloro-1-(4,5-dihydro-1H-imidazol-2-ylmethyl)-3-methanesulfonyl-1H-indol-2-yl]-methyl-amine | 9 |
| 64 | 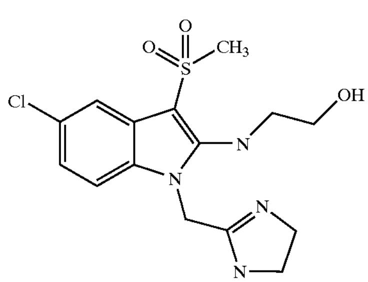 | 2-[5-Chloro-1-(4,5-dihydro-1H-imidazol-2-ylmethyl)-3-methanesulfonyl-1H-indol-2-ylamino]-ethanol | 9 |

TABLE 1-continued

| Compound | Structure | Name (Autonom) | Example |
|---|---|---|---|
| 65 | 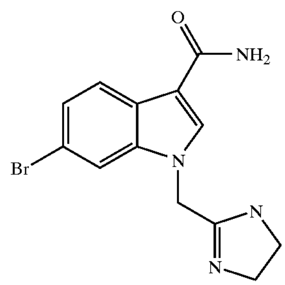 | 6-Bromo-1-(4,5-dihydro-1H-imidazol-2-ylmethyl)-1H-indole-3-carboxylic acid amide | 17 |
| 66 | 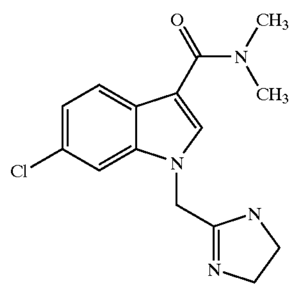 | 6-Chloro-1-(4,5-dihydro-1H-imidazol-2-ylmethyl)-1H-indole-3-carboxylic acid dimethylamide | 18 |
| 67 | 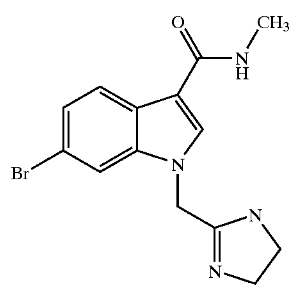 | 6-Bromo-1-(4,5-dihydro-1H-imidazol-2-ylmethyl)-1H-indole-3-carboxylic acid methylamide | 17 |
| 68 | 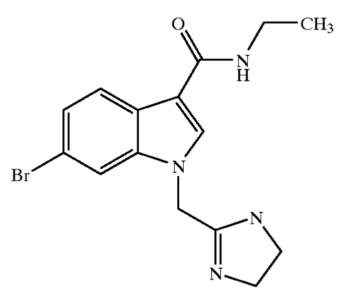 | 6-Bromo-1-(4,5-dihydro-1H-imidazol-2-ylmethyl)-1H-indole-3-carboxylic acid ethylamide | 17 |
| 69 | 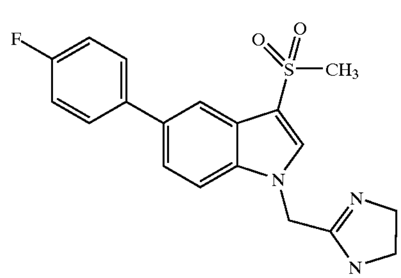 | 1-(4,5-dihydro-1H-imidazol-2-ylmethyl)-5-(4-fluorophenyl)-3-methanesulfonyl-1H-indole | 1 |

TABLE 1-continued

| Compound | Structure | Name (Autonom) | Example |
|---|---|---|---|
| 70 | 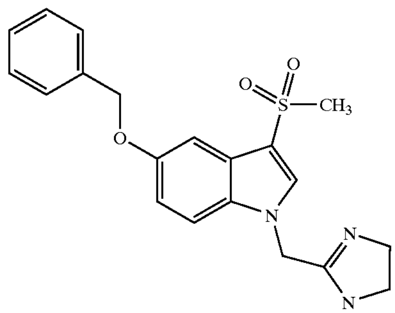 | 5-Benzyloxy-1-(4,5-dihydro-1H-imidazol-2-ylmethyl)-3-methanesulfonyl-1H-indole | 1 |
| 71 | 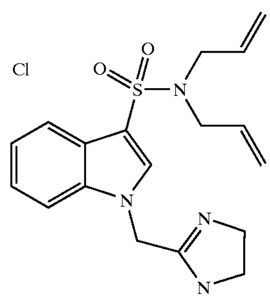 | 1-(4,5-Dihydro-1H-imidazol-2-ylmethyl)-1H-indole-3-sulfonic acid diallylamide | 6 |
| 72 | 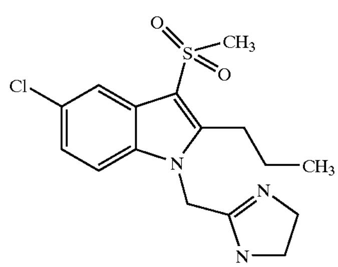 | 5-Chloro-1-(4,5-dihydro-1H-imidazol-2-ylmethyl)-3-methanesulfonyl-2-propyl-1H-indole | 5 |
| 73 | 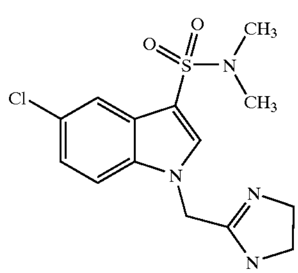 | 5-Chloro-1-(4,5-dihydro-1H-imidazol-2-ylmethyl)-1H-indole-3-sulfonic acid dimethylamide | 5 |
| 74 | 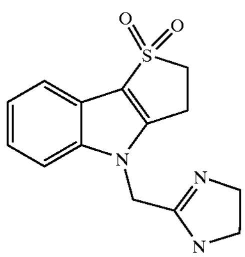 | 4-(4,5-Dihydro-1H-imidazol-2-ylmethyl)-3,4-dihydro-2H-thienol[3,2-b]indole 1,1-dioxide | 14 |

TABLE 1-continued

| Compound | Structure | Name (Autonom) | Example |
|---|---|---|---|
| 75 | 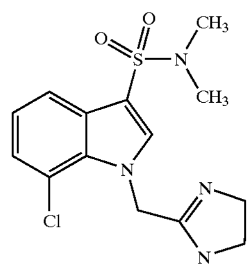 | 7-Chloro-1-(4,5-dihydro-1H-imidazol-2-ylmethyl)-1H-indole-3-sulfonic acid dimethylamide | 16 |
| 76 | 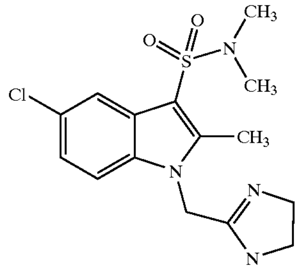 | 5-Chloro-1-(4,5-dihydro-1H-imidazol-2-ylmethyl)-2-methyl-1H-indole-3-sulfonic acid dimethylamide | 16 |
| 77 | 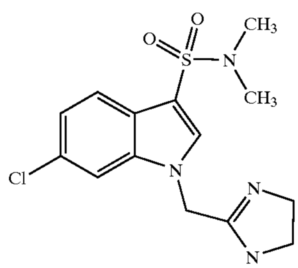 | 6-Chloro-1-(4,5-dihydro-1H-imidazol-2-ylmethyl)-1H-indole-3-sulfonic acid dimethylamide | 16 |
| 78 | 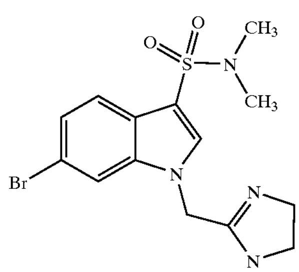 | 6-Bromo-1-(4,5-dihydro-1H-imidazol-2-ylmethyl)-1H-indole-3-sulfonic acid dimethylamide | 16 |
| 79 | 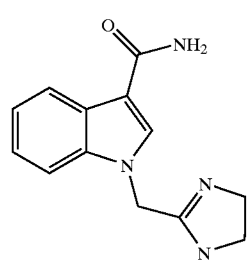 | 1-(4,5-dihydro-1H-imidazol-2-ylmethyl)-1H-indole-3-carboxylic acid amide | 17 |

TABLE 1-continued

| Compound | Structure | Name (Autonom) | Example |
|---|---|---|---|
| 80 | 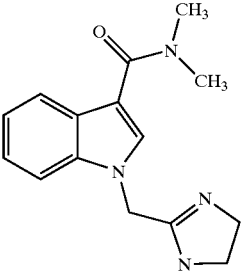 | 1-(4,5-dihydro-1H-imidazol-2-ylmethyl)-1H-indole-3-carboxylic acid dimethylamide | 17 |
| 81 | 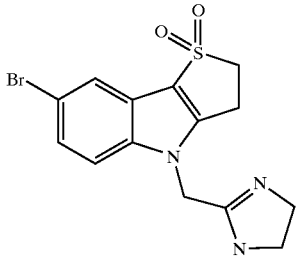 | 7-Bromo-4-(4,5-Dihydro-1H-imidazol-2-ylmethyl)-3,4-dihydro-2H-thieno[3,2-b]indole 1,1-dioxide | 14 |
| 82 | 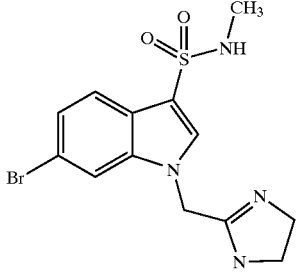 | 6-Bromo-1-(4,5-dihydro-1H-imidazol-2-ylmethyl)-1H-indole-3-sulfonic acid methylamide | 16 |
| 83 | 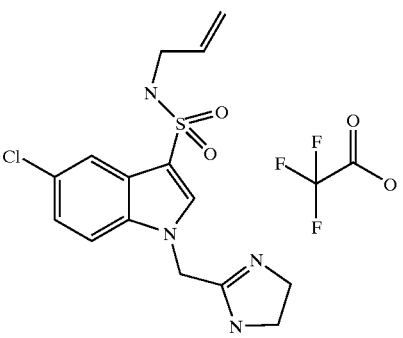 | 5-Chloro-1-(4,5-Dihydro-1H-imidazol-2-ylmethyl)-1H-indole-3-sulfonic acid allylamide | 19 |
| 84 | 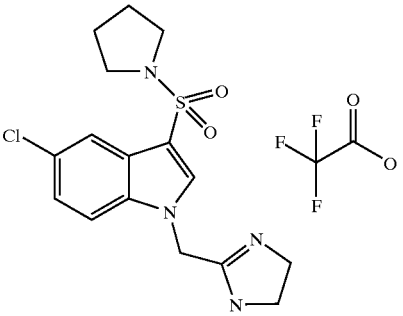 | 5-Chloro-1-(4,5-Dihydro-1H-imidazol-2-ylmethyl)-3-(pyrrolidine-1-sulfonyl)-1H-indole | 19 |

TABLE 1-continued

| Compound | Structure | Name (Autonom) | Example |
|---|---|---|---|
| 85 | 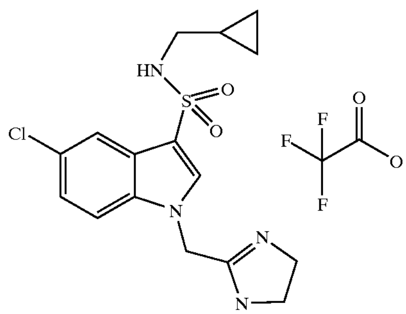 | 5-Chloro-1-(4,5-Dihydro-1H-imidazol-2-ylmethyl)-1H-indole-3-sulfonic acid cyclopropylmethylamide | 19 |
| 86 | 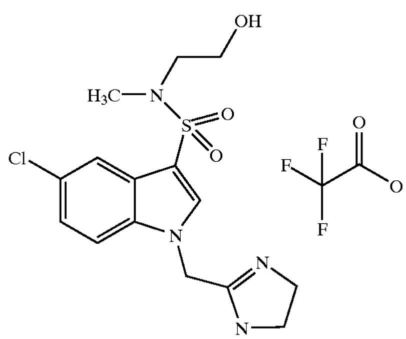 | 5-Chloro-1-(4,5-dihydro-1H-imidazol-2-ylmethyl)-1H-indole-3-sulfonic acid (2-hydroxy-ethyl)-methyl-amide | 19 |
| 87 | 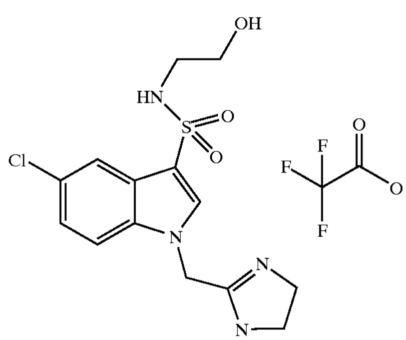 | 5-Chloro-1-(4,5-Dihydro-1H-imidazol-2-ylmethyl)-1H-indole-3-sulfonic acid (2-hydroxyethyl)-amide | 19 |
| 88 | 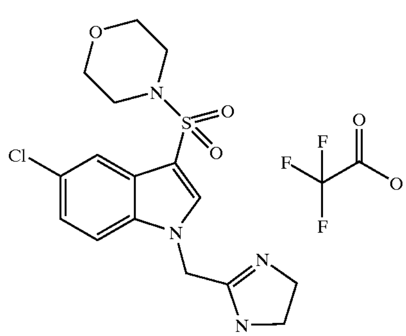 | 5-Chloro-1-(4,5-Dihydro-1H-imidazol-2-ylmethyl)-3-(morpholine-4-sulfonyl)-1H-indole | 19 |

TABLE 1-continued

| Compound | Structure | Name (Autonom) | Example |
|---|---|---|---|
| 89 | 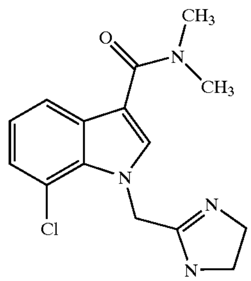 | 7-Chloro-1-(4,5-dihydro-1H-imidazol-2-ylmethyl)-1H-indole-3-sulfonic acid dimethylamide | 17 |
| 90 | 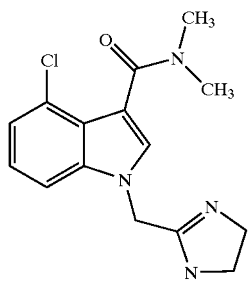 | 4-Chloro-1-(4,5-dihydro-1H-imidazol-2-ylmethyl)-1H-indole-3-sulfonic acid dimethylamide | 17 |
| 91 | 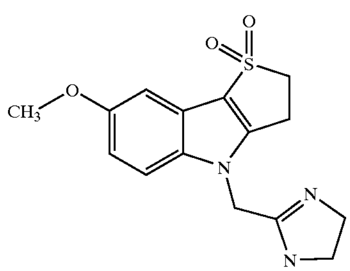 | 4-(4,5-Dihydro-1H-imidazol-2-ylmethyl)-7-methoxy-3,4-dihydro-2H-thieno[3,2-b]indole 1,1-dioxide | 14 |
| 92 | 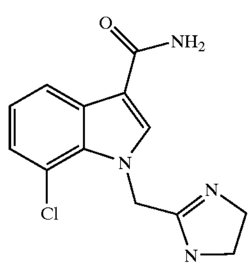 | 7-Chloro-1-(4,5-dihydro-1H-imidazol-2-ylmethyl)-1H-indole-3-carboxylic acid amide | 17 |
| 93 | 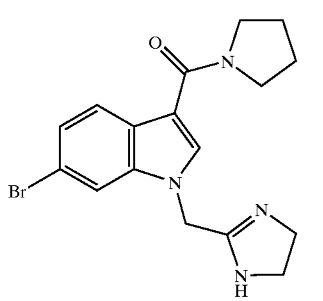 | [6-Bromo-1-(4,5-dihydro-1H-imidazol-2-ylmethyl)-1H-indol-3-yl]-pyrrolidin-1-yl-methanone | 17 |

TABLE 1-continued

| Compound | Structure | Name (Autonom) | Example |
|---|---|---|---|
| 94 | 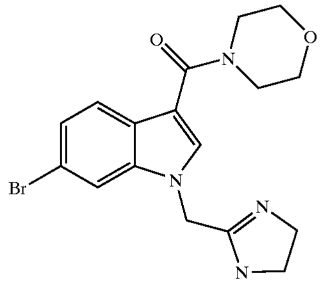 | [6-Bromo-1-(4,5-dihydro-1H-imidazol-2-ylmethyl)-1H-indol-3-yl]-morpholin-4-yl-methanone | 17 |
| 95 | 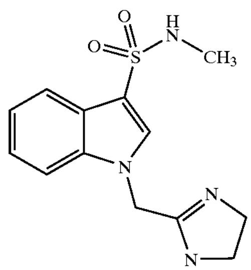 | 1-(4,5-Dihydro-1H-imidazol-2-ylmethyl)-1H-indole-3-sulfonic acid methylamide | 19 |
| 96 | 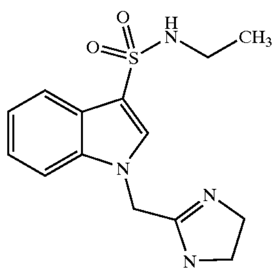 | 1-(4,5-Dihydro-1H-imidazol-2-ylmethyl)-1H-indole-3-sulfonic acid ethylamide | 19 |
| 97 | 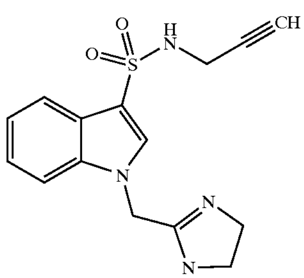 | 1-(4,5-Dihydro-1H-imidazol-2-ylmethyl)-1H-indole-3-sulfonic acid prop-2-ynylamide | 19 |
| 98 | 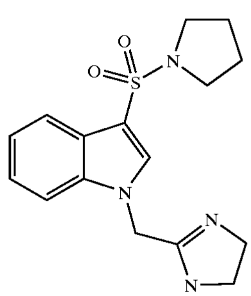 | 1-(4,5-Dihydro-1H-imidazol-2-ylmethyl)-3-(pyrrolidine-1-sulfonyl)-1H-indole | 19 |

TABLE 1-continued

| Compound | Structure | Name (Autonom) | Example |
|---|---|---|---|
| 99 | 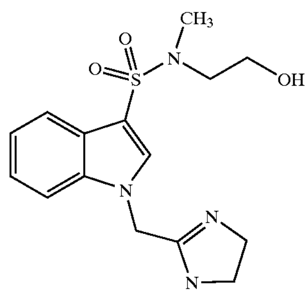 | 1-(4,5-Dihydro-1H-imidazol-2-ylmethyl)-1H-indole-3-sulfonic acid (2-hydroxy-ethyl)-methyl-amide | 19 |
| 100 | 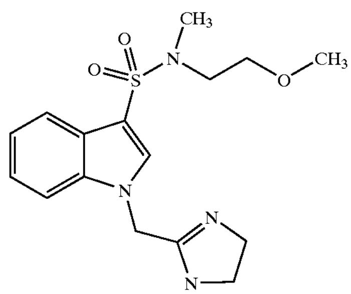 | 1-(4,5-Dihydro-1H-imidazol-2-ylmethyl)-1H-indole-3-sulfonic acid (2-methoxy-ethyl)-methyl-amide | 19 |
| 101 | 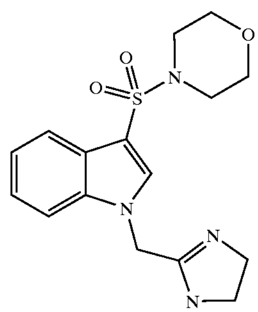 | 1-(4,5-Dihydro-1H-imidazol-2-ylmethyl)-3-(morpholine-4-sulfonyl)-1H-indole | 19 |
| 102 | 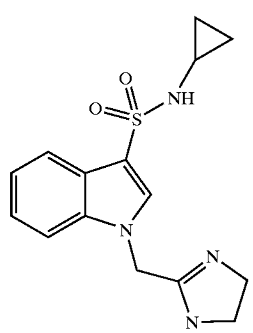 | 1-(4,5-Dihydro-1H-imidazol-2-ylmethyl)-1H-indole-3-sulfonic acid cyclopropylamide | 19 |
| 103 | 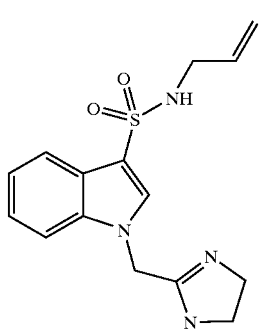 | 1-(4,5-Dihydro-1H-imidazol-2-ylmethyl)-1H-indole-3-sulfonic acid allylamide | 19 |

TABLE 1-continued

| Compound | Structure | Name (Autonom) | Example |
|---|---|---|---|
| 104 | 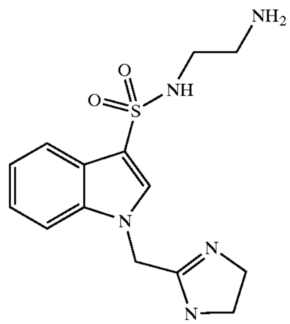 | 1-(4,5-Dihydro-1H-imidazol-2-ylmethyl)-1H-indole-3-sulfonic acid (2-amino-ethyl)-amide | 19 |
| 105 | 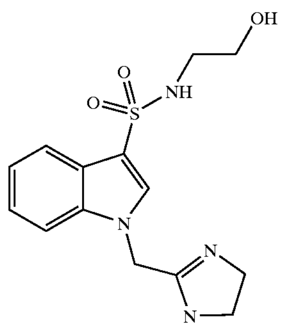 | 1-(4,5-Dihydro-1H-imidazol-2-ylmethyl)-1H-indole-3-sulfonic acid (2-hydroxy-ethyl)-amide | 19 |
| 106 | 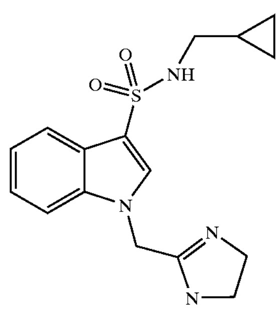 | 1-(4,5-Dihydro-1H-imidazol-2-ylmethyl)-1H-indole-3-sulfonic acid cyclopropylmethyl-amide | 19 |
| 107 | 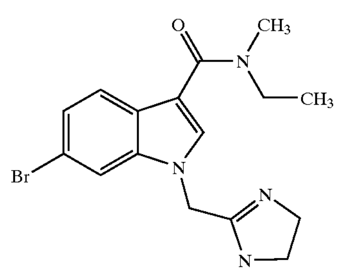 | 6-Bromo-1-(4,5-dihydro-1H-imidazol-2-ylmethyl)-1H-indole-3-carboxylic acid ethyl-methyl-amide | 17 |
| 108 | 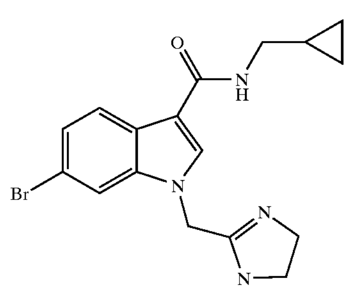 | 6-Bromo-1-(4,5-dihydro-1H-imidazol-2-ylmethyl)-1H-indole-3-carboxylic acid cyclopropylmethyl-amide | 17 |

TABLE 1-continued

| Compound | Structure | Name (Autonom) | Example |
|---|---|---|---|
| 109 | 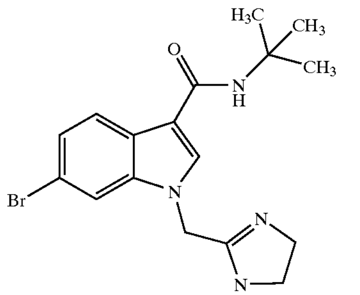 | 6-Bromo-1-(4,5-dihydro-1H-imidazol-2-ylmethyl)-1H-indole-3-carboxylic acid tert-butylamide | 17 |
| 110 | 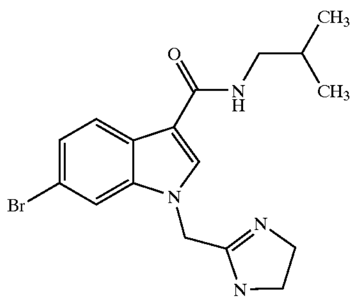 | 6-Bromo-1-(4,5-dihydro-1H-imidazol-2-ylmethyl)-1H-indole-3-carboxylic acid isobutyl-amide | 17 |
| 111 | 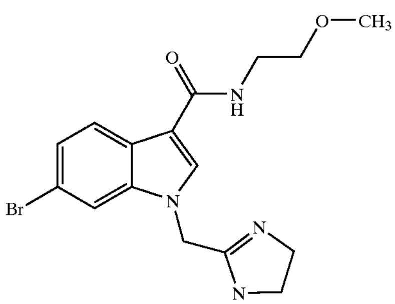 | 6-Bromo-1-(4,5-dihydro-1H-imidazol-2-ylmethyl)-1H-indole-3-carboxylic acid (2-methoxy-ethyl)-amide | 17 |
| 112 | 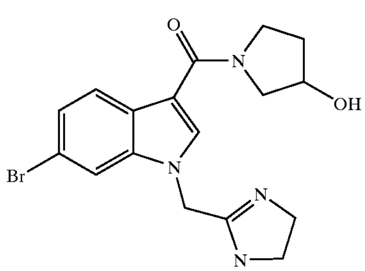 | [6-Bromo-1-(4,5-dihydro-1H-imidazol-2-ylmethyl)-1H-indol-3-yl]-(3-hydroxy-pyrrolidin-1-yl)-methanone | 17 |
| 113 | 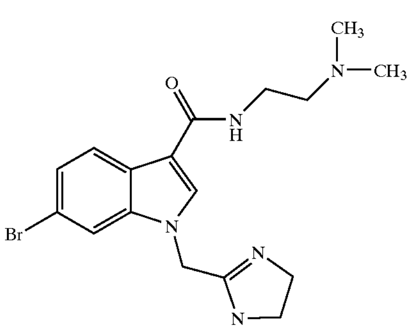 | 6-Bromo-1-(4,5-dihydro-1H-imidazol-2-ylmethyl)-1H-indole-3-carboxylic acid (2-dimethylamino-ethyl)-amide | 17 |

TABLE 1-continued

| Compound | Structure | Name (Autonom) | Example |
|---|---|---|---|
| 114 | 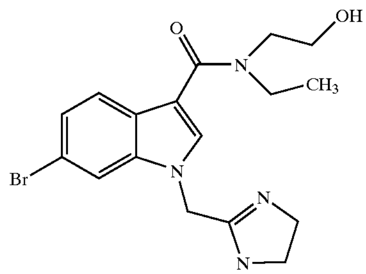 | 6-Bromo-1-(4,5-dihydro-1H-imidazol-2-ylmethyl)-1H-indole-3-carboxylic acid ethyl-(2-hydroxy-ethyl)-amide | 17 |
| 115 | 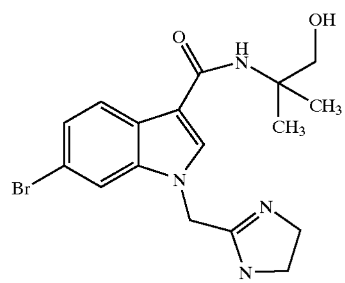 | 6-Bromo-1-(4,5-dihydro-1H-imidazol-2-ylmethyl)-1H-indole-3-carboxylic acid (2-hydroxy-1,1-dimethyl-ethyl)-amide | 17 |
| 116 | 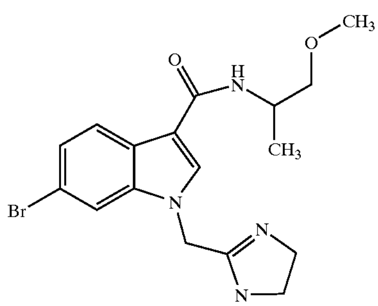 | 6-Bromo-1-(4,5-dihydro-1H-imidazol-2-ylmethyl)-1H-indole-3-carboxylic acid (2-methoxy-1-methyl-ethyl)-amide | 17 |
| 117 | 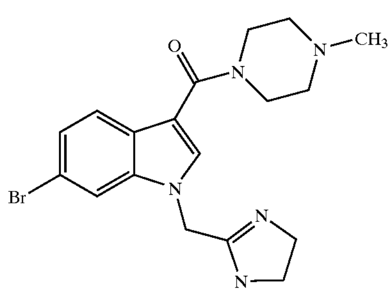 | [6-Bromo-1-(4,5-dihydro-1H-imidazol-2-ylmethyl)-1H-indol-3-yl]-(4-methyl-piperazin-1-yl)-methanone | 17 |
| 118 | 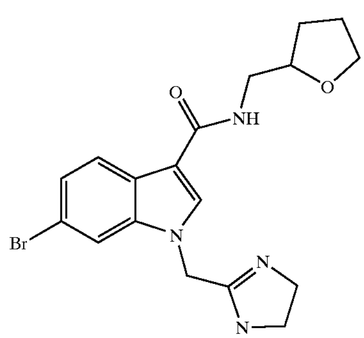 | 6-Bromo-1-(4,5-dihydro-1H-imidazol-2-ylmethyl)-1H-indole-3-carboxylic acid (tetrahydro-furan-2-ylmethyl)-amide | 17 |

TABLE 1-continued

| Compound | Structure | Name (Autonom) | Example |
|---|---|---|---|
| 119 | 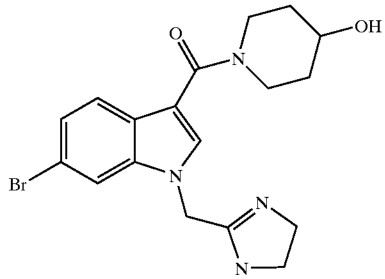 | [6-Bromo-1-(4,5-dihydro-1H-imidazol-2-ylmethyl)-1H-indol-3-yl]-(4-hydroxy-piperidin-1-yl)-methanone | 17 |
| 120 | 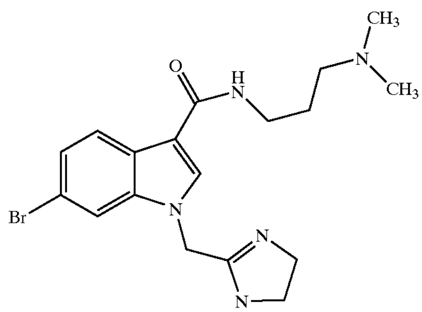 | 6-Bromo-1-(4,5-dihydro-1H-imidazol-2-ylmethyl)-1H-indole-3-carboxylic acid (3-dimethylamino-propyl)-amide | 17 |
| 121 | 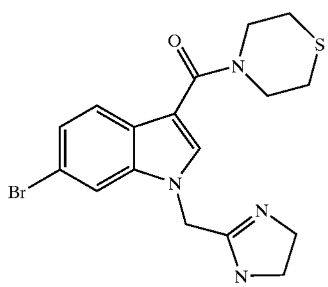 | [6-Bromo-1-(4,5-dihydro-1H-imidazol-2-ylmethyl)-1H-indol-3-yl]-thiomorpholin-4-yl-methanone | 17 |
| 122 | 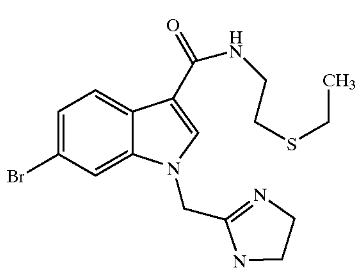 | 6-Bromo-1-(4,5-dihydro-1H-imidazol-2-ylmethyl)-1H-indole-3-carboxylic acid (2-ethylsulfanyl-ethyl)-amide | 17 |
| 123 | 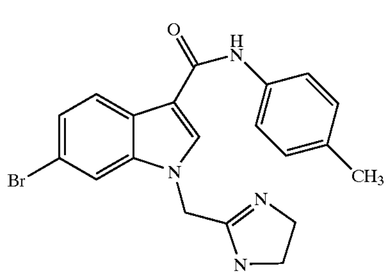 | 6-Bromo-1-(4,5-dihydro-1H-imidazol-2-ylmethyl)-1H-indole-3-carboxylic acid p-tolylamide | 17 |

TABLE 1-continued

| Compound | Structure | Name (Autonom) | Example |
|---|---|---|---|
| 124 | 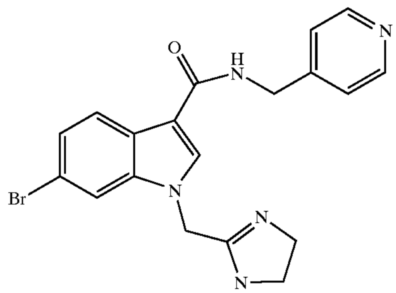 | 6-Bromo-1-(4,5-dihydro-1H-imidazol-2-ylmethyl)-1H-indole-3-carboxylic acid (pyridin-4-yl-methyl)-amide | 17 |
| 125 | 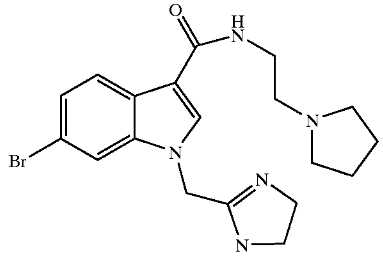 | 6-Bromo-1-(4,5-dihydro-1H-imidazol-2-ylmethyl)-1H-indole-3-carboxylic acid (2-pyrrolidin-1-yl-ethyl)-amide | 17 |
| 126 | 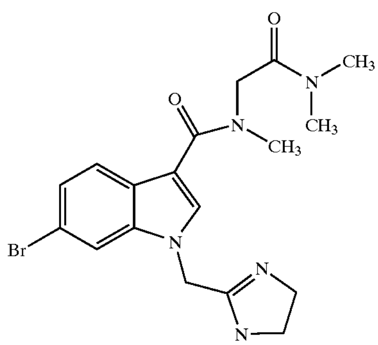 | 6-Bromo-1-(4,5-dihydro-1H-imidazol-2-ylmethyl)-1H-indole-3-carboxylic acid dimethylcarbamoylmethyl-methyl-amide | 17 |
| 127 | 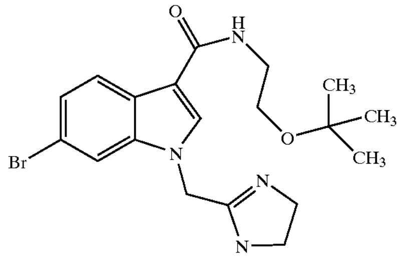 | 6-Bromo-1-(4,5-dihydro-1H-imidazol-2-ylmethyl)-1H-indole-3-carboxylic acid (2-tert-butoxy-ethyl)-amide | 17 |
| 128 | 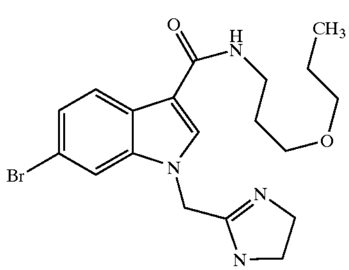 | 6-Bromo-1-(4,5-dihydro-1H-imidazol-2-ylmethyl)-1H-indole-3-carboxylic acid (3-propoxy-propyl)-amide | 17 |

TABLE 1-continued

| Compound | Structure | Name (Autonom) | Example |
|---|---|---|---|
| 129 | 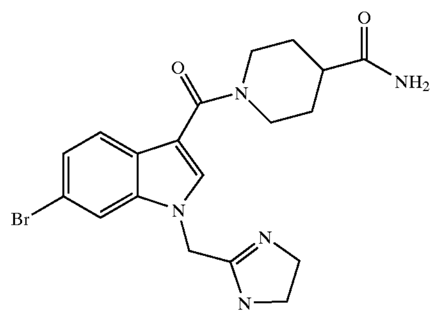 | 1-[6-Bromo-1-(4,5-dihydro-1H-imidazol-2-ylmethyl)-1H-indole-3-carbonyl]-piperidine-4-carboxylic acid amide | 17 |
| 130 | 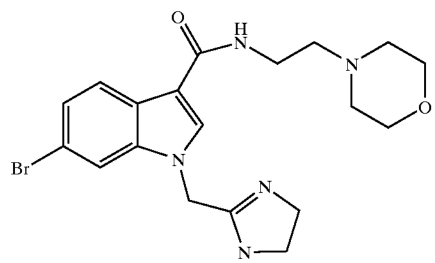 | 6-Bromo-1-(4,5-dihydro-1H-imidazol-2-ylmethyl)-1H-indole-3-carboxylic acid (2-morpholin-4-yl-ethyl)-amide | 17 |
| 131 | 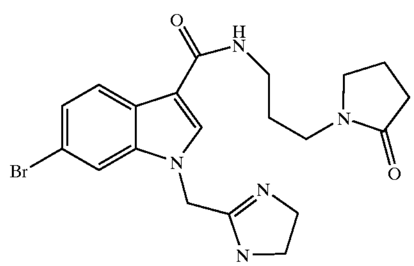 | 6-Bromo-1-(4,5-dihydro-1H-imidazol-2-ylmethyl)-1H-indole-3-carboxylic acid [3-(2-oxo-pyrrolidin-1-yl)-propyl]-amide | 17 |
| 132 | 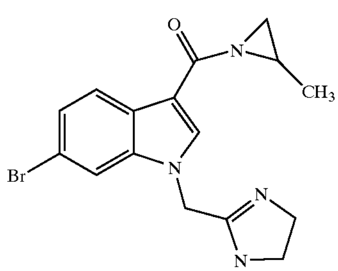 | [6-Bromo-1-(4,5-dihydro-1H-imidazol-2-ylmethyl)-1H-indol-3-yl]-(2-methyl-aziridin-1-yl)-methanone | 17 |
| 133 | 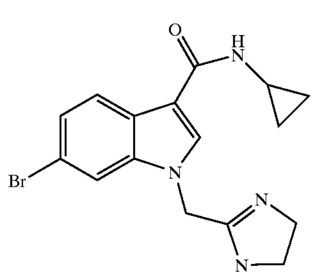 | 6-Bromo-1-(4,5-dihydro-1H-imidazol-2-ylmethyl)-1H-indole-3-carboxylic acid cyclopropylamide | 17 |

TABLE 1-continued

| Compound | Structure | Name (Autonom) | Example |
|---|---|---|---|
| 134 | 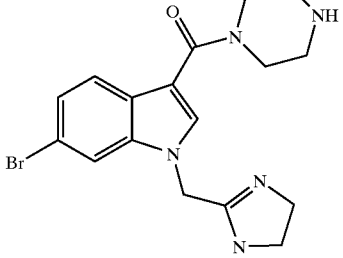 | [6-Bromo-1-(4,5-dihydro-1H-imidazol-2-ylmethyl)-1H-indol-3-yl]-piperazin-1-yl-methanone | 17 |
| 135 | 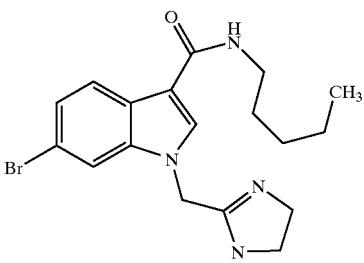 | 6-Bromo-1-(4,5-dihydro-1H-imidazol-2-ylmethyl)-1H-indole-3-carboxylic acid pentylamide | 17 |
| 136 | 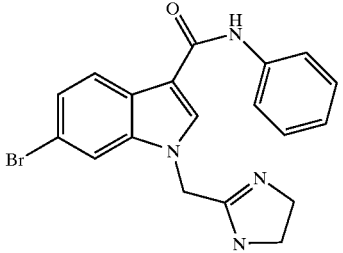 | 6-Bromo-1-(4,5-dihydro-1H-imidazol-2-ylmethyl)-1H-indole-3-carboxylic acid phenylamide | 17 |
| 137 | 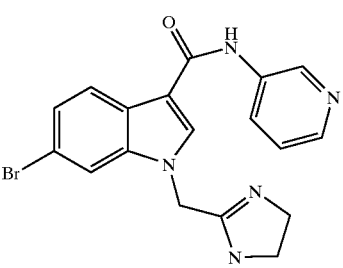 | 6-Bromo-1-(4,5-dihydro-1H-imidazol-2-ylmethyl)-1H-indole-3-carboxylic acid pyridin-3-ylamide | 17 |
| 138 | 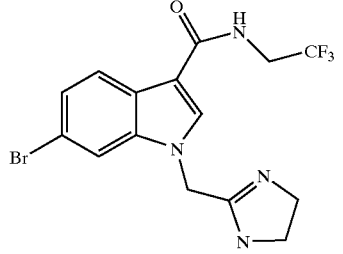 | 6-Bromo-1-(4,5-dihydro-1H-imidazol-2-ylmethyl)-1H-indole-3-carboxylic acid (2,2,2-trifluoro-ethyl)-amide | 17 |

TABLE 1-continued

| Compound | Structure | Name (Autonom) | Example |
|---|---|---|---|
| 139 | 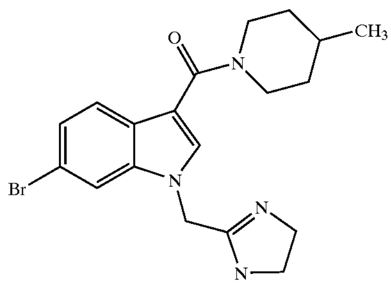 | [6-Bromo-1-(4,5-dihydro-1H-imidazol-2-ylmethyl)-1H-indol-3-yl]-(4-methyl-piperidin-1-yl)-methanone | 17 |
| 140 | 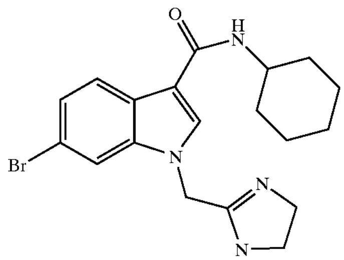 | 6-Bromo-1-(4,5-dihydro-1H-imidazol-2-ylmethyl)-1H-indole-3-carboxylic acid cyclohexylamide | 17 |
| 141 | 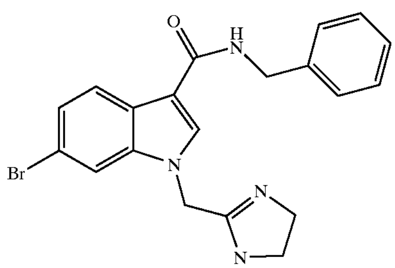 | 6-Bromo-1-(4,5-dihydro-1H-imidazol-2-ylmethyl)-1H-indole-3-carboxylic acid benzylamide | 17 |
| 142 | 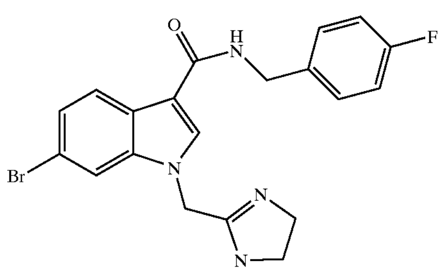 | 6-Bromo-1-(4,5-dihydro-1H-imidazol-2-ylmethyl)-1H-indole-3-carboxylic acid (4-fluoro-phenyl)-amide | 17 |
| 143 | 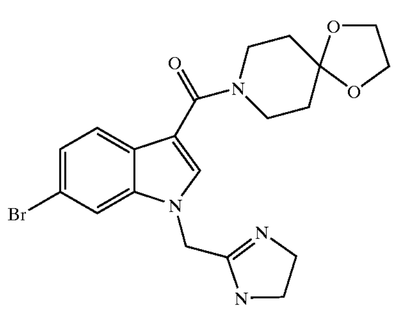 | [6-Bromo-1-(4,5-dihydro-1H-imidazol-2-ylmethyl)-1H-indol-3-yl]-(1,4-dioxa-8-aza-spiro[4.5]dec-8-yl)-methanone | 17 |

TABLE 1-continued

| Compound | Structure | Name (Autonom) | Example |
|---|---|---|---|
| 144 | 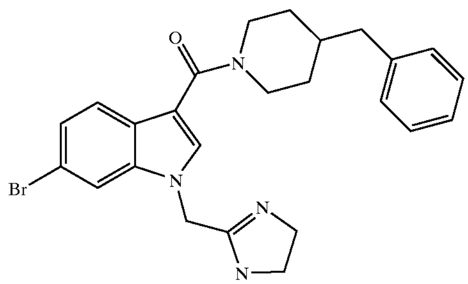 | (4-Benzyl-piperazin-1-yl)-[6-bromo-1-(4,5-dihydro-1H-imidazol-2-ylmethyl)-1H-indol-3-yl]-methanone | 17 |
| 145 | 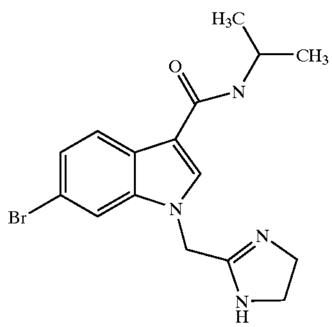 | 6-Bromo-1-(4,5-dihydro-1H-imidazol-2-ylmethyl)-1H-indole-3-carboxylic acid isopropylamide | 17 |
| 146 | 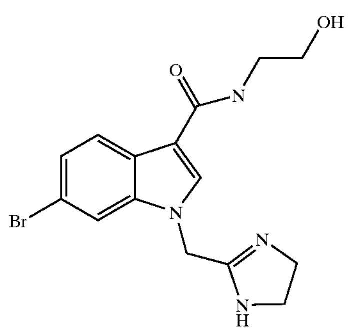 | 6-Bromo-1-(4,5-dihydro-1H-imidazol-2-ylmethyl)-1H-indole-3-carboxylic acid (2-hydroxy-ethyl)-amide | 17 |
| 147 | 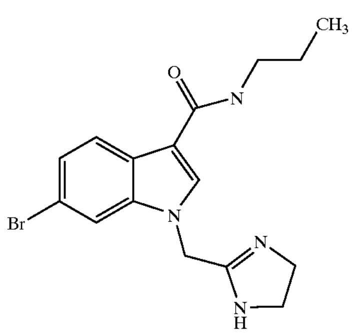 | 6-Bromo-1-(4,5-dihydro-1H-imidazol-2-ylmethyl)-1H-indole-3-carboxylic acid propylamide | 17 |
| 148 | 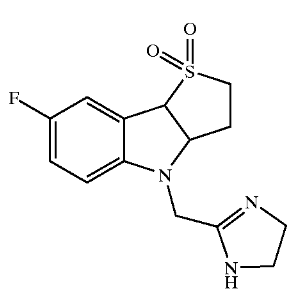 | 4-(4,5-Dihydro-1H-imidazol-2-ylmethyl)-7-fluoro-3,3a,4,8b-tetrahydro-2H-thieno[3,2-b]indole 1,1-dioxide | 17 |

TABLE 1-continued

| Compound | Structure | Name (Autonom) | Example |
|---|---|---|---|
| 149 | 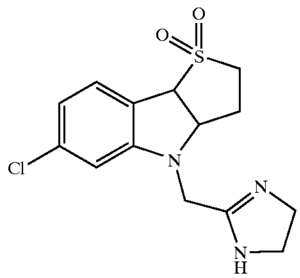 | 6-Chloro-4-(4,5-dihydro-1H-imidazol-2-ylmethyl)-3,3a,4,8b-tetrahydro-2H-thieno[3,2-b]indole 1,1-dioxide | 14 |
| 150 | 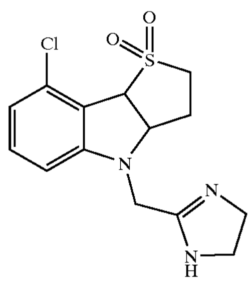 | 8-Chloro-4-(4,5-dihydro-1H-imidazol-2-ylmethyl)-3,3a,4,8b-tetrahydro-2H-thieno[3,2-b]indole 1,1-dioxide | 14 |

GENERAL SYNTHETIC REACTION SCHEMES

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. Where necessary, conventional protecting group techniques were used as described by Greene et al., *Protecting Groups in Organic Synthesis*, 3rd Ed., Wiley Interscience, 1999. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

Schemes A, B, C and D describe methods to generate compounds of Formula I.

SCHEME A
Scheme A describes a method of preparing a compound of Formula I wherein X is —S(O)$_n$——, R$^1$, R$^2$, R$^3$, R$^4$, R$^5$, R$^6$, R', R'', n, m, and A are as defined in the Summary of the Invention.

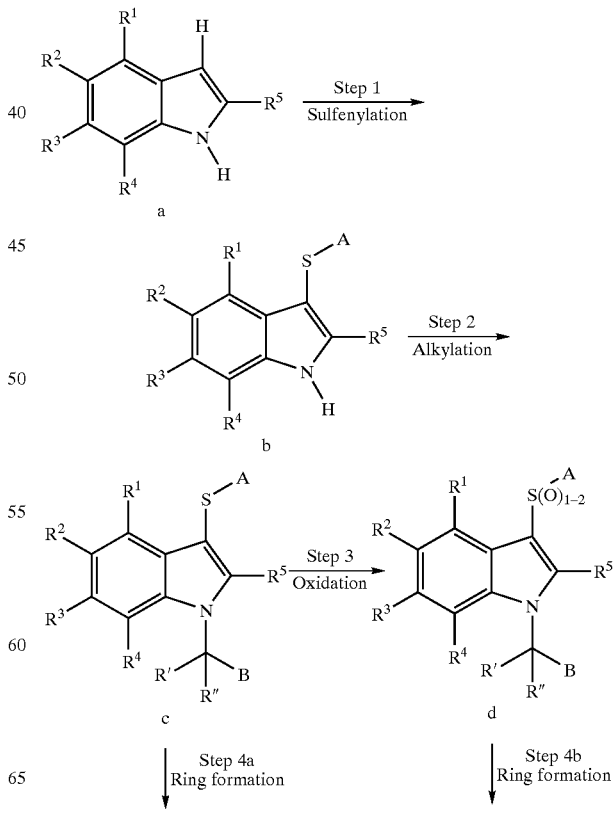

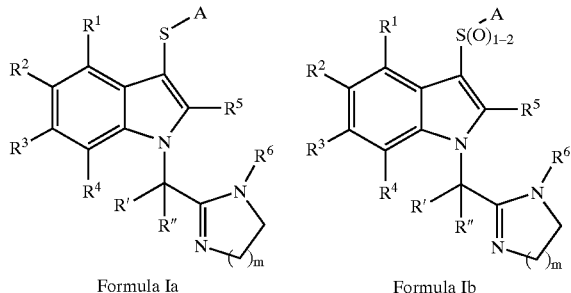

Formula Ia                    Formula Ib

Compound a can be converted into an indole-3-thioether of formula b by several routes well known in the art. For example, Tomita K., describes in *Heterocycles* 1976, 4 (4), 729–732 a synthesis of indole-3-thioethers with succinimido-dialkylsulfonium chloride or succinimido-alkylarylsulfonium chloride, prepared from dialkyl or alkylaryl sulfides and N-chlorosuccinimide which gave alkyl- or aryl-thioindoles, via an intermediate indol-3-yl dialkyl or alkylaryl sulfonium chloride. The decomposition of the sulfonium intermediate may occur spontaneously at room temperature or may require heating either neat under reduced pressure or suspended in an inert solvent preferably under an inert atmosphere. The temperature for decomposition varies from room temperature to 180° C., preferably in the range of 80–140° C., and may conveniently be accomplished in inert solvents such as xylene, toluene or DMSO.

An alternate route wherein a substituted indole can be treated with the appropriate sulfenylchloride to afford the thioindole directly, can be effected according to the procedure of Anzai K., *J. Heterocyclic Chem.,* 1979, 16, 567. The reaction is carried out with an equivalent of arylsulfenyl chloride in dichloromethane often with a co-solvent such as dimethylformamide.

In Step 2, the compound of formula b can be alkylated with a haloacetonitrile derivative, such as chloro-, bromo- or iodoacetonitrile to afford a compound of formula c, wherein B is a cyano group. The alkylation can be performed under aprotic conditions by alkylation following the creation of the anion generated by a strong base such as sodium hydride, or under phase transfer catalysis. Using synthetic techniques well known in the art, the compound of formula c, wherein B is an acid or ester group can be prepared by alkylation of a compound of formula b with the corresponding haloacetic ester or acid derivative.

In Step 3, the compound of formula c can be oxidized with a suitable amount of oxidizing agent such as Oxone™ (potassium peroxymonosulfate), MCPBA (m-chloroperoxybenzoic acid), and the like, to afford compound of formula d. Suitable solvents for this reaction are, for example aqueous alcohols (such as alkanols for example methanol or ethanol) when Oxone™ is used, or halogenated solvents (such as dichloromethane, chloroform and the like) or ether when MCPBA is used.

In Step 4a, the nitrile group of the compound of formula c can be treated with the appropriate alkylene diamine to afford the imidazoline group under conditions well known in the art, for example in the presence of heat and carbon disulfide, or with trimethylaluminum in an inert solvent such as toluene.

In Step 4b, the nitrile group of the compound of formula d can be treated with the appropriate alkylene diamine to afford the imidazoline or the tetrahydro pyrimidine group under conditions well known in the art, for example in the presence of heat and carbon disulfide, or with trimethylaluminum in an inert solvent such as toluene.

Compounds of Formula d can also be synthesized via the corresponding imidate acid salt prepared by the acid catalyzed addition of an alcohol to the nitrile, followed by the treatment of said imidate acid salt with the appropriate alkylenediamine.

Variants of the synthesis are possible. For example the order of reactions may be changed so as to substitute the indole nitrogen first with the acetonitrile moiety, (under conditions as described in step 3 supra), followed by sulfenylation (under conditions described in step 1 supra), optional oxidation (under conditions described in step 2 supra) and ring formation (as described in step 4 supra).

Alternatively the sequence may be changed by optionally oxidizing the sulfide to the sulfone first (under conditions described in step 2 supra), then alkylation of the nitrogen (under conditions described in step 3 supra) and ring formation(as described in step 4b supra).

SCHEME B
Scheme B describes an alternative method of preparing a compound of Formula I wherein X is
—S(O)$_n$—, R$^1$, R$^2$, R$^3$, R$^4$, R$^5$, R$^6$, R', R'', n, m, and A are as defined in the Summary of the Invention.

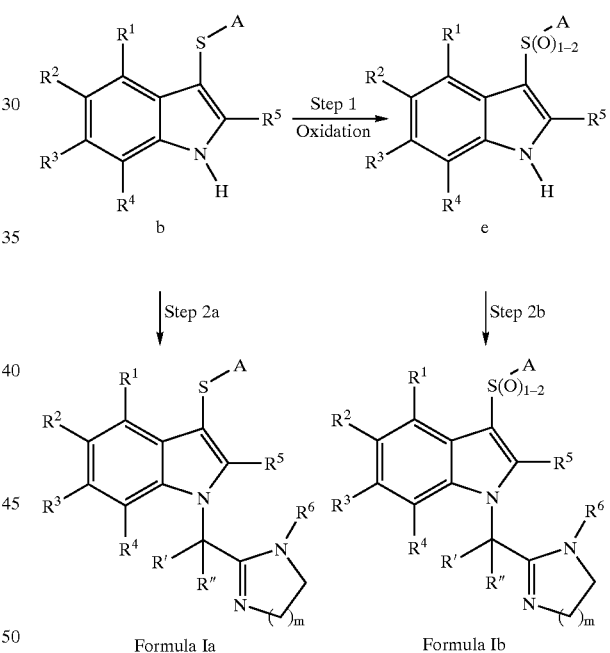

Formula Ia                    Formula Ib

A compound of formula b prepared as described in Scheme A, can undergo an oxidation under the conditions described supra, for example with a suitable oxidizing agent such as Oxone™ in a solvent such as aqueous alkanol, or MCPBA in a suitable solvent such as ether or a halogenated solvent, to afford a compound of formula e.

The alkylation of the indole in steps 2a and 2b may be effected with the appropriate halogenated imidazolylmethyl derivative or the tetrahydropyrimidine-methyl derivative in the presence of a base such as sodium hydride in an inert solvent such as dimethylformamide (DMF) or N-methylpyrrolidone(NMP). This alkylation can alternatively be effected with the appropriate haloacetonitrile derivative in the presence of a base such as sodium hydride, followed by ring formation with the appropriate ethylenediamine to afford the imidazolylmethyl derivative or the tetrahydropyrimidine derivative, under conditions as described supra.

Variants of the above synthetic schemes are possible and will suggest themselves to those skilled in the art. For example the order of reactions may be changed so as to substitute the indole nitrogen first with the acetonitrile moiety, (under conditions as described in step 3 supra), followed by sulfenylation (under conditions described in step 1 supra), optional oxidation (under conditions described in step 2 supra) and ring formation (as described in step 4 supra).

Alternatively the sequence may be changed by optionally oxidizing the sulfide to the sulfone first (under conditions described in step 2 supra), then alkylation of the nitrogen (under conditions described in step 3 supra) and ring formation(as described in step 4b supra).

Scheme C describes a method of preparing a compound of Formula I wherein X is —C(O)—, A is —NR$^a$R$^b$, and R$^1$, R$^2$, R$^3$, R$^4$, R$^5$, R$^6$, R', R", R$^a$, R$^b$, n, and m are as defined in the Summary of the Invention.

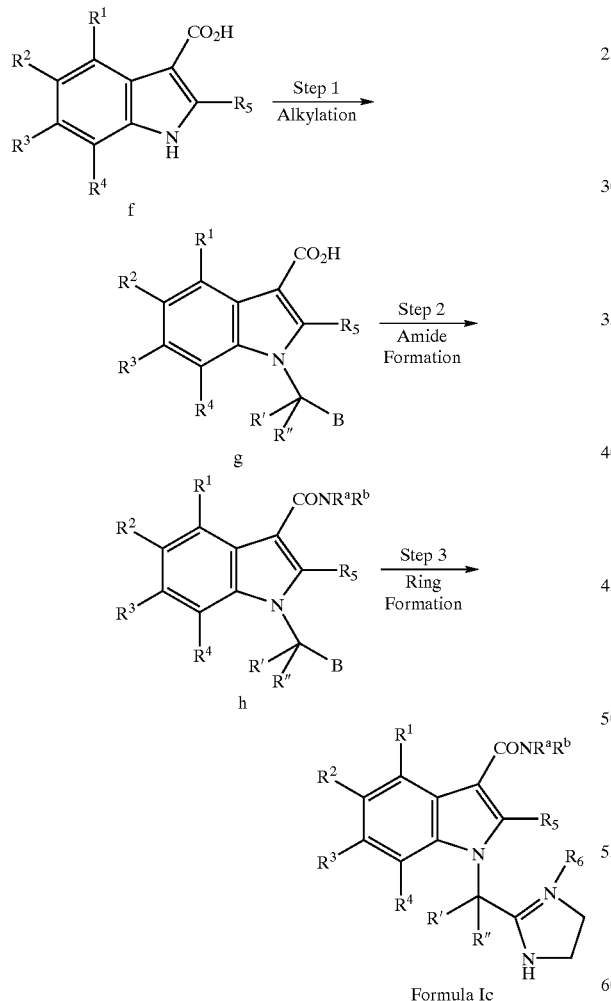

Indole-3-carboxylic acid compounds of formula f can be prepared by a variety of well-known techniques (see, e.g., Sundberg, R. J., *The Chemistry of Indoles*, Academic Press, New York 1970). Compound f can be alkylated in Step 1 with a haloacetonitrile derivative as described above for Scheme A to afford a compound of formula g, wherein B is a cyano group. The alkylation can be performed under aprotic conditions by alkylation following the creation of the anion generated by a strong base such as sodium hydride, or under phase transfer catalysis. Alkylation of compound f with haloacetic acid or haloacetic ester compounds may alternatively be carried out in Step 1, followed by conversion to the corresponding nitrile using well-known synthetic techniques.

In Step 2, the carboxyl group of compound g can be converted to an amide by forming a carboxylic acid chloride followed by treatment with an amine of the formula NHR$^a$R$^b$ to provide the corresponding carboxylic acid amide. Formation of the acid chloride of compound g may be carried out by reaction of compound g with oxalyl chloride in a dry, polar aprotic solvent, followed directly by addition of the amine, as described in the experimental examples below.

In Step 3, the nitrile group of the compound of formula h can be treated with an appropriate alkylene diamine to afford the imidazoline as described above with regard to Scheme A.

Scheme D describes another method of preparing a compound of Formula I wherein X is —C(O)—, A is —NR$^a$R$^b$, and R$^1$, R$^2$, R$^3$, R$^4$, R$^5$, R$^6$, R', R", R$^a$, R$^b$, n, and m are as defined above.

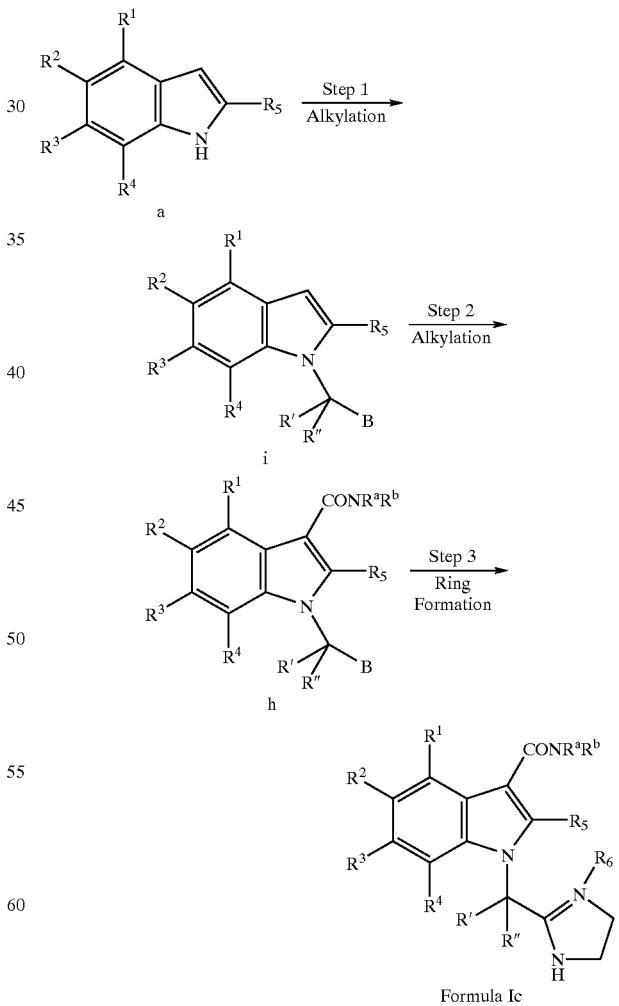

In Scheme D the indole compound a is N-alkylated in Step 1 at position 1 with a haloacetonitrile derivative as shown in Scheme A and described above to provide the compound i. Compound i can in turn be alkylated at the 3-position in Step 2 using added dichloromethylene dimethylammonium chloride (phosgene imminium chloride) under polar aprotic conditions to provide the compound h. Imidazoline formation in Step 3 may then be achieved for compound h by treatment with the desired alkylene diamine as described above.

Variations of the synthetic schemes described herein are possible and will suggest themselves to those skilled in the art. Those skilled in the art will also recognize that stereocenters exist in some compounds of Formula I. Accordingly, the present invention includes all possible stereoisomers and geometric isomers of Formula I, and includes not only racemic compounds but also the optically active isomers as well. When a compound of Formula I, is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See for example, *Stereochemistry of Carbon Compounds* by E. L. Eliel (McGraw Hill, 1962) and *Tables of Resolving Agents* by S. H. Wilen.

General Utility

The compounds of the present invention have selective alpha-1A/L adrenergic selective activity and as such are expected to be useful in the treatment of various disease states, such as urinary incontinence; nasal congestion; sexual dysfunction, such as ejaculation disorders and priapism; CNS disorders such as depression, anxiety, dementia, senility, Alzheimer's, deficiencies in attentiveness and cognition, and eating disorders such as obesity, bulimia, and anorexia.

Urinary incontinence (UI) is a condition defined as the involuntary loss of urine to such an extent as to become a hygienic or social concern to the patient. Involuntary loss of urine occurs when pressure inside the bladder exceeds retentive pressure of the urethral sphincters (intraurethral pressure). Four major types of urinary incontinence have been defined based on symptoms, signs and condition: stress, urge, overflow and functional incontinence.

Stress urinary incontinence (SUI) is the involuntary loss of urine during coughing, sneezing, laughing, or other physical activities. The present methods to treat SUI include physiotherapy and surgery. Treatment with pharmaceutical agents is limited to the use of non selective-adrenergic agonists like phenylproanolamine and midodrine. The rationale for the use of adrenergic agonists for the treatment of SUI is based on physiological data indicating an abundant noradrenergic input to smooth muscle of the urethra.

Urge incontinence (detrusor instability) is the involuntary loss of urine associated with a strong urge to void. This type of incontinence is the result of either an overactive or hypersensitive detrusor muscle. The patient with detrusor overactivity experiences inappropriate detrusor contractions and increases in intravesical pressure during bladder filling. Detrusor instability resulting from a hypersensitive detrusor (detrusor hyperreflexia) is most often associated with a neurological disorder.

Overflow incontinence is an involuntary loss of urine resulting from a weak detrusor or from the failure of the detrusor to transmit appropriate signals (sensory) when the bladder is full. Overflow incontinent episodes are characterized by frequent or continuous dribbling of urine and incomplete or unsuccessful voiding.

Functional incontinence, in contrast to the types of incontinence described above, is not defined by an underlying physiological dysfunction in the bladder or urethra. This type of incontinence includes the involuntary loss of urine resulting from such factors as decreased mobility, medications (e.g., diuretics, muscarinic agents, or alpha-1 adrenoceptor antagonists), or psychiatric problems such as depression or cognitive impairment.

The compounds of this invention are also particularly useful for the treatment of nasal congestion associated with allergies, colds, and other nasal disorders, as well as the sequelae of congestion of the mucous membranes (for example, sinusitis and otitis media) with less or no undesired side effects.

These and other therapeutic uses are described, for example, in *Goodman & Gilman's, The Pharmacological Basis of Therapeutics*, ninth edition, McGraw-Hill, New York, 1996, Chapter 26:601–616; and Coleman, R. A., *Pharmacological Reviews*, 1994, 46:205–229.

Testing

General Strategy for Identifying Alpha-1A/L-Adrenoceptor Agonists:

In Vitro:

The inhibitory activity of compounds of this invention in vitro was examined using fluorescent dye determination of intracellular calcium concentrations as described in Example 6.

Alpha-1A/L-adrenoceptor agonist activity was determined in vitro and in vivo as described in Example 7.

In Vitro:

The activity of potential alpha-1A/L activity in vitro was determined by evaluating the potency and relative intrinsic activity (relative to norepinephrine or phenylephrine) of standard and novel compounds to contract isolated rabbit bladder neck strips (alpha-1A/L-adrenoceptor) and isolated rat aortic rings (alpha-1D adrenoceptor).

In Vivo:

Standard and novel compounds which selectively contracted rabbit bladder neck strips were subsequently evaluated in vivo in anesthetized female micropigs to assess urethral activity relative to diastolic blood pressure effects. Compounds with the desired activity in anesthetized pigs were evaluated in conscious female micropigs instrumented with telemetry to measure diastolic blood pressure and a strain-gage transducer to measure urethral tension.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Example 5.

EXAMPLES

The following preparations and examples are given to enable those skilled in the art to more clearly understand and to practice the present invention. They should not be considered as limiting the scope of the invention, but merely as being illustrative and representative thereof.

Efforts have been made to ensure accuracy with respect to numbers used (e.g., amounts, temperatures, etc.), but some experimental error and deviation should, of course, be allowed for as well as due to differences such as, for example, in calibration, rounding of numbers, and the like.

Example 1

1-(4,5-Dihydro-1H-imidazol-2-ylmethyl)-3-methanesulfonyl-2-methyl-1H-indole

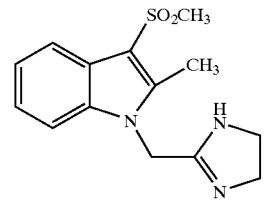

Step 1
(2-Methyl-1H-indol-3-yl)-dimethylsulfonium chloride

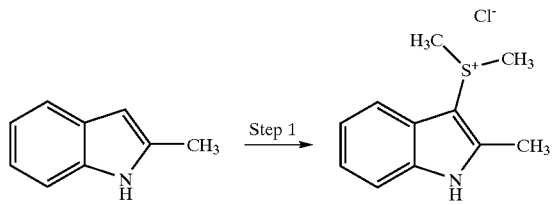

N-chlorosuccinimide (3.85 g, 29.35 mmole) was suspended in dichloroethane (40 ml) under a nitrogen atmosphere and cooled to −10° C. using an ice-salt-acetone bath. Dimethylsulfide (3 ml) was slowly added with stirring over a period of about 5 minutes. The mixture was stirred at this temperature for 10 minutes beyond the addition, at which time the ice-salt-acetone bath was replaced by a dry-ice acetone bath and the temperature was lowered to −50° C. To this solution was added 2-methylindole (3.85 g, 29.35 mmole) dissolved in dichloroethane (40 ml) slowly with stirring. The reaction mixture was stirred while allowing the temperature to reach 20° C. over about an hour. Diethyl ether (90 ml) was added with stirring and the precipitate which formed was filtered, washed well with ether, and dried overnight in a vacuum oven at room temperature. The free-flowing powder of (2-methyl-1H-indol-3-yl)-dimethylsulfonium chloride thus obtained was used without further purification in the following step.

Step 2
2-Methyl-3-methylsulfanyl-1H-indole

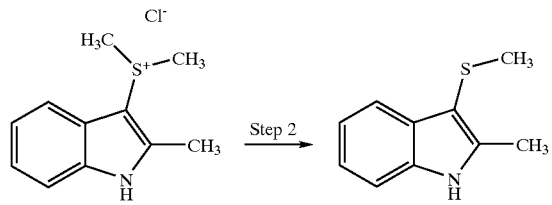

(2-Methyl-1H-indol-3-yl)-dimethylsulfonium chloride (2 g of the unpurified product from Step 1) was placed under vacuum in a flask connected to a tube and distillation bulb receiver and gently warmed with a heat gun until bubbling of gas commenced. The sample was heated intermittently until the bubbling ceased and no more product distilled over. The distillate was taken up in toluene and passed through a column of deactivated aluminum oxide (6% water added) and eluted with toluene. Evaporation of the solvent afforded 1.10 g of 2-methyl-3-methylsulfanyl-1H-indole.

Step 2a (Alternative Method for Decomposition of indol-3-ylsulfonium Salts to 3-alkylthioindoles)
7-Methoxy-3-methylsulfanyl-1H-indole

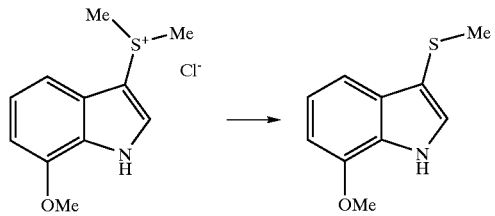

(7-Methoxy-1H-indol-3-yl)-dimethyl-sulfonium chloride (0.742 g) prepared in the manner described in Step 1 above was dissolved in DMSO (3 ml) and placed under reduced pressure (house vacuum, ca. 20–50 torr) in a round-bottom flask. The flask was placed on a steam bath and heated until the bubbling stopped. When no more starting material was present, the reaction mixture was cooled and partitioned between ether and water. The organic layer was dried and filtered and then evaporated to dryness to afford 7-methoxy-3-methylsulfanyl-1H-indole (0.514 g, 87.5%).

Similarly prepared was 3-ethylthio-6-chloroindole (0.867 g, 90.8% yield) from (6-chloro-1H-indol-3-yl)-diethyl-sulfonium chloride, 3-methylthio-6-methylindole (0.935 g, 69% yield after purification by column chromatography) from (6-methyl-1H-indol-3-yl)-dimethyl-sulfonium chloride, and 3-methylthio-5-methylindole (0.932 g, 76.6% yield after purification by column chromatography) from (5-methyl-1H-indol-3-yl)-dimethyl-sulfonium chloride.

Step 3
2-Methyl-3-methylsulfanyl-indol-1-yl)-acetonitrile

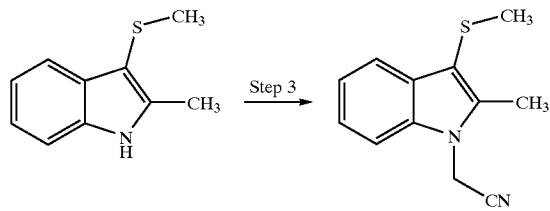

2-Methyl-3-methylsulfanyl-1H-indole (1.10 g, 6.21 mmole) was dissolved in toluene (25 ml). To this solution was added bromoacetonitrile (0.89 g, 7.42 mmole) and tetrabutylammonium bromide (1 g). With stirring, a solution of 4 g sodium hydroxide dissolved in 4 ml water was added. After 30 minutes another few drops of bromoacetonitrile were added in order to complete the reaction. After 30 minutes more, the stirring was stopped and the reaction was allowed to stand overnight at room temperature. The toluene layer was decanted onto a column of silica gel and the aqueous layer was extracted twice with toluene. The water layer was diluted with water and extracted once more with toluene. The combined toluene extracts were applied to the column and the product was eluted with ethyl acetate:hexane (3:7) to afford 1.05 g of an oil.

Step 4
(3-Methanesulfonyl-2-methyl-indol-1-yl)-acetonitrile

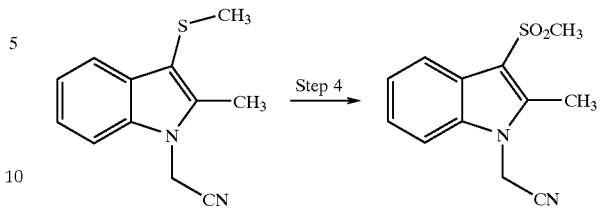

(2-Methyl-3-methylsulfanyl-indol-1-yl)-acetonitrile (1.05 g, 4.86 mmole) was dissolved in dichloromethane (50 ml) and cooled in an ice bath to 0° C. At this temperature m-chloroperoxybenzoic acid (ca. 77%, 2.4 g,) was added in portions. The ice bath was removed and the reaction mixture was allowed to reach room temperature while stirring for 1 h. The entire contents of the reaction flask was poured onto a column of deactivated aluminum oxide (6% water added) and the product was eluted using ethyl acetate:hexane (1:1). This afforded 1.01 g of (3-methanesulfonyl-2-methyl-indol-1-yl)-acetonitrile as a crystalline solid.

Step 5a
1-(4,5-Dihydro-1H-imidazol-2-ylmethyl)-3-methanesulfonyl-2-methyl-1H-indole

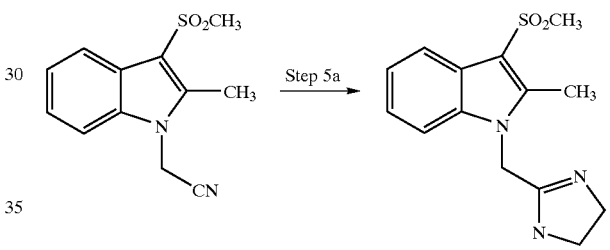

(3-Methanesulfonyl-2-methyl-indol-1-yl)-acetonitrile (0.5 g, 2.014 mmole) was mixed with ethylenediamine (2 ml) and 2 drops of carbon disulfide was added carefully. The flask was flushed with nitrogen and placed in an oil bath preheated to 150° C. The bath was maintained at 140–150° C. for a total of 75 minutes. The reaction mixture was then concentrated nearly to dryness under reduced pressure and the residue was taken up in dichloromethane and applied to a column of silica gel. A non-polar impurity was eluted with ethyl acetate, and then the product was eluted using a mixture of methylene chloride (130):methanol (10):ammonium hydroxide (1) to afford 520 mg pure crystalline product. The material was recrystallized from dichloromethane:ethyl acetate to provide 1-(4,5-dihydro-1H-imidazol-2-ylmethyl)-3-methanesulfonyl-2-methyl-1H-indole, mp:186.8–188.0° C.

Step 5b (Alternative Method for the Formation of the Imidazoline Ring): 1-(4,5-Dihydro-1H-imidazol-2-ylmethyl)-3-methanesulfonyl-6-methyl-1H-indole hydrochloride salt

-continued

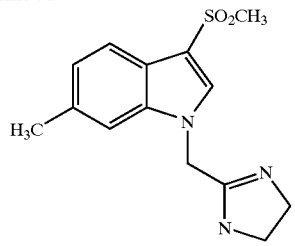

(3-Methanesulfonyl-6-methyl-indol-1-yl)-acetonitrile (0.4 g, 1.611 mmole) prepared from 6-methylindole as described in Steps 1–4 above, was added to ethylene diamine (4.3 ml, 438 mmole) in a reaction tube. A single drop of carbon disulfide was carefully added. The mixture was heated in a microwave reactor at 142° C. for 30 minutes. Upon cooling, the reaction mixture was poured into a mixture of ice and water, stirred 20 minutes and filtered. The colorless precipitate collected was washed with water (20 ml) and dried under vacuum at room temperature. The free base thus obtained (420 mg, 90% yield) was converted into the hydrochloride salt by first dissolving in methanol and then adding an excess of HCl in ethanol. The mixture was stripped to dryness and recrystallized from a mixture of ethyl acetate-methanol to afford 344 mg of 1-(4,5-dihydro-1H-imidazol-2-ylmethyl)-3-methanesulfonyl-6-methyl-1H-indole, mp >300° C. as the hydrochloride salt.

Similarly following the procedure of Example 1, but replacing the 2-methylindole in Step 1 with the appropriate indole derivatives, the following compounds were prepared:

5-chloro-1-(4,5-dihydro-1H-imidazol-2-ylmethyl)-3-methanesulfonyl-2-methyl-1H-indole, mp 211.7–215.3° C.;

4-chloro-1-(4,5-dihydro-1H-imidazol-2-ylmethyl)-3-methanesulfonyl-1H-indole, mp >300° C. as the hydrochloride salt;

1-(4,5-dihydro-1H-imidazol-2-ylmethyl)-7-ethyl-3-methanesulfonyl-1H-indole, mp 208.5–209.9° C.;

1-(4,5-dihydro-1H-imidazol-2-ylmethyl)-3-methanesulfonyl-5-methyl-1H-indole, mp 264–267° C. as the hydrochloride salt;

1-(4,5-dihydro-1H-imidazol-2-ylmethyl)-3-methanesulfonyl-2,5-dimethyl-1H-indole, mp 270.0–272.8° C. (dec) as the hydrochloride salt;

1-(4,5-dihydro-1H-imidazol-2-ylmethyl)-6-fluoro-3-methanesulfonyl-1H-indole, mp >300° C. as the hydrochloride salt;

6-bromo-1-(4,5-dihydro-1H-imidazol-2-ylmethyl)-3-methanesulfonyl-1H-indole;

5-bromo-1-(4,5-dihydro-1H-imidazol-2-ylmethyl)-3-methanesulfonyl-7-methyl-1H-indole;

1-(4,5-dihydro-1H-imidazol-2-ylmethyl)-5-(4-fluorophenyl)-3-methanesulfonyl-1H-indole;

5-benzyloxy-1-(4,5-dihydro-1H-imidazol-2-ylmethyl)-3-methanesulfonyl-1H-indole;

1-(4,5-Dihydro-1H-imidazol-2-ylmethyl)-3-methanesulfonyl-6-methyl-1H-indole;

1-(4,5-Dihydro-1H-imidazol-2-ylmethyl)-3-methanesulfonyl-4-methoxy-1H-indole;

7-Bromo-1-(4,5-dihydro-1H-imidazol-2-ylmethyl)-3-methanesulfonyl-2-methyl-1H-indole; and 1-(4,5-Dihydro-1H-imidazol-2-ylmethyl)-3-methanesulfonyl-7-methoxy-1H-indole.

Similarly following the procedure of Example 1, using the appropriate indoles but replacing in step 1 dimethyl sulfide with diethyl sulfide the following compounds were prepared:

5-chloro-1-(4,5-dihydro-1H-imidazol-2-ylmethyl)-3-ethanesulfonyl-1H-indole, mp 194.6–197° C. dec; and 6-chloro-1-(4,5-dihydro-1H-imidazol-2-ylmethyl)-3-ethanesulfonyl-1H-indole.

Similarly following the procedure of Example 1 but replacing 2-methylindole in step 1 with the appropriate indole derivatives, and replacing bromoacetonitrile in step 3 with the appropriate acetonitrile derivative, the following compounds were prepared:

1-[1-(4,5-dihydro-1H-imidazol-2-yl)-ethyl]-3-methanesulfonyl-2-methyl-1H-indole, mp 207–208° C.;

1-[1-(4,5-dihydro-1H-imidazol-2-yl)-ethyl]-3-methanesulfonyl-1H-indole, mp 202–203° C.; and 5-Chloro-1-[1-(4,5-dihydro-1H-imidazol-2-yl)-ethyl]-3-methanesulfonyl-2-methyl-1H-indole, mp 207–217° C. (dec);

Similarly following the procedure of Example 1 but replacing 2-methylindole in step 1 with the appropriate indole derivatives, and replacing ethylenediamine with propylenediamine in step 5a or step 5b, the following compounds were prepared:

3-methanesulfonyl-2-methyl-1-(1,4,5,6-tetrahydro-pyrimidin-2-ylmethyl)-1H-indole, mp 176–181° C. (dec.), and 3-methanesulfonyl-1-[1-(1,4,5,6-tetrahydro-pyrimidin-2-yl)-ethyl]-1H-indole, mp 270.5–271.4° C., as the hydrochloride salt.

Example 2

1-(4,5-Dihydro-1H-imidazol-2-ylmethyl)-3-methanesulfonyl-7-methyl-1H-indole

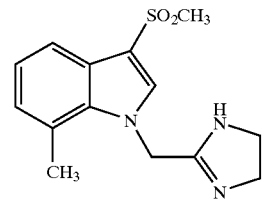

Step 1

7-Methyl-3-methanesulfonyl-1H-indole

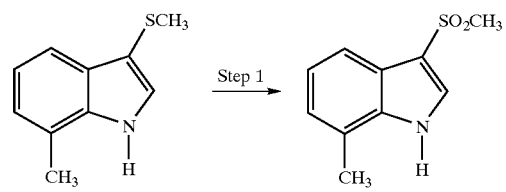

7-Methyl-3-methylsulfanyl-1H-indole (3.0 g, 16.9 mmole) prepared from 6-methylindole as described above in Example 1 Steps 1 and 2, was dissolved in ether (250 ml) and treated with m-chloroperoxybenzoic acid (ca. 77%, 8.48 g) in ether (100 ml). The reaction mixture was stirred at room temperature for 1 h and worked up by evaporation to dryness. The residue was partitioned between ethyl acetate and 10% sodium thiosulfate solution. The organic layer was washed with 10% sodium carbonate solution, dried over magnesium sulfate, and evaporated to dryness to afford 7-methyl-3-methane-sulfonyl-1H-indole (2.14 g).

Step 2
1-(4,5-Dihydro-1H-imidazol-2-ylmethyl)-3-methanesulfonyl-7-methyl-1H-indole

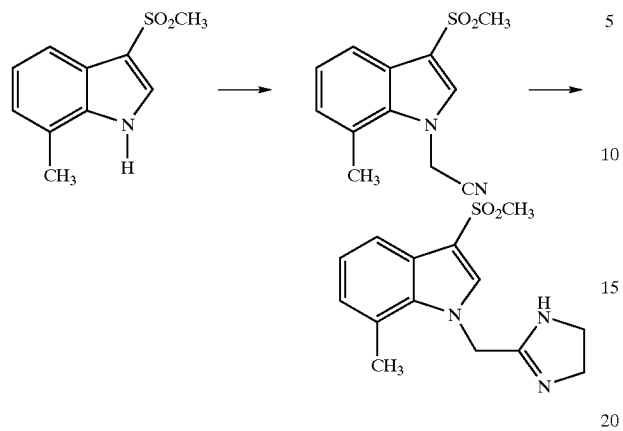

3-Methanesulfonyl-7-methyl-1H-indole (1.0 g, 4.78 mmole) was dissolved in anhydrous dimethylformamide (10 ml) and cooled to 0° C. in a nitrogen atmosphere. With stirring, sodium hydride (60% in oil, 229 mg, 5.72 mmole) was added all at once and the mixture was stirred at this temperature until no more bubbles evolved (ca. 20–30 minutes). Bromoacetonitrile (630 mg, 5.25 mmole) was then added to the reaction mixture which was then allowed to warm to room temperature over the next hour. The mixture was partitioned between water and ethyl acetate and the organic layer was washed three times with water, dried over magnesium sulfate, filtered and evaporated to dryness. The crude residue was purified on a silica gel column eluting with hexane-ethyl acetate mixtures (30:70 to 50:50) to afford. 1.116 g of pure (3-methanesulfonyl-7-methyl-indol-1-yl)-acetonitrile. Following the procedure described above in Example 1 Step 5a, the acetonitrile derivative was converted with ethylenediamine into 1-(4,5-dihydro-1H-imidazol-2-ylmethyl)-3-methanesulfonyl-7-methyl-1H-indole, mp 214–215° C.

Similarly following the procedure of Example 2, the following compounds were prepared:

1-(4,5-dihydro-1H-imidazol-2-ylmethyl)-5-fluoro-3-methanesulfonyl-1H-indole, mp 203–205° C.;
1-(4,5-dihydro-1H-imidazol-2-ylmethyl)-3-methanesulfonyl-5-methoxy-1H-indole, mp 162–165° C.;
1-(4,5-dihydro-1H-imidazol-2-ylmethyl)-3-methanesulfonyl-5-nitro-1H-indole, mp 224–229° C.;
7-bromo-1-(4,5-dihydro-1H-imidazol-2-ylmethyl)-3-methanesulfonyl-1H-indole, mp 254–258° C.
5-bromo-1-(4,5-dihydro-1H-imidazol-2-ylmethyl)-3-methanesulfonyl-1H-indole, mp 218–220° C.; and
7-chloro-1-(4,5-dihydro-1H-imidazol-2-ylmethyl)-3-methanesulfonyl-1H-indole, mp 253–257° C.

Similarly following the procedure of Example 2, but replacing ethylenediamine with propylenediamine in step 2, 5-bromo-3-methanesulfonyl-1-(1,4,5,6-tetrahydro-pyrimidin-2-ylmethyl)-1H-indole, mp 188–191° C.

1-(4,5-Dihydro-1H-imidazol-2-ylmethyl)-3-methanesulfonyl-1H-indol-5-ylamine, (mp 215–217° C.) was prepared by reduction of the nitro group of compound 1-(4,5-dihydro-1H-imidazol-2-ylmethyl)-3-methanesulfonyl-5-nitro-1H-indole, with $TiCl_3$ in aqueous acetonitrile.

N-1-(4,5-dihydro-1H-imidazol-2-ylmethyl)-3-methanesulfonyl-1H-indol-5-yl]-methanesulfonamide, mp 232–233° C., was prepared from 1-(4,5-Dihydro-1H-imidazol-2-ylmethyl)-3-methanesulfonyl-1H-indol-5-ylamine by treatment with methane sulfonylchloride and pyridine.

Example 3
6-Chloro-1-(4,5-dihydro-1H-imidazol-2-ylmethyl)-3-methanesulfonyl-1H-indole

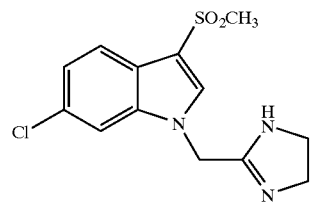

Step 1
6-Chloro-3-methanesulfonyl-1H-indole

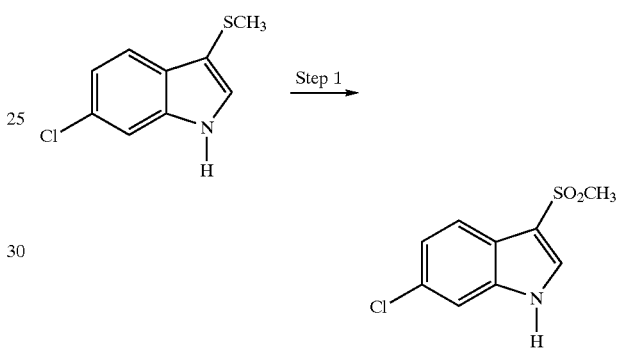

6-Chloro-3-methylsulfanyl-1H-indole (1.33 g, 6.7 mmole) was dissolved in dichloromethane (25 ml) and treated with m-chloroperoxybenzoic acid (ca. 77%, 3.33 g, ca. 14.8 mmole) in dichloromethane (25 ml). The reaction mixture was stirred at room temperature for 1 h and worked up by evaporation to dryness. The residue was partitioned between ethyl acetate and 10% sodium thiosulfate solution. The organic layer was washed with 10% sodium carbonate solution, dried over magnesium sulfate, and evaporated to dryness to afford the pure sulfone (1.501 g).

Step 2
(6-Chloro-3-methanesulfonyl-indol-1-yl)-acetic acid ethyl ester

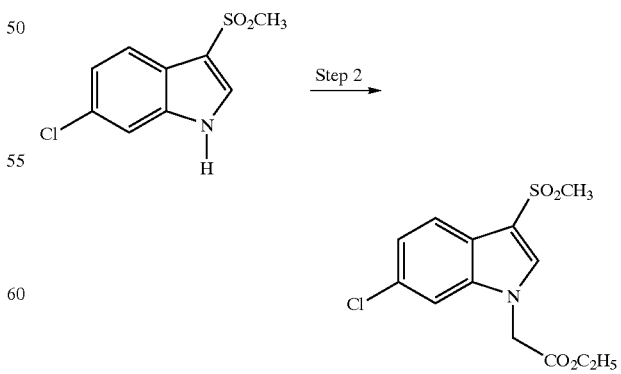

6-Chloro-3-methanesulfonyl-1H-indole (1.35 g, 5.88 mmole) was dissolved in anhydrous N-methylpyrrolidin-2-one (15 ml), cooled to 0° C. and placed under a nitrogen atmosphere. Sodium hydride (60% in oil, 0.28 g, 7 mmole) was added all at once and the mixture was stirred until the evolution of gas ceased (ca. 20–30 minutes). Ethyl bromoacetate (1.08 g, 6.47 mmole) was added all at once and the mixture was stirred for 30 minutes. The reaction mixture was partitioned between ethyl acetate and water, the organic layer was washed three times with water, dried over magnesium sulfate, filtered, and evaporated to dryness. The crude material thus obtained was purified by chromatography on silica gel, eluting with ethyl acetate-hexane (1:9) to (4:6) to afford 1.463 g of (6-chloro-3-methanesulfonyl-indol-1-yl)-acetic acid ethyl ester.

Step 3

6-Chloro-1-(4,5-dihydro-1H-imidazol-2-ylmethyl)-3-methanesulfonyl-1H-indole

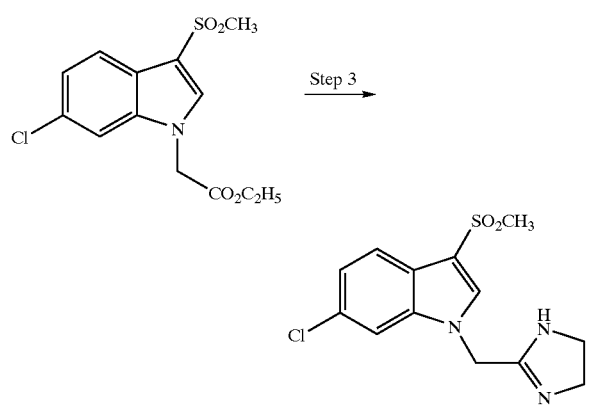

Trimethylaluminum (3.95 ml, 2.0 m in toluene) was added to 5 ml anhydrous toluene and cooled to 0° C. in a nitrogen atmosphere. Ethylenediamine (0.48 g) was added dropwise slowly. The resulting mixture was stirred for 25 minutes at 0° C. (6-Chloro-3-methanesulfonyl-indol-1-yl)-acetic acid ethyl ester (0.5 g) dissolved in anhydrous toluene (20 ml) was added all at once and the reaction mixture was brought to reflux. After heating overnight at reflux, the mixture was cooled. Several grams of sodium sulfate decahydrate was added and the mixture was stirred for 30 minutes. Methanol was added to this mixture which was filtered and the precipitate was washed well with methanol. The crude material thus obtained was purified by chromatography as follows. The material was taken up in dichloromethane and applied to a column of silica gel. Elution of the product was accomplished by elution first with methylene chloride (130):methanol (10):ammonium hydroxide (1) and then with methylene chloride (60):methanol (10):ammonium hydroxide (1). The crystalline 6-chloro-1-(4,5-dihydro-1H-imidazol-2-ylmethyl)-3-methanesulfonyl-1H-indole, 31 weighed 446 mg, mp: 211.7–213° C.

Similarly following the procedure of Example 3, but replacing 6-chloro-3-methylsulfanyl-1H-indole with the appropriate indole in Step the following compounds were prepared:

1-(4,5-dihydro-1H-imidazol-2-ylmethyl)-3-methanesulfonyl-1H-indole, mp 174.5–175.8° C.; and 5-chloro-1-(4,5-dihydro-1H-imidazol-2-ylmethyl)-3-methanesulfonyl-1H-indole, mp 217.4–218.9° C.

Example 4

7-Chloro-1-(4,5-dihydro-1H-imidazol-2-ylmethyl)-3-methanesulfonyl-2-methyl-1H-indole

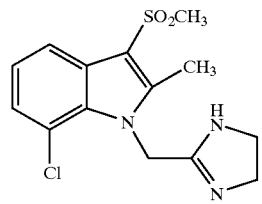

Step 1:
7-Chloro-2-methyl-3-methylsulfanyl-1H-indole

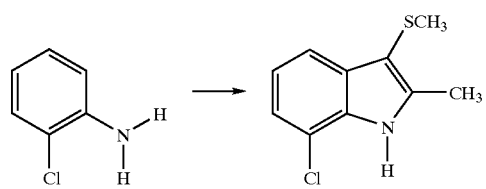

Using the procedure described in *J. Amer. Chem. Soc.*, 1974, 96 (17) 5495, 2-chloroaniline (1.27 g, 10 mmole) was dissolved in dichloromethane (35 ml) and cooled to −65° C. To this solution was added dropwise with vigorous stirring, t-butyl hypochlorite (1.08 g, 10 mmole) in dichloromethane (5 ml). After 10 minutes 1-methylsulfanyl-propan-2-one (1.04 g, 10 mmole) dissolved in dichloromethane (5 ml) was added. The mixture was stirred at −65° C. for 1 h more. At this point triethylamine (1.01 g, 10 mmole) dissolved in dichloromethane (5 ml) was added. Upon completion of the addition, the reaction mixture was allowed to reach ambient temperature. Water was added and the layers were separated, the organic layer was dried over magnesium sulfate, filtered and the solvent evaporated to dryness. The residue was purified by column chromatography on silica gel using a mixture of hexane-ethyl acetate (95:5) to elute 7-chloro-2-methyl-3-methylsulfanyl-1H-indole (1.94 g) as an oil.

Step 1a (Alternative Method for Preparation for 2-Unsubstituted Indoles)

7-Chloro-5-fluoro-3-methylsulfanyl-1H-indole

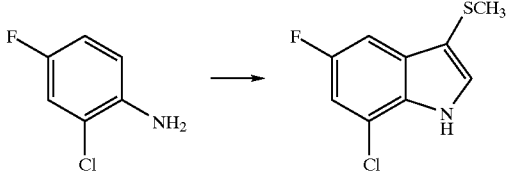

Following the procedure described in J.Amer.Chem.Soc. 96 (17), 5495 (1974) 2-chloro-4-fluoroaniline (1.45 g, 10 mmole) was dissolved in methylene chloride (35 ml) and stirred vigorously at −65° C. under nitrogen while freshly prepared t-butyl hypochlorite (1.08 g, 10 mmole) dissolved in 10 ml methylene chloride was added dropwise. Ten minutes after the completion of the addition a solution of 1,1-dimethoxy-2-methylsulfanyl-ethane (1.36 g, 10 mmole) dissolved in 10 ml methylene chloride was added slowly. The reaction mixture was stirred at −65° C. for 1 h after which time, triethyl amine (1.01 g, 10 mmole) dissolved in 10 ml methylene chloride was added and the temperature was allowed to rise to room temperature. Water was added and the organic layer was separated, dried over magnesium sulfate, filtered and evaporated to dryness. The oily residue was taken up in carbon tetrachloride (35 ml) containing triethylamine (2 ml) and refluxed overnight. The solvent was removed and replaced with ether (35 ml) and stirred in a two-phase system with 12 ml of 2N HCl for about 3 h. The ether layer was then separated, washed with bicarbonate solution, dried over magnesium sulfate, filtered and evaporated to dryness. Purification by chromatography on silica gel (1:9 ethyl acetate:hexane) afforded the pure 7-chloro-5-fluoro-3-methylsulfanyl-1H-indole (0.997 g, 46% yield).

Similarly prepared was 7-trifluoromethyl-3-methylsulfanyl-1H-indole (0.867 g, 37% yield) from 2-trifluoromethyl aniline (1.61 g). Instead of the two-phase acid-catalyzed cyclization described above, cyclization was instead effected by refluxing in methanol for 12 h.

Steps 2–4
7-Chloro-1-(4,5-dihydro-1H-imidazol-2-ylmethyl)-3-methanesulfonyl-2-methyl-1H-indole

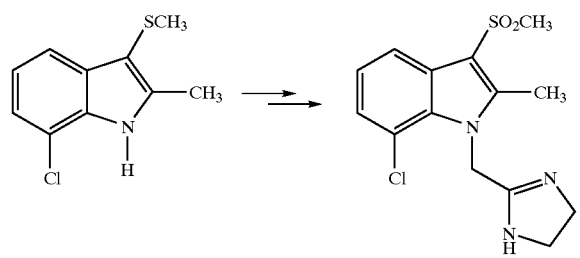

Following Steps 1 and 2 of Example 2, the methylsulfanyl compound was oxidized, treated with bromoacetonitrile and reacted with ethylenediamine to afford 7-chloro-1-(4,5-dihydro-1H-imidazol-2-ylmethyl)-3-methanesulfonyl-2-methyl-1H-indole, mp 221–223° C.

Similarly following the above procedure of Example 4, the following compound was prepared:

1-(4,5-dihydro-1H-imidazol-2-ylmethyl)-7-fluoro-3-methanesulfonyl-2-methyl-1H-indole, mp 206–208° C.

Steps 2–4a (Alternative Method for Preparation for 2-Unsubstituted Indoles)
7-Chloro-1-(4,5-dihydro-1H-imidazol-2-ylmethyl)-5-fluoro-3-methanesulfonyl-1H-indole

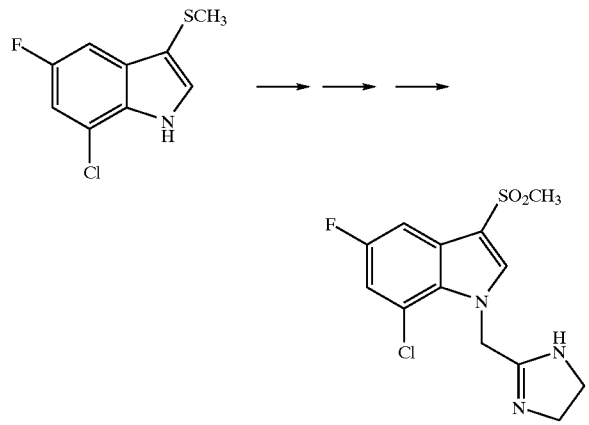

Transformation of 7-chloro-5-fluoro-3-methylsulfanyl-1H-indole to 7-chloro-1-(4,5-dihydro-1H-imidazol-2-ylmethyl)-5-fluoro-3-methanesulfonyl-1H-indole was accomplished according to Steps 3–5 of Example 1, or by Steps 1–2 of Example 2 as described above Likewise, using the procedure of Example 4, the following were prepared:

7-Chloro-1-(4,5-dihydro-1H-imidazol-2-ylmethyl)-3-ethanesulfonyl-2-methyl-1H-indole;

1-(4,5-Dihydro-1H-imidazol-2-ylmethyl)-3-methanesulfonyl-6-methoxy-2-methyl-1H-indole;

1-(4,5-Dihydro-1H-imidazol-2-ylmethyl)-3-methanesulfonyl-4-methoxy-2-methyl-1H-indole;

5-bromo-1-(4,5-dihydro-1H-imidazol-2-ylmethyl)-3-methanesulfonyl-2-methyl-1H-indole;

1-(4,5-dihydro-1H-imidazol-2-ylmethyl)-3,6-bis-methanesulfonyl-2-methyl-1H-indole;

1-(4,5-dihydro-1H-imidazol-2-ylmethyl)-3,4-bis-methanesulfonyl-2-methyl-1H-indole;

1-(4,5-Dihydro-1H-imidazol-2-ylmethyl)-3,5-bis-methanesulfonyl-2-methyl-1H-indole;

7-chloro-1-(4,5-dihydro-1H-imidazol-2-ylmethyl)-5-fluoro-3-methanesulfonyl-2-methyl-1H-indole;

1-(4,5-dihydro-1H-imidazol-2-ylmethyl)-3-methanesulfonyl-7-trifluoromethyl-1H-indole; and 1-(4,5-Dihydro-1H-imidazol-2-ylmethyl)-3-methanesulfonyl-2-methyl-7-trifluoromethyl-1H-indole.

Example 5

2-(7-Chloro-3-methanesulfonyl-indol-1-ylmethyl)-4,5-dihydro-3H-imidazol-1-ium chloride

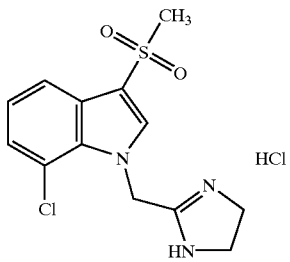

Step 1
2-Chloro-6-methylsulfanylmethyl-phenylamine

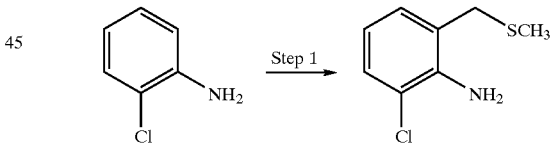

2-Chloro-phenylamine (12.76 g, 0.1 mole) and dimethyl sulfide (10 ml) were dissolved in dichloroethane (200 ml) and cooled in an ice-acetone-salt bath under a nitrogen atmosphere. N-chlorosuccinimide (14.70 g, 0.11 mole) dissolved in dichloroethane (300 ml) was slowly added via addition funnel over about 20–30 minutes. After stirring an hour beyond addition while allowing the reaction to reach room temperature, triethyl amine (30 ml) was added and the mixture was brought to reflux for 1 h and 20 minutes. The reaction was monitored by tlc (15:85 EtOAc:hexane on silica gel) which showed a single less polar product. The mixture was cooled and evaporated to dryness. The residue was taken up in methylene chloride, dry packed on silica gel, and placed onto a column of flash silica gel. The product was eluted from the column with 1:9 ethyl acetate:hexane to give 15.4 g of a homogeneous oil (82%), 2-chloro-6-methylsulfanylmethyl-phenylamine.

Step 2
N-(2-Chloro-6-methylsulfanylmethyl-phenyl)-2,2,2-trifluoro-acetamide

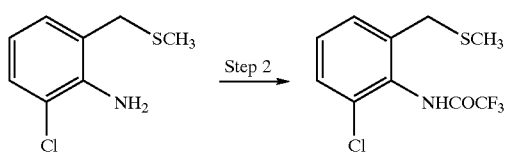

2-chloro-6-methylsulfanylmethyl-phenylamine (15.4 g, 0.082 mole) from Step 1 was dissolved in methylene chloride (200 ml) and trifluoroacetic anhydride (21.54 g, 0.102 mole, 14.5 ml) was added slowly with stirring while cooling the reaction mixture in ice. After standing for 30 m at room temperature, the solvent and excess reagent were evaporated to dryness under reduced pressure. The resulting solid N-(2-chloro-6-methylsulfanylmethyl-phenyl)-2,2,2-trifluoro-acetamide weighed 22.35 g (96%) and was used without further purification.

Step 3
N-(2-Chloro-6-methanesulfonylmethyl-phenyl)-2,2,2-trifluoro-acetamide

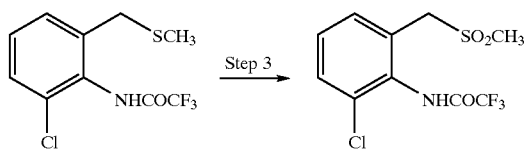

The crude solid N-(2-chloro-6-methylsulfanylmethyl-phenyl)-2,2,2-trifluoro-acetamide from Step 2 was redissolved in methylene chloride (300 ml) and treated at 0° C. with meta-chloroperoxybenzoic acid (39.88 g, 0.177 mole) in portions with stirring. After 90 minutes the entire reaction mixture was poured onto a column of deactivated aluminum oxide (6% water) and the product was washed free of the acid by eluting with 1:1 ethyl acetate:hexane to afford 22.28 g of N-(2-Chloro-6-methanesulfonylmethyl-phenyl)-2,2,2-trifluoro-acetamide, a crystalline product (86%).

Step 4
2-Chloro-6-methanesulfonylmethyl-phenylamine

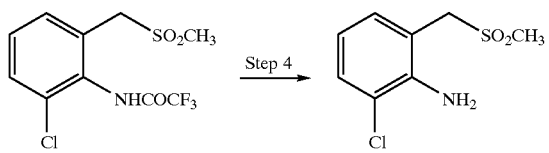

The crystalline N-(2-Chloro-6-methanesulfonylmethyl-phenyl)-2,2,2-trifluoro-acetamide of Step 3 was taken up into 200 ml of 2N solution of sodium hydroxide and stirred and heated in an oil bath heated to 120° C. The homogeneous solution was stirred at this temperature for 90 minutes and slowly allowed to cool to room temperature. The flask was immersed in an ice bath and the suspension of the product was stirred at this temperature until all was crystalline. Filtration, washing well with water and thorough drying afforded 13.96 g of pure crystalline 2-chloro-6-methanesulfonylmethyl-phenylamine (90%).

Step 5
N-(2-Chloro-6-methanesulfonylmethyl-phenyl)-formimidic acid methyl ester

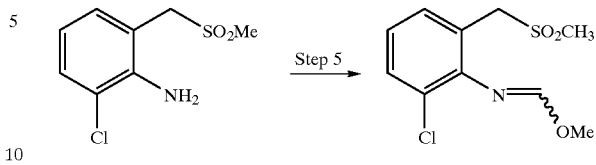

The 2-chloro-6-methanesulfonylmethyl-phenylamine (2.04 g, 0.019 mole) of Step 4 was suspended in 15 ml trimethyl orthoformate and p-toluenesulfonic acid hydrate (0.21 g) was added. The reaction mixture was brought to reflux and heated at this temperature for 3 h. The reaction was monitored by tlc (3:7 ethyl acetate:hexane, silica gel) which showed the appearance of a new slightly less polar spot. At the end of 3 h, the reaction was cooled and evaporated to dryness to afford N-(2-Chloro-6-methanesulfonylmethyl-phenyl)-formimidic acid methyl ester.

Step 6
7-Chloro-3-methanesulfonyl-1H-indole

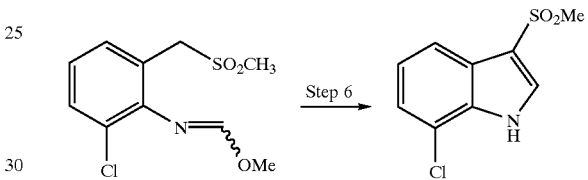

The crude N-(2-chloro-6-methanesulfonylmethyl-phenyl)-formimidic acid methyl ester of Step 5 was dissolved in dry DMSO (20 ml) and treated with 2 g powdered sodium hydroxide. The reaction mixture was vigorously stirred at room temperature for 1 h after which tlc (1:1 ethyl acetate:hexane, followed by 3:7) showed a single principal product, somewhat less polar than starting material. The reaction mixture was diluted with 100 ml of a 10% ammonium chloride solution and extracted with ethyl acetate, washed twice with water, and the crude solution was passed through a short silica gel column and eluted with ethyl acetate to remove colored impurities. The resulting crystalline 7-chloro-3-methanesulfonyl-1H-indole weighed 2.21 g.

Step 7
(7-Chloro-3-methanesulfonyl-indol-1-yl)-acetonitrile

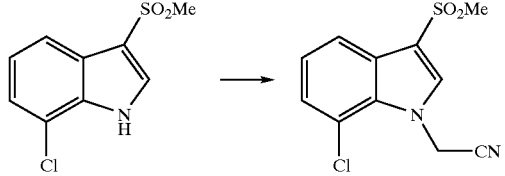

The 7-chloro-3-methanesulfonyl-1H-indole (2.21 g, 0.00962 mole) of Step 6 was dissolved in 20 ml dry N-methylpyrrolidinone and cooled to 0° C. under a nitrogen atmosphere. Sodium hydride (60% in oil, 0.46 g, 0.0115 mole) was added in portions with stirring and the reaction mixture was allowed to stir until bubbling ceased. Bromoacetonitrile (1.27 g, 0.0106 mole) was added all at once and the resulting solution was stirred and allowed to reach room temperature. After 1 h, the reaction mixture was poured into water-ethyl acetate and the organic layer was washed three times with brine and dried over magnesium sulfate. Evaporation to dryness gave a residue of 3.31 g which was purified by flushing through an alumina (6% water) column using 3:7 and 1:1 ethyl acetate-hexane to elute the product. The purified (7-chloro-3-methanesulfonyl-indol-1-yl)-acetonitrile was crystalline and weighed 2.111 g after thoroughly drying.

Step 8
7-Chloro-1-(4,5-dihydro-1H-imidazol-2-ylmethyl)-3-methanesulfonyl-1H-indole

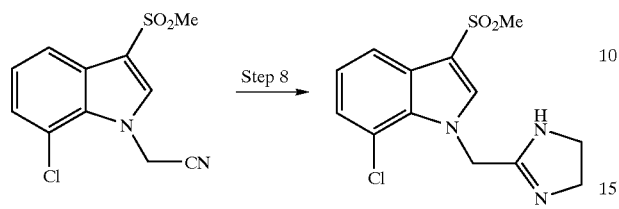

(7-chloro-3-methanesulfonyl-indol-1-yl)-acetonitrile (2.1 g) from Step 7 was dissolved in ethylene diamine (10 ml) and 2 drops of carbon disulfide were added. The flask was blanketed with nitrogen and then placed in an oil bath previously heated to 140° C. The mixture was stirred and after 30 minutes checked by mass spec which revealed the complete absence of starting material and the appearance of the desired product (positive ion spectrum) as well as an undetermined amount of unalkylated impurity from the previous reaction (negative ion spectrum). After 45 minutes, the reaction was cooled to room temperature and then placed in an ice bath. The product crystallized. Ethyl acetate (10 ml) was added and the precipitate was broken up, filtered, and then washed with a bit of ethyl acetate followed by ether. Air drying gave 1.22 g of a colorless crystalline solid, 7-chloro-1-(4,5-dihydro-1H-imidazol-2-ylmethyl)-3-methanesulfonyl-1H-indole which after vacuum drying overnight at 60° C. weighed 1.21 g. The material was analytically pure.

Step 9
2-(7-Chloro-3-methanesulfonyl-indol-1-ylmethyl)-4,5-dihydro-3H-imidazol-1-ium chloride

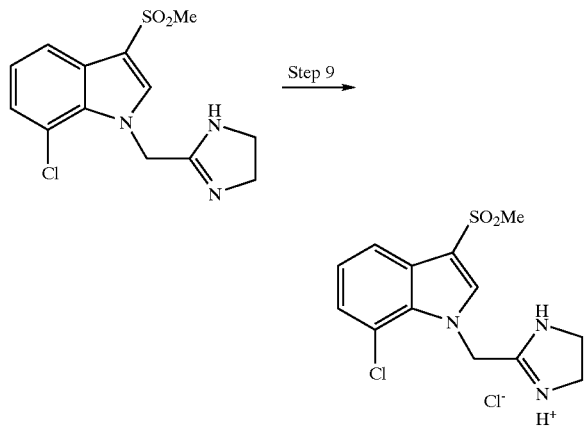

7-chloro-1-(4,5-dihydro-1H-imidazol-2-ylmethyl)-3-methanesulfonyl-1H-indole (1.21 g) from Step 8 was dissolved in methylene chloride and treated with an excess of 1N HCl in ethanol and evaporated to dryness. The resulting crystalline solid was slurried with ethyl acetate and broken up, and then filtered. The filter cake was washed first with ethyl acetate, then with ether, and dried under vacuum at 60° C. overnight. The resulting material weighed 1.34 g (99%) and was analytically pure.

Using the above procedure, but replacing trimethyl orthoformate with trimethyl orthobutyrate in step 5,5-chloro-1-(4,5-dihydro-1H-imidazol-2-ylmethyl)-3-methanesulfonyl-2-propyl-1H-indole was prepared.

Example 6

1-(4,5-Dihydro-1H-imidazol-2-ylmethyl)-1H-indole-3-sulfonic acid dimethylamide

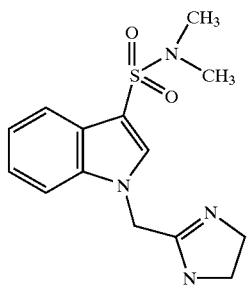

Step 1
N,N-Dimethyl-C-(2-nitro-phenyl)-methanesulfonamide

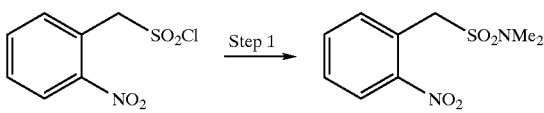

2-Nitro-α-toluenesulfonyl chloride (0.943 g, 4.0 mmole) was dissolved in dry dioxane (7 ml) and treated with a solution of dimethylamine (4 ml 2M solution in THF, 8.0 mmole), and stirred at room temperature for a total of 6 h. The reaction mixture was transferred to a separatory funnel and partitioned between ethyl acetate and water. The organic solution was washed with brine, dried over magnesium sulfate, filtered and evaporated to dryness to afford the pure 2-nitrobenzyl-N,N-dimethylsulfonamide, 0.829 g (85% yield).

Step 2
2-Aminobenzyl-N,N-dimethylsulfonamide

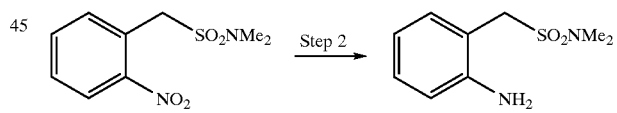

The 2-nitrobenzyl-N,N-dimethylsulfonamide (0.825 g, 3.377 mmole) of Step 1 was dissolved/suspended in alcohol in a Parr hydrogenation bottle. Palladium on charcoal (90 mg, 10% Pd) was added and the mixture was placed under an atmosphere of hydrogen at 45 psi in a Parr shaker. After shaking overnight, the mixture was filtered through Celite and evaporated to dryness to afford 0.693 g pure 2-aminobenzyl-N,N-dimethylsulfonamide (96% yield).

Step 3
C-[2-(Dimethylamino-methyleneamino)-phenyl]-N,N-dimethyl-methanesulfonamide

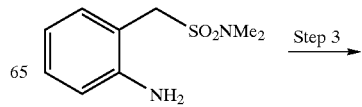

-continued

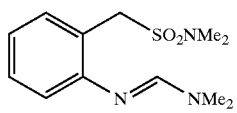

Dimethylformamide (20 ml) was cooled under a nitrogen atmosphere to −40° C. in a dry ice-acetonitrile bath. Oxalyl chloride (2 ml) was added dropwise at such a rate as to maintain the temperature below −30° C. Upon completion of the addition, the suspension was allowed to rise to room temperature. After about an hour, 2-aminobenzyl-N,N-dimethylsulfonamide (0.630 g) dissolved in DMF (5 ml) was added with stirring and the reaction mixture was stirred at room temperature for 4 h. The solution was partitioned between 1% sodium hydroxide solution and ethyl acetate. The organic layer was dried over magnesium sulfate, filtered and evaporated to dryness to afford C-[2-(dimethylamino-methyleneamino)-phenyl]-N,N-dimethyl-methanesulfonamide as an oil which was used directly in the next step.

Step 4
1H-Indole-3-sulfonic acid dimethylamide

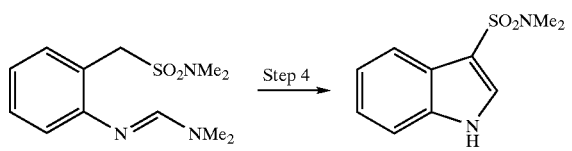

The crude product from Step 3 was dissolved in DMF (7 ml) and to this solution was added sodium hydride (60% in oil, 0.353 g, 8.82 mmole) in portions under a nitrogen atmosphere. After the initial bubbling subsided, the temperature was raised to 40° C. and left at that temperature overnight. Tlc analysis of the reaction mixture showed the presence of starting material and thus the temperature was raised to 60° C. and heated another 24 h. After cooling the reaction mixture was partitioned between 1.5 M HCl and ethyl acetate. The organic layer was separated and washed with bicarbonate solution, and then with brine. After drying over magnesium sulfate and filtration, the solvent was removed under reduced pressure to afford 0.547 g of the crude product. Purification by column chromatography (silica gel, 5:95 ethyl acetate:methylene chloride) afforded 0.437 g of the pure 1H-Indole-3-sulfonic acid dimethylamide (66% yield).

Step 5
1-Cyanomethyl-1H-indole-3-sulfonic acid dimethylamide

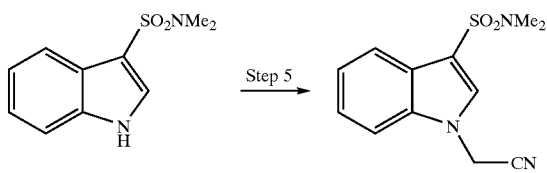

Step 5 was carried out in a manner similar to Example 2, Step 2, on 0.114 g 1H-Indole-3-sulfonic acid dimethylamide to afford 0.125 g (93% yield) of 1-cyanomethyl-1H-indole-3-sulfonic acid dimethylamide.

Step 6
1-(4,5-Dihydro-1H-imidazol-2-ylmethyl)-1H-indole-3-sulfonic acid dimethylamide

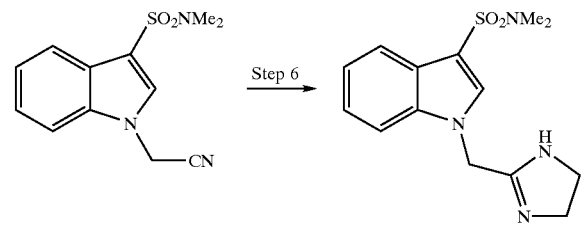

Step 6 was carried out in a manner similar to Example 1, step 5b on 0.100 g of 1-cyano-methyl-1H-indole-3-sulfonic acid dimethylamide to afford 0.097 g (83%) of pure 1-(4,5-dihydro-1H-imidazol-2-ylmethyl)-1H-indole-3-sulfonic acid dimethylamide.

Similarly, using the procedure of Example 6, the following were prepared: 1-(4,5-Dihydro-1H-imidazol-2-ylmethyl)-1H-indole-3-sulfonic acid diallylamide; and 5-Chloro-1-(4,5-dihydro-1H-imidazol-2-ylmethyl)-1H-indole-3-sulfonic acid dimethylamide.

Example 7

2-[5-Chloro-1-(4,5-dihydro-1H-imidazol-2-ylmethyl)-1H-indole-3-sulfonyl]-ethanol

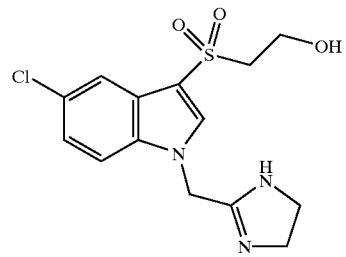

Step 1
2-(5-chloro-1H-indol-3-yl)-isothiouronium iodide.

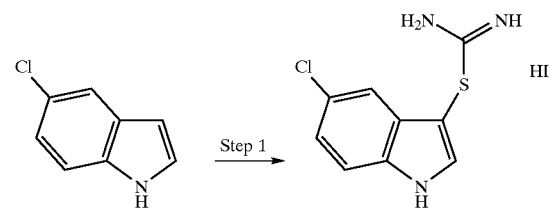

Following the procedure of J. Med Chem 1983, 26, 230–237, 5-Chloroindole (1.0 g, 6.6 mmole) and thiourea (0.503 g, 6.6 mmole) were dissolved in methanol (10 ml) and treated with a solution of iodine (1.524 g, 6.0 mmole) and potassium iodide (1.1 g, 6.6 mmole) in water (6.6 ml). The mixture was allowed to stir overnight.

The reaction mixture was evaporated to dryness and the residue was treated with ethyl acetate and filtered from residual potassium iodide. Repeated trituration of the dark residual solid with ether afforded a light yellow crystalline solid, 2.27 g of 2-(5-chloro-1H-indol-3-yl)-isothiouronium iodide.

Step 2
5-Chloro-3-[2-(tetrahydro-pyran-2-yloxy)-ethylsulfanyl]-1H-indole

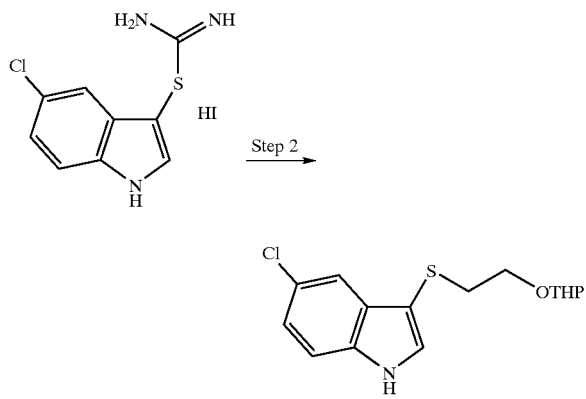

2-(5-chloro-1H-indol-3-yl)-isothiouronium iodide (0.70 g, 1.98 mmole) from Step 1 was dissolved in water (20 ml) and treated with 2M sodium hydroxide (2.97 ml) dropwise, after which the solution was heated at 90° C. for 30 minutes under nitrogen. The mixture was cooled to room temperature and tetrabutylammonium bromide (0.287 g, 0.89 mmole) was added followed by toluene (24 ml). To the resulting two phase system was added 2-(2-Bromo-ethoxy)-tetrahydropyran (0.435 g, 2.08 mmole). The mixture was vigorously stirred for three hours. The toluene layer was separated and without further workup was filtered through a short column of aluminum oxide deactivated by the addition of water (3%), using methylene chloride as the eluting solvent. The 5-chloro-3-[2-(tetrahydro-pyran-2-yloxy)-ethylsulfanyl]-1H-indole obtained after the evaporation of the solvent weighed 0.46 g and was carried on to the next experiment without further purification.

Step 3
{5-Chloro-3-[2-(tetrahydro-pyran-2-yloxy)-ethylsulfanyl]-indol-1-yl}-acetonitrile

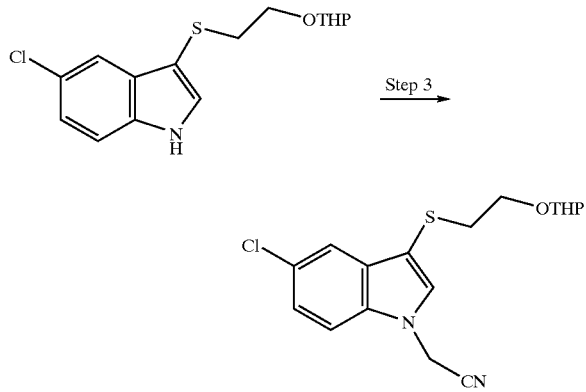

Using the procedure of Example 1, Step 3, {5-chloro-3-[2-(tetrahydro-pyran-2-yloxy)-ethylsulfanyl]-indol-1-yl}-acetonitrile (0.301 g, 61% yield) was prepared from 0.440 g of 5-chloro-3-[2-(tetrahydro-pyran-2-yloxy)-ethylsulfanyl]-1H-indole.

Step 4
{5-Chloro-3-[2-(tetrahydro-pyran-2-yloxy)-ethanesulfonyl]-indol-1-yl}-acetonitrile

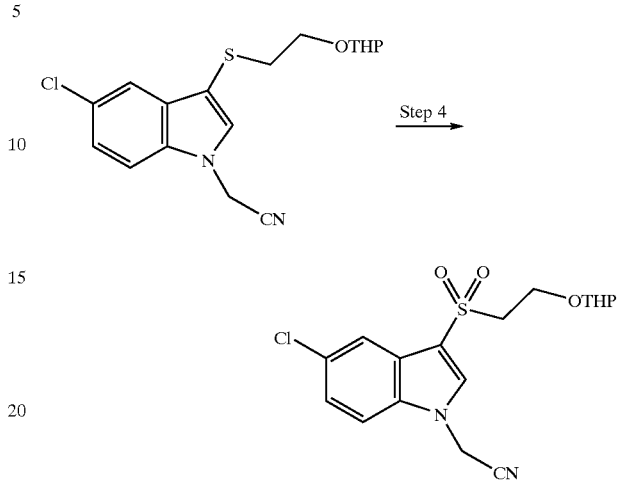

Using the procedure of Example 1, Step 4, {5-Chloro-3-[2-(tetrahydro-pyran-2-yloxy)-ethylsulfanyl]-indol-1-yl}-acetonitrile (0.296 g, 0.84 mmole) was oxidized to {5-Chloro-3-[2-(tetrahydro-pyran-2-yloxy)-ethylsulfonyl]-indol-1-yl}-acetonitrile (0.134 g, 42% yield).

Step 5
5-chloro-1-(4,5-dihydro-1H-imidazol-2-ylmethyl)-3-[2-(tetrahydro-pyran-2-yloxy)-ethanesulfonyl]-1H-indole

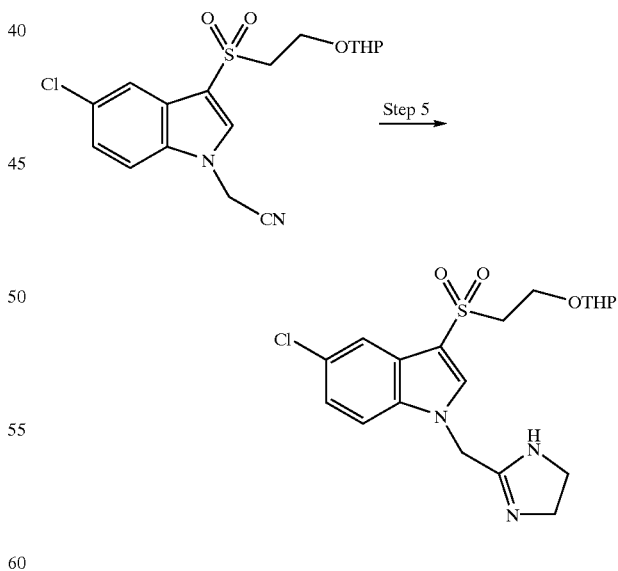

Using the procedure of Example 1, Step 5, 5-chloro-1-(4,5-dihydro-1H-imidazol-2-ylmethyl)-3-[2-(tetrahydro-pyran-2-yloxy)-ethanesulfonyl]-1H-indole was prepared from {5-Chloro-3-[2-(tetrahydro-pyran-2-yloxy)-ethylsulfonyl]-indol-1-yl}-acetonitrile.

Step 6

2-[5-Chloro-1-(4,5-dihydro-1H-imidazol-2-ylmethyl)-1H-indole-3-sulfonyl]-ethanol

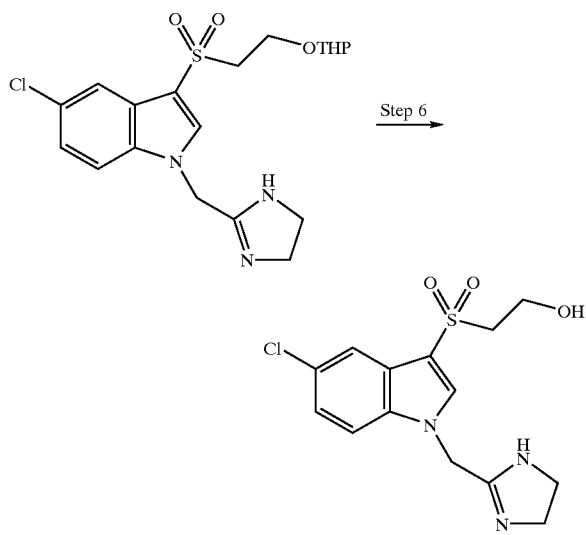

The 5-chloro-1-(4,5-dihydro-1H-imidazol-2-ylmethyl)-3-[2-(tetrahydro-pyran-2-yloxy)-ethanesulfonyl]-1H-indole (0.028 g) prepared in the previous Step was dissolved in 4 ml acetic acid:water (2:1) and stirred at 45–50° C. for 3 h. The solvents were removed under reduced pressure and the crude product was purified by column chromatography (silica gel) eluting with 3–5% methanol in methylene chloride with 0.1% ammonium hydroxide added. The 2-[5-Chloro-1-(4,5-dihydro-1H-imidazol-2-ylmethyl)-1H-indole-3-sulfonyl]-ethanol thus obtained weighed 0.005 g after drying.

Example 8

2,5-dichloro-1-(4,5-dihydro-1H-imidazol-2-ylmethyl)-3-methanesulfonyl-1H-indole

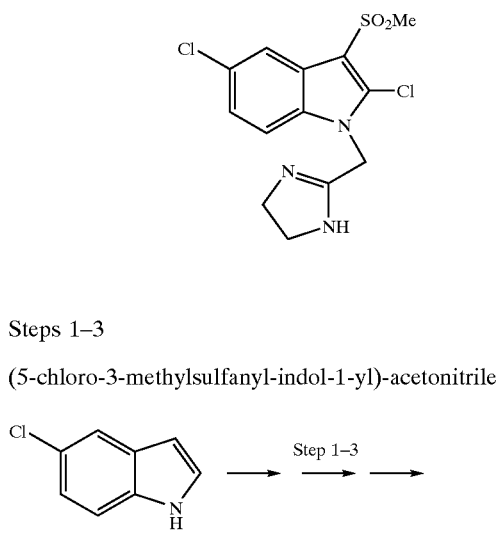

Steps 1–3

(5-chloro-3-methylsulfanyl-indol-1-yl)-acetonitrile

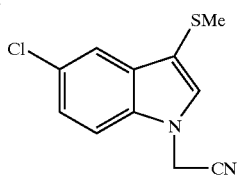

Using the procedures described in Example 1, Steps 1–3, (5-chloro-3-methylsulfanyl-indol-1-yl)-acetonitrile was prepared from 5-chloroindole.

Step 4

(5-Chloro-3-methanesulfinyl-indol-1-yl)-acetonitrile

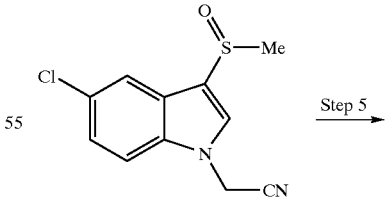

To a solution of (5-chloro-3-methylsulfanyl-indol-1-yl)-acetonitrile (1.0 g, 4.22 mmole) dissolved in methanol (65 ml) cooled to ca. 0° C., was added a cold solution (ca. 7° C.) of Oxone® (1.29 g, 2.11 mmole) dissolved in water (40 ml) in portions over a 10 minute time period. The cooling bath was removed and the solution was stirred at room temperature for 4 h. Tlc analysis at this point showed some unreacted starting material and thus 0.1 g more Oxone® was added and the mixture continued stirring overnight. The reaction mixture was evaporated to dryness and the residue was taken up in methanol and the insoluble material was filtered. The methanol soluble material was isolated by evaporation of the solvent and the residue was triturated with ether which was discarded and then with toluene. The solid which remained was further purified by column chromatography (silica gel) eluting with methanol:methylene chloride (3:97). The resulting (5-chloro-3-methanesulfinyl-indol-1-yl)-acetonitrile weighed 0.851 g (80% yield) after drying.

Step 5

(2,5-dichloro-3-methylsulfanyl-indol-1-yl)-acetonitrile

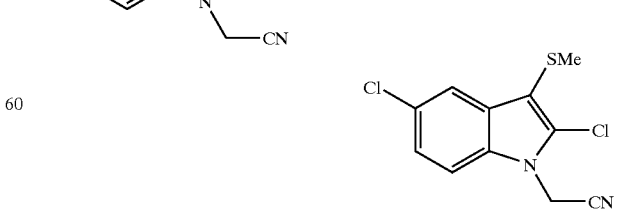

Following a procedure similar to that reported by Greenhouse et al., J. Org. Chem. 53 (1988) 2634, a solution of (5-chloro-3-methanesulfinyl-indol-1-yl)-acetonitrile (0.851 g, 3.38 mmole) in methylene chloride (85 ml) was cooled to 0° C. and solid sodium bicarbonate (3.66 g) was added. Thionyl chloride (0.422 g, 3.55 mmole) was dissolved in methylene chloride and added dropwise over a 45 minute period. Upon termination of addition, the reaction mixture was stirred an additional 15 m. Tlc analysis revealed the presence of a small amount of starting material. Additional thionyl chloride was added, one drop at a time until tlc analysis revealed the total consumption of starting material. When no more starting material was present, the entire reaction mixture was poured onto a short silica gel column and the product was eluted with methylene chloride and isolated by evaporation of the solvent to afford 0.657 g (72%) pure (2,5-dichloro-3-methylsulfanyl-indol-1-yl)-acetonitrile.

Step 6
(2,5-dichloro-3-methylsulfonyl-indol-1-yl)-acetonitrile

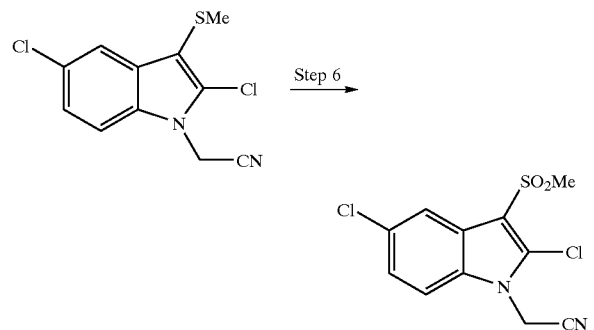

Using the same procedure as Example 1, Step 4, (2,5-dichloro-3-methylsulfanyl-indol-1-yl)-acetonitrile from the above Step was oxidized to (2,5-dichloro-3-methyl-sulfonyl-indol-1-yl)-acetonitrile in nearly quantitative yield.

Step 7
2-(2,5-dichloro-3-methanesulfonyl-indol-1-yl)-acetimidic acid ethyl ester hydrochloride

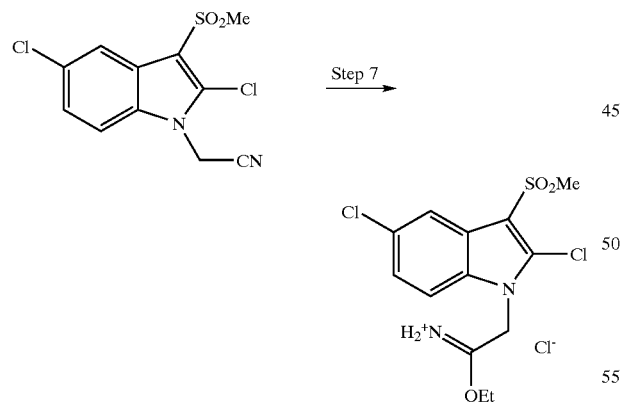

A solution of (2,5-dichloro-3-methylsulfonyl-indol-1-yl)-acetonitrile (0.303 g, 1 mmole) in dry chloroform (15 ml) was cooled to 0° C. under a nitrogen atmosphere. To this solution was added anhydrous ethanol (0.35 ml). Dry hydrogen chloride gas was bubbled into the reaction mixture to saturation at 0° C. The flask was stoppered and stirred for 2 h at 0 and left in the freezer overnight. The resulting white solid precipitate was filtered off and dried to afford 0.353 g (91%) of 2-(2,5-dichloro-3-methanesulfonyl-indol-1-yl)-acetimidic acid ethyl ester hydrochloride.

Step 8
2,5-Dichloro-1-(4,5-dihydro-1H-imidazol-2-ylmethyl)-3-methanesulfonyl-1H-indole

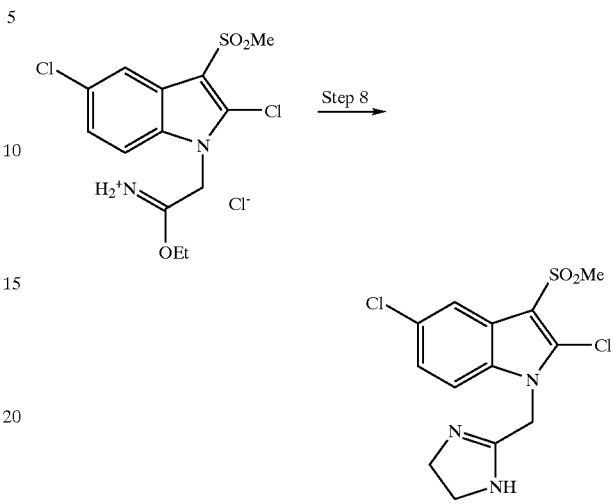

To a solution of ethylene diamine(0.065 g, 1.092 mmole) in ethanol:chloroform (30 ml, 1:1) at 0° C. under a nitrogen atmosphere was added 2-(2,5-dichloro-3-methanesulfonyl-indol-1-yl)-acetimidic acid ethyl ester hydrochloride (0.351 g, 0.91 mmole) dissolved in chloroform (5 ml). The reaction mixture was stirred at room temperature for 2 h and then evaporated to dryness. The residue was purified by column chromatography (silica gel) eluting the product with 7:93 methanol:methylene chloride with 0.1% ammonium hydroxide added. The resulting product, pure 2,5-dichloro-1-(4,5-dihydro-1H-imidazol-2-ylmethyl)-3-methanesulfonyl-1H-indole weighed 0.314 g (99.7% yield).

Example 9

[5-Chloro-1-(4,5-dihydro-1H-imidazol-2-ylmethyl)-3-methanesulfonyl-1H-indol-2-yl]-(3-morpholin-4-yl-propyl)-amine

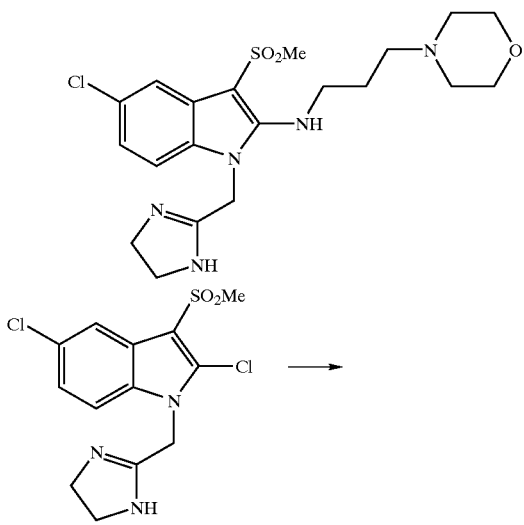

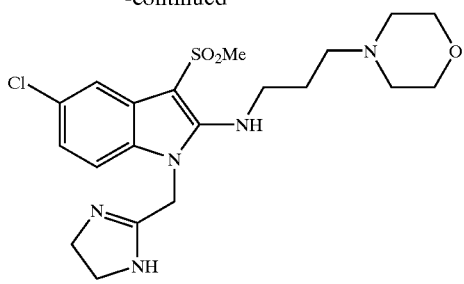

2,5-Dichloro-1-(4,5-dihydro-1H-imidazol-2-ylmethyl)-3-methanesulfonyl-1H-indole(0.050 g, 0.144 mmole) from Example 8 was dissolved in DMF (0.3 ml) and 3-morpholin-4-yl-propylamine (0.021 g, 0.144 mmole) was added at room temperature. The reaction mixture was stirred overnight.

The solvent was removed at reduced pressure and the crude mixture was dried under high vacuum overnight and then purified by column chromatography (7:93 methanol:methylene chloride with 0.2% NH$_4$OH added). The product was isolated by evaporation and converted to its hydrochloride salt by treatment with HCl in alcohol. Evaporation to dryness gave a syrup which could not be crystallized, but instead was thoroughly dried under high vacuum to afford analytically pure [5-Chloro-1-(4,5-dihydro-1H-imidazol-2-ylmethyl)-3-methanesulfonyl-1H-indol-2-yl]-(3-morpholin-4-yl-propyl)-amine (0.052 g, 73% yield).

Also prepared by the above procedure were the compounds:

[5-Chloro-1-(4,5-dihydro-1H-imidazol-2-ylmethyl)-3-methanesulfonyl-1H-indol-2-yl]-(2-morpholin-4-yl-ethyl)-amine;

N1-[5-Chloro-1-(4,5-dihydro-1H-imidazol-2-ylmethyl)-3-methanesulfonyl-1H-indol-2-yl]-ethane-1,2-diamine;

[5-Chloro-1-(4,5-dihydro-1H-imidazol-2-ylmethyl)-3-methanesulfonyl-1H-indol-2-yl]-methyl-amine; and 2-[5-Chloro-1-(4,5-dihydro-1H-imidazol-2-ylmethyl)-3-methanesulfonyl-1H-indol-2-ylamino]-ethanol.

Example 10

2-[5-Chloro-1-(4,5-dihydro-1H-imidazol-2-ylmethyl)-3-methanesulfonyl-1H-indol-2-yl]-ethanol

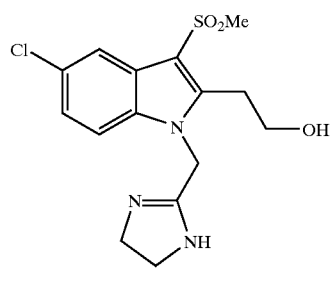

Step 1

(5-Chloro-3-methylsulfanyl-1H-indol-2-yl)-acetic acid methyl ester

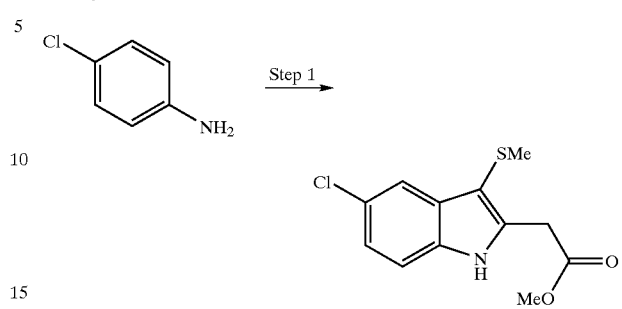

Using a procedure similar to that described in Example 4, step 1, substituting 4-chloroaniline for 2-chloroaniline (0.50 g, 3.9 mmole) and substituting 4-methylsulfanyl-3-oxo-butyric acid methyl ester (0.636 g, 3.9 mmole) [(64127-51-1) J. Med. Chem. (1992), 35(26), 4875–84] for 1-methylsulfanyl-propan-2-one, (5-chloro-3-methylsulfanyl-1H-indol-2-yl)-acetic acid methyl ester (0.91 g, 54% yield) was prepared.

Step 2

2-(5-Chloro-3-methylsulfanyl-1H-indol-2-yl)-ethanol

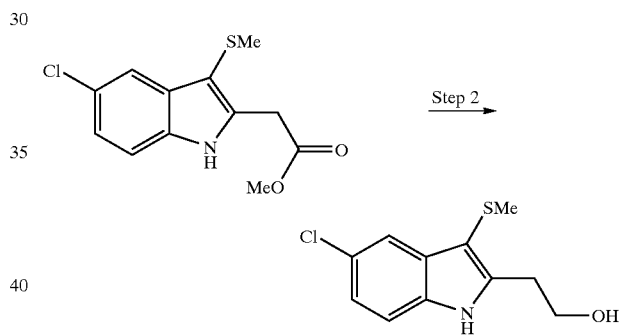

To a solution of (5-chloro-3-methylsulfanyl-1H-indol-2-yl)-acetic acid methyl ester (0.252 g, 0.93 mmole) in ether (10 ml) was added 0.93 ml of a 1M solution of lithium aluminum hydride in ether at room temperature. The reaction mixture was stirred for 15 minutes, after which time sodium sulfate decahydrate (1 g) was cautiously added. The reaction mixture was stirred for an hour at room temperature, filtered, and the filtrate evaporated to dryness. The crude alcohol was purified by column chromatography (silica gel) using 7:3 hexane:ethyl acetate as the eluting solvent. The pure 2-(5-chloro-3-methylsulfanyl-1H-indol-2-yl)-ethanol was isolated as a pale solid (0.191 g, 84% yield).

Step 3

2-(5-Chloro-3-methanesulfonyl-1H-indol-2-yl)-ethanol

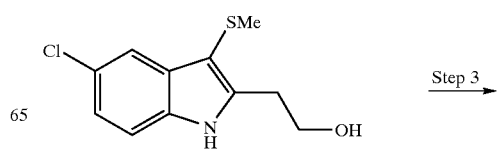

-continued

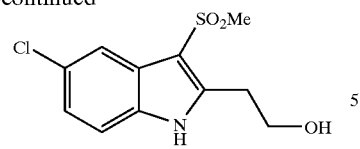

Following the procedure of Example 2, Step 1, 2-(5-chloro-3-methanesulfonyl-1H-indol-2-yl)-ethanol (0.128 g, 64% yield) was prepared from 2-(5-chloro-3-methylsulfanyl-1H-indol-2-yl)-ethanol (0.176 g, 0.72 mmole) obtained in the above Step.

Step 4

[5-Chloro-2-(2-hydroxy-ethyl)-3-methanesulfonyl-indol-1-yl]-acetonitrile

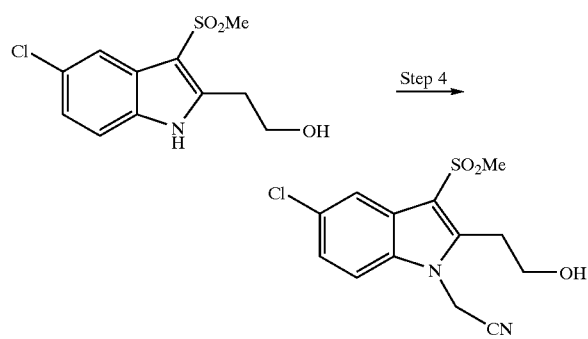

Following the procedure of Example 2, Step 2, [5-Chloro-2-(2-hydroxy-ethyl)-3-methanesulfonyl-indol-1-yl]-acetonitrile (0.081 g, 60% yield) was prepared from 2-(5-Chloro-3-methanesulfonyl-1H-indol-2-yl)-ethanol (0.118 g, 0.43 mmole).

Step 5

2-[5-Chloro-1-(4,5-dihydro-1H-imidazol-2-ylmethyl)-3-methanesulfonyl-1H-indol-2-yl]-ethanol

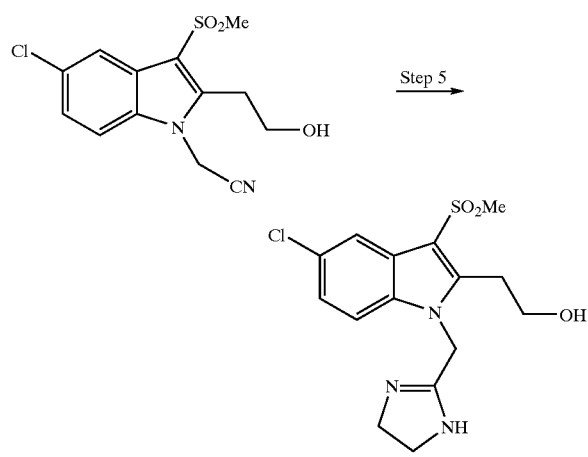

Following the procedure described in Example 1, Step 5, 2-(5-chloro-3-methanesulfonyl-1H-indol-2-yl)-ethanol (0.045 g, 0.14 mmole) afforded 2-[5-chloro-1-(4,5-dihydro-1H-imidazol-2-ylmethyl)-3-methanesulfonyl-1H-indol-2-yl]-ethanol (0.041 g, 80% yield).

Example 11

5-Chloro-1-(4,5-dihydro-1H-imidazol-2-ylmethyl)-3-methanesulfonyl-2-(2-methoxy-ethyl)-1H-indole

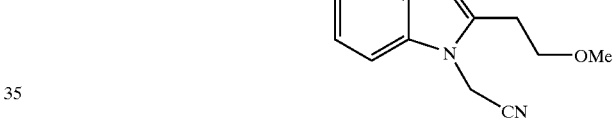

Step 1

[5-Chloro-3-methanesulfonyl-2-(2-methoxy-ethyl)-indol-1-yl]-acetonitrile

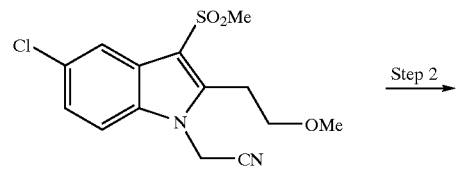

Using the procedure described in Tetrahedron Letters 31(38), 5507–08, [5-cloro-2-(2-hydroxy-ethyl)-3-methanesulfonyl-indol-1-yl]-acetonitrile (0.312 g, 1 mmole) was vigorously stirred in methylene chloride (4 ml) containing tetrafluoroboric acid (0.087 g, 1 mmole) while 0.5 ml of a 2N solution of TMSCHN$_2$ in hexane was added dropwise at 0° C. over a 5 minute period. Three more portions of TMSCHN$_2$ were added (0.25 ml each) similarly at 20 minute intervals. The solution was stirred for 30 minutes beyond the addition process at 0° C., poured into water, washed once with water, dried over magnesium sulfate, filtered and evaporated to dryness. The residue was purified by column chromatography (silica gel) using 1:1 hexane:ethyl acetate as the eluting solvent to afford [5-chloro-3-methanesulfonyl-2-(2-methoxy-ethyl)-indol-1-yl]-acetonitrile (0.138 g, 42% yield) as well as recovered starting material (0.160 g).

Step 2

5-chloro-1-(4,5-dihydro-1H-imidazol-2-ylmethyl)-3-methanesulfonyl-2-(2-methoxy-ethyl)-1H-indole.

-continued

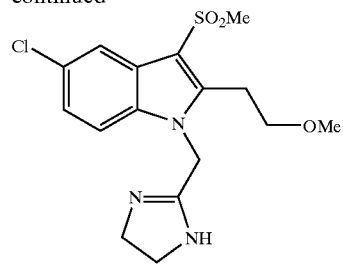

Using a procedure similar to that described in Example 10, Step 4, [5-chloro-3-methanesulfonyl-2-(2-methoxy-ethyl)-indol-1-yl]-acetonitrile (0.110 g, 0.33 mmole) from Step 1 was transformed into 5-chloro-1-(4,5-dihydro-1H-imidazol-2-ylmethyl)-3-methanesulfonyl-2-(2-methoxy-ethyl)-1H-indole (0.085 g, 68% yield).

Example 12

1-(4,5-Dihydro-1H-imidazol-2-ylmethyl)-5-nitro-1H-indole-3-sulfonic acid amide

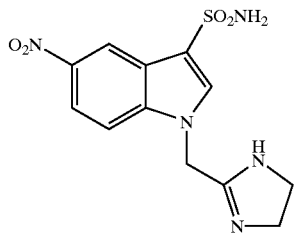

Step 1
(5-Nitro-indol-1-yl)-acetonitrile

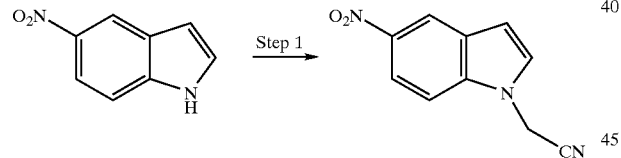

To a solution of 5-nitroindole (1.62 g, 10 mmole) in DMF (15 ml) was added sodium hydride (60% in oil, 0.440 g, 11 mmole). The reaction mixture was stirred for 30 minutes at room temperature after which time bromoacetonitrile (1.25 g, 10.5 mmole) was added via syringe. After 1 h reaction time at the same temperature, the mixture was poured into 200 ml of water. The precipitate, (5-nitro-indol-1-yl)-acetonitrile, was collected (1.96, 97% yield) and was used without further purification.

Step 2
1-Carbamoylmethyl-5-nitro-1H-indole-3-sulfonyl chloride

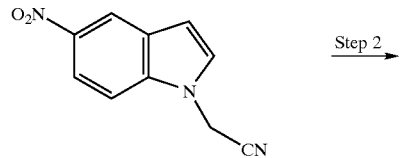

-continued

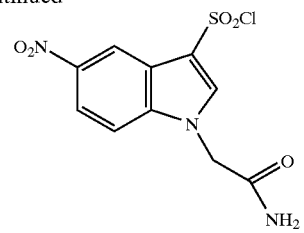

Chlorosulfonic acid (3.05 ml, 45.9 mmole) from the above Step was added to a suspension of anhydrous sodium sulfate (0.71 g) in methylene chloride (30 ml). After stirring for 25 minutes at room temperature, (5-nitro-indol-1-yl)-acetonitrile (1.00 g) dissolved in methylene chloride was added via syringe. After stirring for 2 h, the reaction mixture was worked up by the cautious addition of ice. When the ice had melted, the mixture was filtered to afford an off-white powder which was washed well with water to afford 0.806 g of 1-carbamoylmethyl-5-nitro-1H-indole-3-sulfonyl chloride (51% yield).

Step 3
2-(5-Nitro-3-sulfamoyl-indol-1-yl)-acetamide

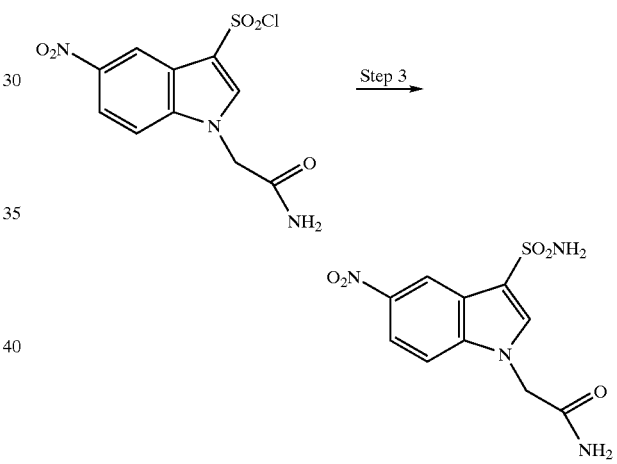

The 1-carbamoylmethyl-5-nitro-1H-indole-3-sulfonyl chloride (0.37 g, 1.165 mmole) of Step 2 was suspended in methylene chloride (2 ml) and added to ammonium hydroxide (4 ml) at room temperature. After stirring for 2 h at room temperature, the reaction flask was heated on a steam bath for 35 min and then allowed to cool to room temperature. The yellow solid which precipitated was filtered off and dried to afford 0.24 g (0.81 mmole, 69% yield) of 2-(5-nitro-3-sulfamoyl-indol-1-yl)-acetamide.

Step 4

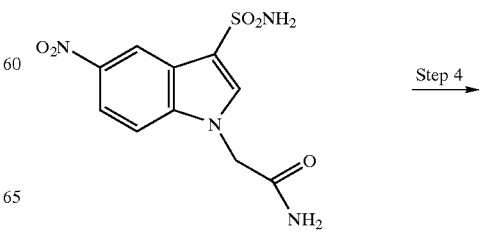

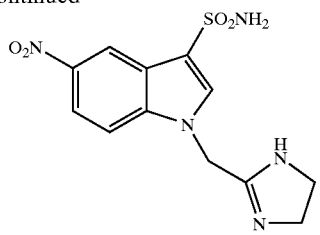

To a solution of trimethyl aluminum in toluene (3.42 ml of a 2 M solution) was added ethylene diamine (0.411 g, 6.84 mmole) at 0° C. which was stirred under a nitrogen atmosphere for 30 min. The resulting complex was added to 2-(5-nitro-3-sulfamoyl-indol-1-yl)-acetamide (0.204 g, 0.683 mmole) suspended in toluene. The reaction mixture was brought to reflux and held at this temperature overnight. The next day 1.5 ml more trimethyl aluminum was added and the reaction was heated at reflux for 64 h more. After cooling, methanol was slowly added and the solution was filtered. Upon evaporation, the solid residue thus obtained was purified by chromatography (silica gel, 7:93 methanol-:methylene chloride+0.1% ammonium hydroxide added). The pure 1-(4,5-Dihydro-1H-imidazol-2-ylmethyl)-5-nitro-1H-indole-3-sulfonic acid amide was collected, evaporated to dryness and converted to its hydrochloride salt by treatment with HCl in alcohol.

Example 13

5-Chloro-1-(4,5-dihydro-1H-imidazol-2-ylmethyl)-2-isopropyl-3-methanesulfonyl-1H-indole

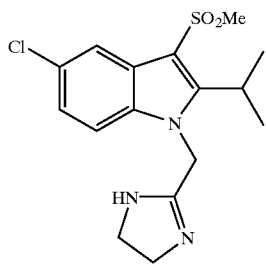

Step 1
[4-chloro-2-(3-methyl-2-oxo-butyl)-phenyl]-carbamic acid tert-butyl ester

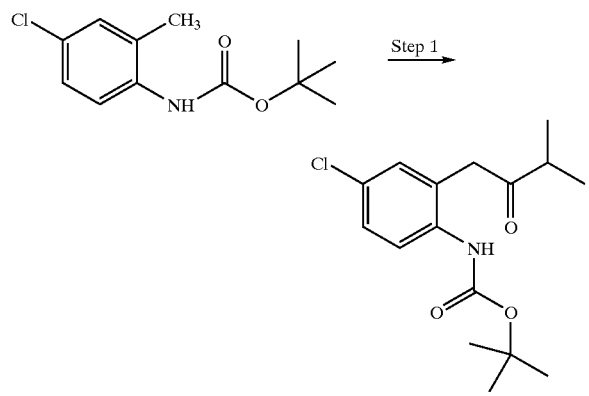

Following the procedure described by R. D. Clark et al. in Synthesis, 871 (1991), (4-chloro-2-methyl-phenyl)-carbamic acid tert-butyl ester (2.18 g, 9 mmole) was dissolved in anhydrous THF (30 ml) and cooled to −40° C. and s-BuLi (14.56 ml 1.3N in cyclohexane) was added slowly at such a rate to maintain the temperature below −25° C. The bright yellow solution was cooled to −50° C. and a solution of N-methoxy-N-methyl-isobutyramide (1.24 g, 9.5 mmole) in THF (5 ml) was added. The mixture was allowed to warm up to −10° C. over a 20 m period during which time the solution turned nearly colorless. Ether (50 ml) was added and the solution was poured into 1% aqueous HCl (50 ml). The aqueous layer was extracted a second time with ether (30 ml) and the combined organic extracts were washed with water and brine, dried over sodium sulfate, filtered and evaporated to dryness to afford the crude product which was purified by column chromatography (silica gel) eluting with ethyl acetate:hexane (4:1) to afford pure [4-chloro-2-(3-methyl-2-oxo-butyl)-phenyl]-carbamic acid tert-butyl ester.

Step 2
5-chloro-2-isopropyl-1H-indole (1.45 g, 83% yield overall).

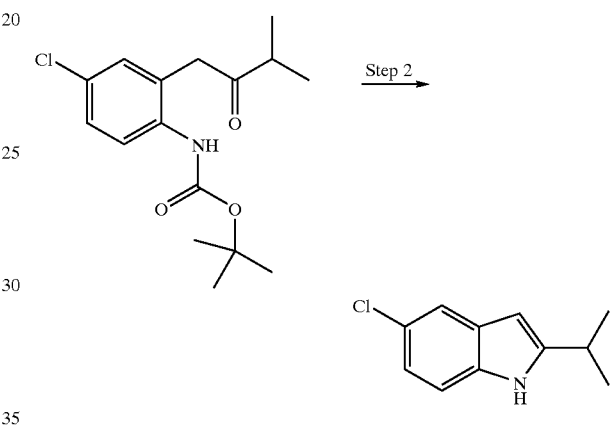

[4-Chloro-2-(3-methyl-2-oxo-butyl)-phenyl]-carbamic acid tert-butyl ester obtained from the previous Step was dissolved in methylene chloride (20 ml) and trifluoroacetic acid (2 ml) was added. After standing at room temperature for 48 h, the solution was washed with water followed by sodium bicarbonate solution, dried over sodium sulfate, filtered and evaporated to dryness. The crude product was purified by column chromatography (silica gel) eluting with ethyl acetate:hexane (95:5) to afford pure 5-chloro-2-isopropyl-1H-indole (1.45 g, 83% yield overall).

Step 3

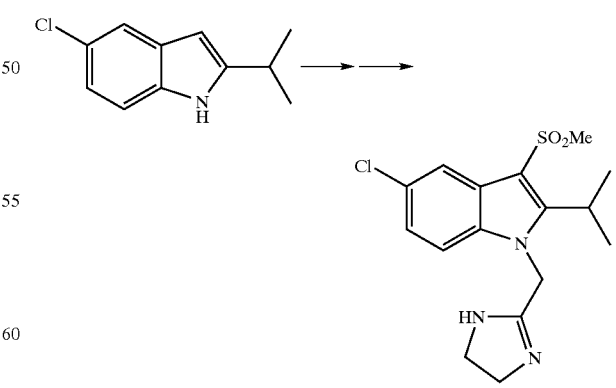

Following the procedures described in Example 1, Steps 1–5a, 5-chloro-2-isopropyl-1H-indole was transformed in to 5-Chloro-1-(4,5-dihydro-1H-imidazol-2-ylmethyl)-2-isopropyl-3-methanesulfonyl-1H-indole.

Similarly, by replacing N-methoxy-N-methyl-isobutyramide in Step 1 with the appropriate alkylamide, the following compounds were prepared:

5-Chloro-1-(4,5-dihydro-1H-imidazol-2-ylmethyl)-2-ethyl-3-methanesulfonyl-1H-indole.

Example 14

4-(4,5-Dihydro-1H-imidazol-2-ylmethyl)-3,4-dihydro-2H-thieno[3,2-b]indole 1,1-dioxide

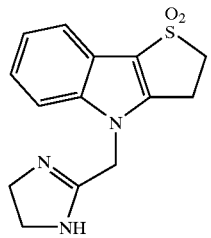

Step 1
3,4-dihydro-2H-thieno[3,2-b]indole

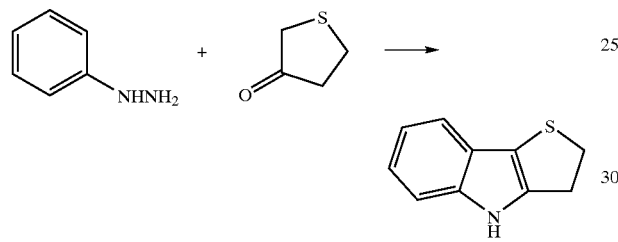

To a solution of phenylhydrazine (5.0 g, 46 mmole) in acetic acid (50 ml) was added dihydro-thiophen-3-one (4.72 g, 46 mmole) at room temperature. Following an exothermic reaction, the temperature was maintained at 80° C. for 2 h. The reaction mixture was poured into water (300 ml) and the precipitate was filtered. Purification on a short column of aluminum oxide (activity II, 6% water) using t-butylmethylether as the eluting solvent gave pure 3,4-dihydro-2H-thieno[3,2-b]indole as a yellow solid (3.9 g, 48% yield), m.p. 152–155° C. (lit. m.p. 153° C., WO01/12603)

Step 2

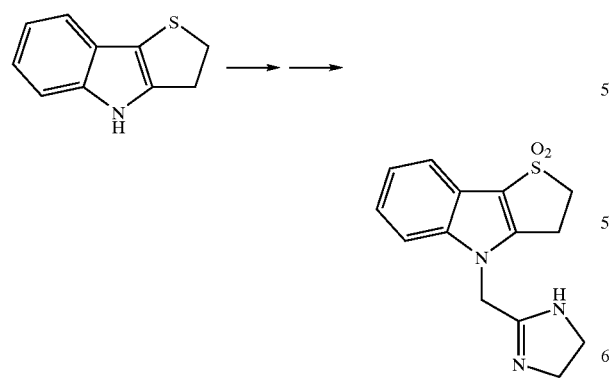

Using a procedures similar to those of Example 2, Steps 1–2 or Example 1, Steps 3–5a, 3,4-dihydro-2H-thieno[3,2-b]indole was transformed into 4-(4,5-dihydro-1H-imidazol-2-ylmethyl)-3,4-dihydro-2H-thieno[3,2-b]indole 1,1-dioxide.

In a similar manner using the appropriate indoles, the following were also prepared:

7-Chloro-4-(4,5-dihydro-1H-imidazol-2-ylmethyl)-3,4-dihydro-2H-thieno[3,2-b]indole 1,1-dioxide;
7-Bromo-4-(4,5-Dihydro-1H-imidazol-2-ylmethyl)-3,4-dihydro-2H-thieno[3,2-b]indole 1,1-dioxide;
4-(4,5-Dihydro-1H-imidazol-2-ylmethyl)-7-methoxy-3,4-dihydro-2H-thieno[3,2-b]indole 1,1-dioxide;
4-(4,5-Dihydro-1H-imidazol-2-ylmethyl)-7-fluoro-3,3a,4,8b-tetrahydro-2H-thieno[3,2-b]indole 1,1-dioxide;
6-Chloro-4-(4,5-dihydro-1H-imidazol-2-ylmethyl)-3,3a,4,8b-tetrahydro-2H-thieno[3,2-b]indole 1,1-dioxide; and
8-Chloro-4-(4,5-dihydro-1H-imidazol-2-ylmethyl)-3,3a,4,8b-tetrahydro-2H-thieno[3,2-b]indole 1,1-dioxide.

Example 15

1-(4,5-Dihydro-1H-imidazol-2-ylmethyl)-3-methanesulfonyl-6-methoxy-1H-indole

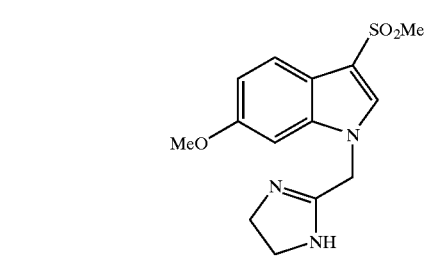

Step 1
6-methoxy-3-thiocyanato-1H-indole

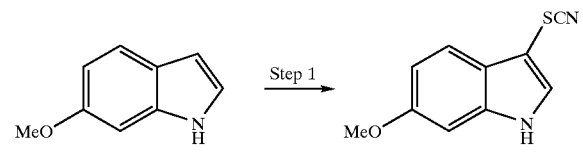

Using the procedure described in Tetrahedron Letters 40 (1999), 1195–1196, 6-methoxy-1H-indole (1.0 g, 6.8 mmole) and ammonium thiocyanate (0.621 g, 8.1 mmole) were dissolved in methanol (35 ml) and treated with ceric ammonium nitrate (8.56 g, 15.6 mmole)in methanol (175 ml) at room temperature. The reaction mixture was stirred for 15 m and then diluted with water (700 ml) and extracted with methylene chloride (4×125 ml). The combined organic extracts were dried over sodium sulfate, filtered and evaporated to dryness. The residue was purified by column chromatography (silica gel) using ethyl acetate:hexane (1:9) as the eluting solvent to afford 6-methoxy-3-thiocyanato-1H-indole (0.40 g 29% yield).

Step 2
6-methoxy-3-methylsulfanyl-1H-indole

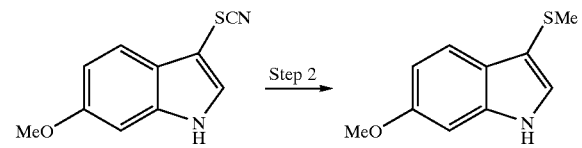

To a solution of 6-methoxy-3-thiocyanato-1H-indole (0.336 g, 1.64 mmole) and methyl iodide (0.700 g, 4.93 mmole) in methanol (10 ml) was added potassium hydroxide solution (0.164 ml, 10N) at 0° C. The reaction mixture was stirred for 1 h at room temperature. Silica gel (5 g) was added to the reaction mixture and the solvent was removed under reduced pressure. The residue was purified on a column of silica gel, eluting the product with mixtures of ethyl acetate:hexane (1:9 to 1:1). The first product which was eluted was the desired 6-methoxy-3-methylsulfanyl-1H-indole (0.120 g, 37% yield) followed by 6-methoxy-1H-indole-3-thiol (0.126 g).

Step 3

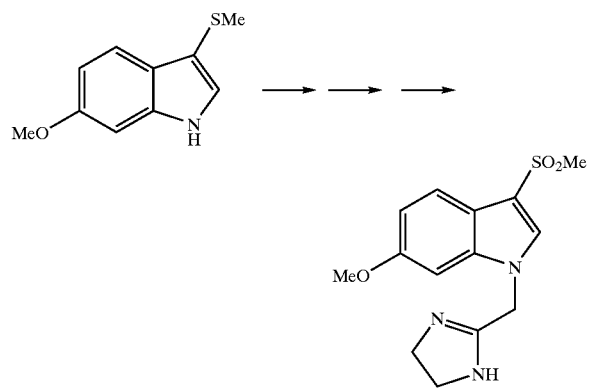

Using a procedures similar to those of Example 2, steps 1–2 or Example 1, Steps 3–5a, 6-Methoxy-3-methylsulfanyl-1H-indole was transformed into 1-(4,5-Dihydro-1H-imidazol-2-ylmethyl)-3-methanesulfonyl-6-methoxy-1H-indole.

Similarly, 1-(4,5-dihydro-1H-imidazol-2-ylmethyl)-3-methanesulfonyl-4-methoxy-1H-indole was prepared using the above procedure.

Example 16

7-Chloro-1-(4,5-dihydro-1H-imidazol-2-ylmethyl)-1H-indole-3-sulfonic acid dimethylamide

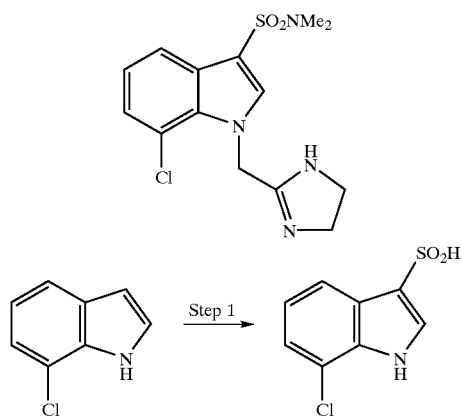

Step 1
7-Chloro-1H-indole-3-sulfonic acid

7-Chloroindole (1.51 g, 10 mmole) was dissolved in 2 ml dichloroethane and cooled under nitrogen to −10° C. in an ice-salt-acetone bath. Trimethylsilylchlorosulfonate (1.89 g, 1.6 ml, 10 mmole) was slowly added with stirring. Upon termination of the addition, the reaction was allowed to warm to room temperature and stirred for 30 min at this temperature. The dark red solution was evaporated to dryness and the solvent was replaced with 50 ml ethyl acetate. Methanol (5 ml) was added and the solvents were removed and the residue thoroughly dried to afford the crude 5-chloro-1H-indole-3-sulfonic acid as a red oil.

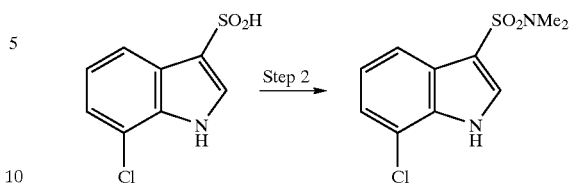

Step 2

7-Chloro-1H-indole-3-sulfonic acid dimethylamide

The red oil of Step 1 was suspended in methylene chloride (20 ml) and oxalyl chloride (2 ml) was added followed by 0.5 ml dry DMF with stirring. The mixture was stirred under a nitrogen atmosphere until all the sulfonic acid dissolved. The solvent was then removed under reduced pressure, replaced with more methylene chloride and evaporated again to remove the excess oxalyl chloride. The crude sulfonyl chloride was then redissolved in methylene chloride and 50 ml 2N dimethyl amine in THF was added and the solution was evaporated to dryness to afford the crude dimethylsulfonamide.

The residue was redissolved in methylene chloride and applied to a short silica gel column. After elution with methylene chloride, the product was eluted with ethyl acetate:dichloromethane (5:95) to afford 7-chloro-1H-indole-3-sulfonic acid dimethylamide as a crystalline solid which weighed 1.28 g (49.3% yield)

Step 3

Following the procedures described in Example 6, Steps 5 and 6, 7-Chloro-1-(4,5-dihydro-1H-imidazol-2-ylmethyl)-1H-indole-3-sulfonic acid dimethylamide was prepared:

6-Chloro-1-(4,5-dihydro-1H-imidazol-2-ylmethyl)-1H-indole-3-sulfonic acid dimethylamide;

6-Bromo-1-(4,5-dihydro-1H-imidazol-2-ylmethyl)-1H-indole-3-sulfonic acid dimethylamide;

6-Bromo-1-(4,5-dihydro-1H-imidazol-2-ylmethyl)-1H-indole-3-sulfonic acid methylamide; and 5-Chloro-1-(4,5-dihydro-1H-imidazol-2-ylmethyl)-2-methyl-1H-indole-3-sulfonic acid dimethylamide.

Example 17

6-Bromo-1-(4,5-dihydro-1H-imidazol-2-ylmethyl)-1H-indole-3-carboxylic acid dimethylamide

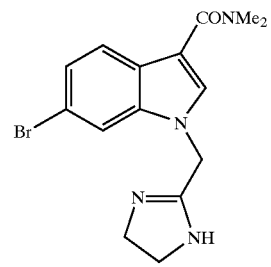

Step 1
6-Bromo-1H-indole-3-carboxylic acid

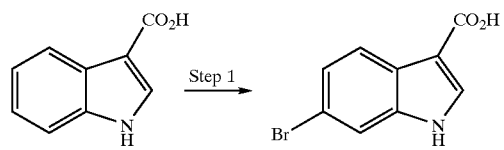

To a solution of indole-3-carboxylic acid (4.81 g, 30 mmole) in acetic acid (50 ml), bromine was added dropwise with stirring at 15° C. After stirring overnight at room temperature the reaction mixture was set aside without stirring for 24 hours during which time pure product crystallized from solution. The precipitate was collected and dried to afford 1.29 g pure 6-bromoindole-3-carboxylic acid. The mother liquor was poured into water (250 ml) and another crop of product was obtained (3.84 g) as a 1:1 mixture of the 6-bromo- and the 5-bromoindole-3-carboxylic acid.

Step 2
6-Bromo-1-cyanomethyl-1H-indole-3-carboxylic acid

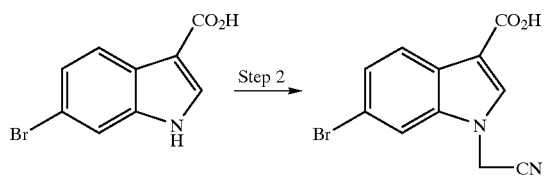

6-Bromo-1H-indole-3-carboxylic acid (0.24 g, 1 mmole) was dissolved in anhydrous dimethylformamide (2 ml) and cooled to 0° C. in a nitrogen atmosphere. With stirring, sodium hydride (60% in oil, 0.088 g, 2.2 mmole) was added all at once and the mixture was stirred at this temperature until no more bubbles evolved (ca. 20–30 minutes). Bromoacetonitrile (0.132 g, 1.1 mmole) was added to the reaction mixture which was then allowed to warm to room temperature over the next hour. The reaction mixture was poured into water, acidified with HCl and a precipitate formed. When dried the product weighed 0.190 g (68% yield) and was sufficiently pure to be used directly in the next step without further purification.

Step 3a
6-Bromo-1-cyanomethyl-1H-indole-3-carboxylic acid dimethylamide

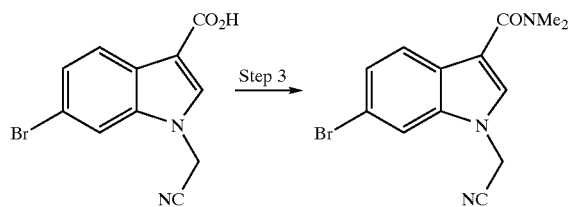

To a suspension of 6-bromo-1-cyanomethyl-1H-indole-3-carboxylic acid (0.478 g, 1.71 mmole) in dichloroethane (100 ml) was added oxalyl chloride (2.6 g, 20.55 mmole) at room temperature followed by a few drops of anhydrous DMF. The reaction was stirred at the same temperature for 24 h. To this mixture was added dimethyl amine (21.4 ml, 2 N in THF, 42.8 mmole) slowly. The reaction mixture was then poured into water (200 ml) and the organic phase was separated, evaporated to dryness and the residue was purified by column chromatography (silica gel, hexane:ethyl acetate 1:1). The pure product weighed 0.335 g (63% yield).

Step 3b
Alternative Method for 6-Bromo-1-cyanomethyl-1H-indole-3-carboxylic acid dimethylamide In a reaction tube was added 26 mg (94 micromol) of 6-bromo-1-cyanomethyl-1H-indole-3-carboxylic acid, 138 mg (approximately 186 micromol of carbodiimide functionality) of polystyrene carbodiimide resin (Argonaut Technologies, Foster City Calif., Product No. 800371), 21.3 mg (158 micromol) of HOBT (hydroxybenzotriazole), 1.5 mL dichloromethane, and 3 drops of DMF. The tube was capped, swirled and allowed to shake on a mechanical shaker for 1 hour at room temperature. The cap was removed, and dimethylamine (1 equivalent, 78 micromol) was added to the tube. The tube was re-capped and shaken for 24 hours at room temperature. 200 microliters of DMF was then added to the tube, and the tube was re-capped and shaken for an additional 48 hours, after which 130 mg (230 micromol) of polystyrene isocyanate resin (Argonaut Technologies, Foster City Calif., Product No. 800260) was added, followed by 1 hour of shaking, to remove excess dimethylamine. The content of the tube was filtered through a Varian liquid extraction tube (pre-washed with 20 microliters of saturated sodium bicarbonate solution), and washed 3× with 1 mL dichloromethane. The combined organic fractions were evaporated under reduced pressure to yield 6-Bromo-1-cyanomethyl-1H-indole-3-carboxylic acid dimethylamide as an oil.

Step 4

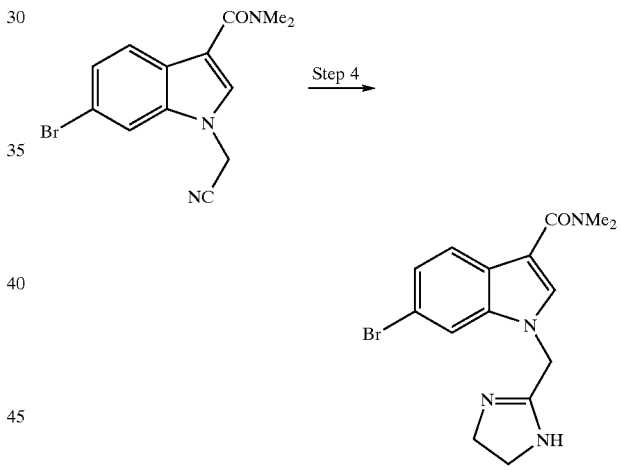

Using a procedure similar to that described in Example 1, step 5a, 6-Bromo-1-cyanomethyl-1H-indole-3-carboxylic acid dimethylamide was converted into 6-bromo-1-(4,5-dihydro-1H-imidazol-2-ylmethyl)-1H-indole-3-carboxylic acid dimethylamide.

In a similar manner, using the appropriate indoles and amines, the following were also prepared:
1-(4,5-dihydro-1H-imidazol-2-ylmethyl)-1H-indole-3-carboxylic acid amide;
1-(4,5-dihydro-1H-imidazol-2-ylmethyl)-1H-indole-3-carboxylic acid dimethylamide;
5-Bromo-1-(4,5-dihydro-1H-imidazol-2-ylmethyl)-1H-indole-3-carboxylic acid dimethylamide;
5-Chloro-1-(4,5-dihydro-1H-imidazol-2-ylmethyl)-1H-indole-3-carboxylic acid dimethylamide;
7-Chloro-1-(4,5-dihydro-1H-imidazol-2-ylmethyl)-1H-indole-3-carboxylic acid amide;
7-Chloro-1-(4,5-dihydro-1H-imidazol-2-ylmethyl)-1H-indole-3-carboxylic acid dimethylamide;

4-Chloro-1-(4,5-dihydro-1H-imidazol-2-ylmethyl)-1H-indole-3-carboxylic acid dimethylamide;

6-Bromo-1-(4,5-dihydro-1H-imidazol-2-ylmethyl)-1H-indole-3-carboxylic acid methylamide;

6-Bromo-1-(4,5-dihydro-1H-imidazol-2-ylmethyl)-1H-indole-3-carboxylic acid ethylamide;

6-Bromo-1-(4,5-dihydro-1H-imidazol-2-ylmethyl)-1H-indole-3-carboxylic acid ethyl-methyl-amide;

6-Bromo-1-(4,5-dihydro-1H-imidazol-2-ylmethyl)-1H-indole-3-carboxylic acid cyclopropylmethyl-amide;

6-Bromo-1-(4,5-dihydro-1H-imidazol-2-ylmethyl)-1H-indole-3-carboxylic acid tert-butylamide;

6-Bromo-1-(4,5-dihydro-1H-imidazol-2-ylmethyl)-1H-indole-3-carboxylic acid isobutyl-amide;

6-Bromo-1-(4,5-dihydro-1H-imidazol-2-ylmethyl)-1H-indole-3-carboxylic acid (2-methoxy-ethyl)-amide;

[6-Bromo-1-(4,5-dihydro-1H-imidazol-2-ylmethyl)-1H-indol-3-yl]-(3-hydroxy-pyrrolidin-1-yl)-methanone;

6-Bromo-1-(4,5-dihydro-1H-imidazol-2-ylmethyl)-1H-indole-3-carboxylic acid (2-dimethylamino-ethyl)-amide;

6-Bromo-1-(4,5-dihydro-1H-imidazol-2-ylmethyl)-1H-indole-3-carboxylic acid ethyl-(2-hydroxy-ethyl)-amide;

6-Bromo-1-(4,5-dihydro-1H-imidazol-2-ylmethyl)-1H-indole-3-carboxylic acid (2-hydroxy-1,1-dimethyl-ethyl)-amide;

6-Bromo-1-(4,5-dihydro-1H-imidazol-2-ylmethyl)-1H-indole-3-carboxylic acid (2-methoxy-1-methyl-ethyl)-amide;

[6-Bromo-1-(4,5-dihydro-1H-imidazol-2-ylmethyl)-1H-indol-3-yl]-(4-methyl-piperazin-1-yl)-methanone;

6-Bromo-1-(4,5-dihydro-1H-imidazol-2-ylmethyl)-1H-indole-3-carboxylic acid (tetrahydro-furan-2-ylmethyl)-amide;

[6-Bromo-1-(4,5-dihydro-1H-imidazol-2-ylmethyl)-1H-indol-3-yl]-(4-hydroxy-piperidin-1-yl)-methanone;

6-Bromo-1-(4,5-dihydro-1H-imidazol-2-ylmethyl)-1H-indole-3-carboxylic acid (3-dimethylamino-propyl)-amide;

[6-Bromo-1-(4,5-dihydro-1H-imidazol-2-ylmethyl)-1H-indol-3-yl]-thiomorpholin-4-yl-methanone;

6-Bromo-1-(4,5-dihydro-1H-imidazol-2-ylmethyl)-1H-indole-3-carboxylic acid (2-ethylsulfanyl-ethyl)-amide;

6-Bromo-1-(4,5-dihydro-1H-imidazol-2-ylmethyl)-1H-indole-3-carboxylic acid p-tolylamide;

6-Bromo-1-(4,5-dihydro-1H-imidazol-2-ylmethyl)-1H-indole-3-carboxylic acid (pyridin-4-yl-methyl)-amide;

6-Bromo-1-(4,5-dihydro-1H-imidazol-2-ylmethyl)-1H-indole-3-carboxylic acid (2-pyrrolidin-1-yl-ethyl)-amide;

6-Bromo-1-(4,5-dihydro-1H-imidazol-2-ylmethyl)-1H-indole-3-carboxylic acid dimethylcarbamoylmethyl-methyl-amide;

6-Bromo-1-(4,5-dihydro-1H-imidazol-2-ylmethyl)-1H-indole-3-carboxylic acid (2-tert-butoxy-ethyl)-amide;

6-Bromo-1-(4,5-dihydro-1H-imidazol-2-ylmethyl)-1H-indole-3-carboxylic acid (3-propoxy-propyl)-amide;

1-[6-Bromo-1-(4,5-dihydro-1H-imidazol-2-ylmethyl)-1H-indole-3-carbonyl]-piperidine-4-carboxylic acid amide;

6-Bromo-1-(4,5-dihydro-1H-imidazol-2-ylmethyl)-1H-indole-3-carboxylic acid (2-morpholin-4-yl-ethyl)-amide;

6-Bromo-1-(4,5-dihydro-1H-imidazol-2-ylmethyl)-1H-indole-3-carboxylic acid [3-(2-oxo-pyrrolidin-1-yl)-propyl]-amide;

[6-Bromo-1-(4,5-dihydro-1H-imidazol-2-ylmethyl)-1H-indol-3-yl]-(2-methyl-aziridin-1-yl)-methanone;

6-Bromo-1-(4,5-dihydro-1H-imidazol-2-ylmethyl)-1H-indole-3-carboxylic acid cyclopropylamide;

[6-Bromo-1-(4,5-dihydro-1H-imidazol-2-ylmethyl)-1H-indol-3-yl]-piperazin-1-yl-methanone;

6-Bromo-1-(4,5-dihydro-1H-imidazol-2-ylmethyl)-1H-indole-3-carboxylic acid pentylamide;

6-Bromo-1-(4,5-dihydro-1H-imidazol-2-ylmethyl)-1H-indole-3-carboxylic acid phenylamide;

6-Bromo-1-(4,5-dihydro-1H-imidazol-2-ylmethyl)-1H-indole-3-carboxylic acid pyridin-3-ylamide;

6-Bromo-1-(4,5-dihydro-1H-imidazol-2-ylmethyl)-1H-indole-3-carboxylic acid (2,2,2-trifluoro-ethyl)-amide;

[6-Bromo-1-(4,5-dihydro-1H-imidazol-2-ylmethyl)-1H-indol-3-yl]-(4-methyl-piperidin-1-yl)-methanone;

6-Bromo-1-(4,5-dihydro-1H-imidazol-2-ylmethyl)-1H-indole-3-carboxylic acid cyclohexylamide;

6-Bromo-1-(4,5-dihydro-1H-imidazol-2-ylmethyl)-1H-indole-3-carboxylic acid benzylamide;

6-Bromo-1-(4,5-dihydro-1H-imidazol-2-ylmethyl)-1H-indole-3-carboxylic acid (4-fluoro-phenyl)-amide;

[6-Bromo-1-(4,5-dihydro-1H-imidazol-2-ylmethyl)-1H-indol-3-yl]-(1,4-dioxa-8-aza-spiro[4.5]dec-8-yl)-methanone;

(4-Benzyl-piperazin-1-yl)-[6-bromo-1-(4,5-dihydro-1H-imidazol-2-ylmethyl)-1H-indol-3-yl]-methanone;

[6-Bromo-1-(4,5-dihydro-1H-imidazol-2-ylmethyl)-1H-indol-3-yl]-pyrrolidin-1-yl-methanone;

[6-Bromo-1-(4,5-dihydro-1H-imidazol-2-ylmethyl)-1H-indol-3-yl]-morpholin-4-yl-methanone;

6-Bromo-1-(4,5-dihydro-1H-imidazol-2-ylmethyl)-1H-indole-3-carboxylic acid isopropylamide;

6-Bromo-1-(4,5-dihydro-1H-imidazol-2-ylmethyl)-1H-indole-3-carboxylic acid amide;

6-Bromo-1-(4,5-dihydro-1H-imidazol-2-ylmethyl)-1H-indole-3-carboxylic acid (2-hydroxy-ethyl)-amide; and 6-Bromo-1-(4,5-dihydro-1H-imidazol-2-ylmethyl)-1H-indole-3-carboxylic acid propylamide.

Example 18

6-Chloro-1-(4,5-dihydro-1H-imidazol-2-yl-methyl)-1H-indole-3-carboxylic acid dimethylamide

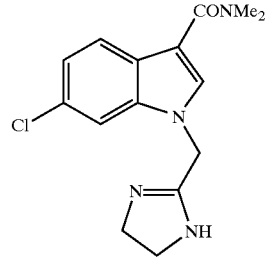

Step 1
(6-Chloro-indol-1-yl)-acetonitrile

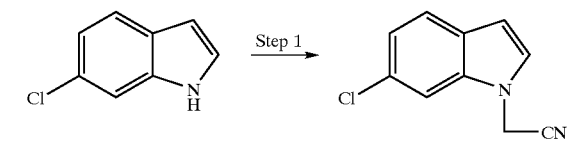

Using a procedure similar to that described in Example 1, step 3, 6-chloro-1H-indole (1 g, 6.5 mmole) was converted into (6-chloro-indol-1-yl)-acetonitrile to afford 0.556 g pure material.

Step 2
6-Chloro-1-cyanomethyl-1H-indole-3-carboxylic acid dimethylamide

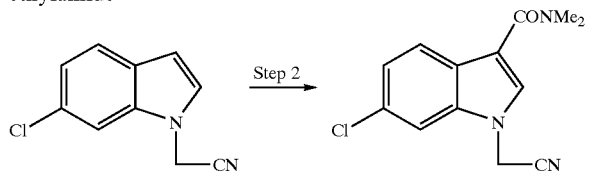

To a solution of (6-chloro-indol-1-yl)-acetonitrile (0.446 g, 2.34 mmole) in acetonitrile (30 ml) was added dichloromethylene dimethylammonium chloride (phosgene imminium chloride) (0.418 g, 2.57 mmole). The reaction mixture was brought to reflux for 14 h and then poured into water (100 ml). The mixture was extracted into ethyl acetate and purified by column chromatography (silica gel, hexane-:ethyl acetate 3:7) to afford the desired 6-chloro-1-cyanomethyl-1H-indole-3-carboxylic acid dimethylamide (0.286 g, 46% yield) in addition to recovered starting material (0.173 g).

Step 3

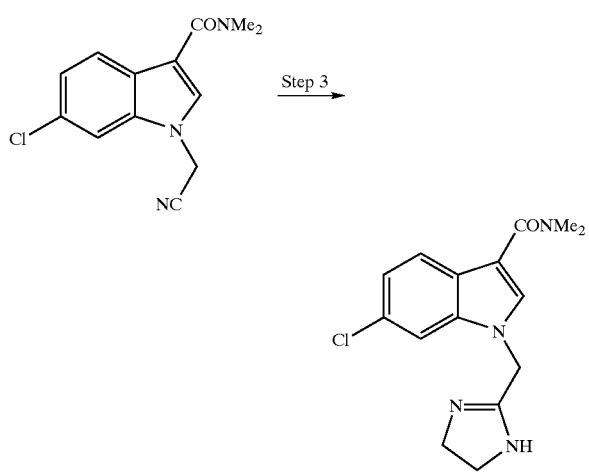

Using a procedure similar to that described in Example 1, step 5a, 6-chloro-1-cyanomethyl-1H-indole-3-carboxylic acid dimethylamide was converted into 6-chloro-1-(4,5-dihydro-1H-imidazol-2-ylmethyl)-1H-indole-3-carboxylic acid dimethylamide.

Example 19

1-(4,5-Dihydro-1H-imidazol-2-ylmethyl)-1H-indole-3-sulfonic acid dimethylamide

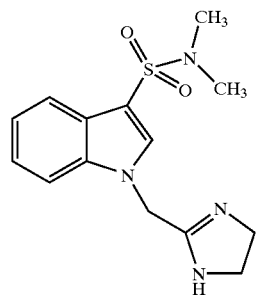

Step 1
Indole-1-yl-acetontrile

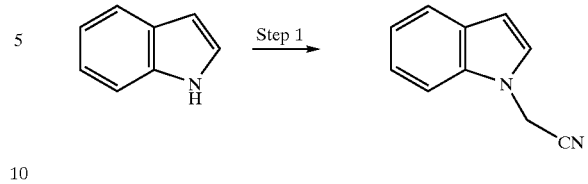

Using the procedure described in Example 12, Step 1, indole was treated with sodium hydride, followed by bromoacetonitrile, to provide indole-1-yl-acetontrile (1.344 g, 8.61 mmol), which was used in the following step without purification.

Step 2
1-(4,5-Dihydro-1H-imidazol-2-ylmethyl)-1H-indole

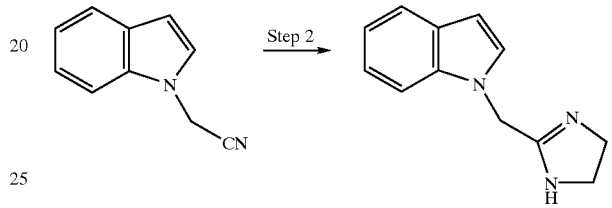

Indole-1-yl-acetontrile (1.344 g, 8.61 mmol) from step 1 was dissolved in methanol (30 mL) and cooled on an ice bath. Solid sodium methoxide (0.58 g, 10.76 mmol) was added in portions to the cooled solution, and the mixture was stirred at ice bath temperature and allowed to warm up to 20° C. with stirring over 6 hours. Ethylene diamine dihydrochloride (1.139 g, 8.56 mmol) was then added, and the mixture was stirred at room temperature overnight. The mixture was evaporated to dryness with a rotary evaporator to yield crude 1-(4,5-dihydro-1H-imidazol-2-ylmethyl)-1H-indole, which was used in the following step without purification.

Step 3
1-(4,5-dihydro-1H-imidazol-2-ylmethyl)-1H-indole-3-sulfonic acid

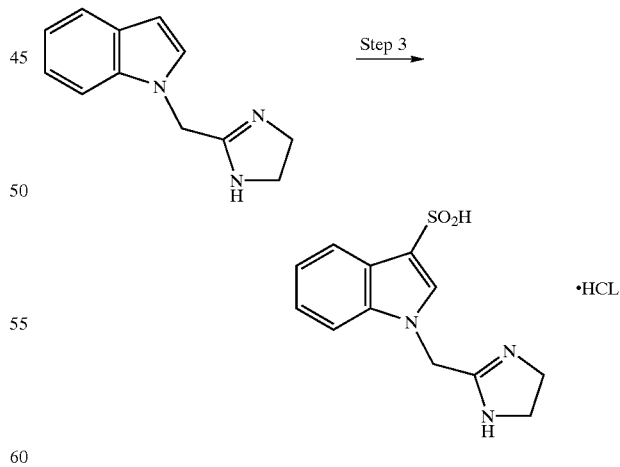

1-(4,5-Dihydro-1H-imidazol-2-ylmethyl)-1H-indole (1.0 g, 4.243 mmol) was dissolved/suspended in dichloroethane (120 ml) and cooled in ice under a nitrogen atmosphere. Trimethylsilylchlorosulfonate (0.654 ml, 0.801 g, 4.243 mmol) was added to the cooled solution dropwise with stirring. The mixture was allowed to warm up to room temperature with stirring, and stirring was continued overnight. Methanol (20 mL) was then added, followed by stirring at room temperature for 20 minutes. The mixture was then rotovapped to dryness. The crude product was recrystallized from MeOH/EtOAc as the hydrochloride salt of 1-(4,5-dihydro-1H-imidazol-2-ylmethyl)-1H-indole-3-sulfonic acid.

Step 4
1-(4,5-dihydro-1H-imidazol-2-ylmethyl)-1H-indole-3-sulfonyl chloride

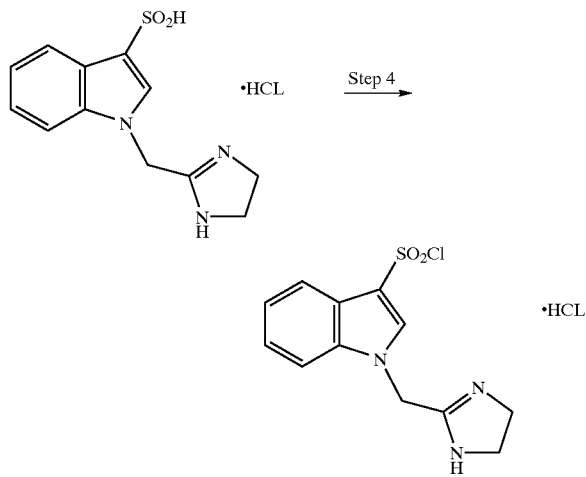

1-(4,5-Dihydro-1H-imidazol-2-ylmethyl)-1H-indole-3-sulfonic acid hydrochloride (1.52 g, 4.814 mmol) from Step 3 was dissolved/suspended in methylene chloride (25 mL) and stirred at room temperature. Oxalyl chloride (2 mL) was added dropwise to the mixture, after which stirring was continued for 3 hours. The mixture was then evaporated to dryness, and excess oxyalyl chloride was azeotroped off with methylene chloride (3×) to provide 1-(4,5-dihydro-1H-imidazol-2-ylmethyl)-1H-indole-3-sulfonyl chloride as a hydrochloride salt.

Step 5
1-(4,5-Dihydro-1H-imidazol-2-ylmethyl)-1H-indole-3-sulfonic acid dimethylamide

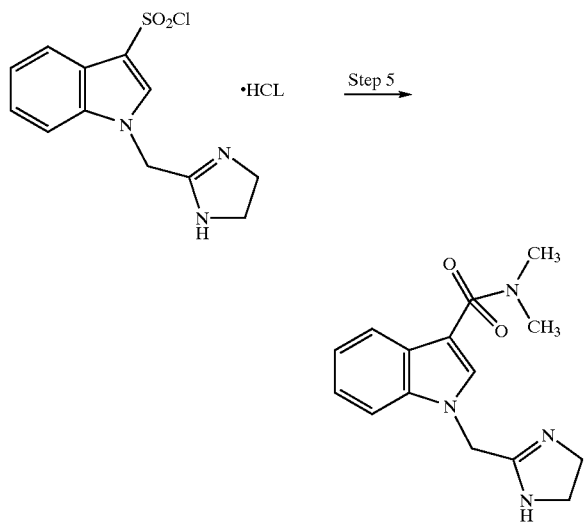

1-(4,5-Dihydro-1H-imidazol-2-ylmethyl)-1H-indole-3-sulfonyl chloride hydrochloride (0.297 g, 1 mmol) was dissolved in 1-methylpyrrlolidinone (14 mL) and stirred. Excess dimethylamine in 1-methylpyrrlolidinone was added to the stirring solution, after which the mixture was allowed to stand at room temperature for 15 minutes. Saturated aqueous sodium bicarbonate (30 mL) was then added, and the mixture was evaporated to dryness. The residue was purified by preparative HPLC to provide 1-(4,5-dihydro-1H-imidazol-2-ylmethyl)-1H-indole-3-sulfonic acid dimethylamide as a crystalline solid.

In a similar manner, by substituting the appropriate indole in Step 1 and the appropriate amine in Step 5, the following were also prepared:

5-chloro-1-(4,5-dihydro-1H-imidazol-2-ylmethyl)-1H-indole-3-sulfonic acid allylamide;

5-chloro-1-(4,5-dihydro-1H-imidazol-2-ylmethyl)-3-(pyrrolidine-1-sulfonyl)-1H-indole;

5-chloro-1-(4,5-dihydro-1H-imidazol-2-ylmethyl)-1H-indole-3-sulfonic acid cyclopropylmethylamide;

5-chloro-1-(4,5-dihydro-1H-imidazol-2-ylmethyl)-1H-indole-3-sulfonic acid (2-hydroxyethyl)-amide;

5-chloro-1-(4,5-dihydro-1H-imidazol-2-ylmethyl)-3-(morpholine-4-sulfonyl)-1H-indole;

1-(4,5-Dihydro-1H-imidazol-2-ylmethyl)-1H-indole-3-sulfonic acid methylamide;

1-(4,5-Dihydro-1H-imidazol-2-ylmethyl)-1H-indole-3-sulfonic acid ethylamide;

1-(4,5-Dihydro-1H-imidazol-2-ylmethyl)-1H-indole-3-sulfonic acid prop-2-ynylamide;

1-(4,5-Dihydro-1H-imidazol-2-ylmethyl)-3-(pyrrolidine-1-sulfonyl)-1H-indole;

1-(4,5-Dihydro-1H-imidazol-2-ylmethyl)-1H-indole-3-sulfonic acid (2-hydroxy-ethyl)-methyl-amide;

1-(4,5-Dihydro-1H-imidazol-2-ylmethyl)-1H-indole-3-sulfonic acid (2-methoxy-ethyl)-methyl-amide;

1-(4,5-Dihydro-1H-imidazol-2-ylmethyl)-3-(morpholine-4-sulfonyl)-1H-indole;

1-(4,5-Dihydro-1H-imidazol-2-ylmethyl)-1H-indole-3-sulfonic acid cyclopropylamide;

1-(4,5-Dihydro-1H-imidazol-2-ylmethyl)-1H-indole-3-sulfonic acid allylamide;

1-(4,5-Dihydro-1H-imidazol-2-ylmethyl)-1H-indole-3-sulfonic acid (2-amino-ethyl)-amide;

1-(4,5-Dihydro-1H-imidazol-2-ylmethyl)-1H-indole-3-sulfonic acid (2-hydroxy-ethyl)-amide;

1-(4,5-Dihydro-1H-imidazol-2-ylmethyl)-1H-indole-3-sulfonic acid cyclopropylmethyl-amide; and 5-Chloro-1-(4,5-dihydro-1H-imidazol-2-ylmethyl)-1H-indole-3-sulfonic acid (2-hydroxy-ethyl)-methyl-amide.

Example 20

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
| --- | --- |
| Ingredient | % wt/wt. |
| Active ingredient | 20.0% |
| Magnesium stearate | 0.5% |
| Crossearmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
| --- | --- |
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (IV) | |
| --- | --- |
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
| --- | --- |
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 21
Functional Assay for Alpha-1A/L Agonist Activity

The inhibitory activity of compounds of this invention in vitro was examined using fluorescent dye determination of intracellular calcium concentrations.

Fluo-3 Loaded Cell Preparation:

Chinese hamster ovary cells CHO-K1 expressing the alpha-1A adrenoceptors (clone 13) are washed 4 times (approx. 300 $\mu$L/well) with fluorometric imaging plate reader (FLIPR) buffer (Hank's buffered saline solution (HBSS), 2 mM $CaCl_2$, 10 mM HEPES, 2,5 mM probenecid, 100 $\mu$M ascorbic acid), with a final volume of 150 $\mu$L/well. Cells are loaded with 50 $\mu$L/well of 8 $\mu$M Fluo-3 AM (Molecular Probes, Eugene, Oreg.), for a final concentration of 2 $\mu$M Fluo-3 AM. Cells are then incubated for 60 min at 37° C. Following dye loading, cells are washed 4 times (approx. 300 $\mu$L/well) with FLIPR buffer with a final volume of 150 $\mu$L/well.

Agonist Assay

The Test compound, control compound and reference compound are run in quadruplicate, 8-point curves on each plate with a final assay concentration range of $10^{-4}$M to $10^{-11}$M for each compound. All compounds are dissolved in DMSO at 10 mM, and serially diluted in FLIPR buffer.

The assay plate is placed in the FLIPR incubation chamber and a baseline fluorescence measurement (excitation @ 488 nm and emission @ 510–570 nm) is obtained (15 sec interval). An experimental run is then commenced. The reaction is started with the addition of 50 $\mu$L/well (at 4× final concentration) of test, control, or reference compound solution from the agonist plate to the assay plate to all 96 wells simultaneously. Fluorescence is measured for 120 sec at 1 sec intervals. Then, a second addition of 5 μM ionomycin (50 μL/well from 5× concentration ionomycin plate) is added to the assay plate. Fluorescence is measured for 30 sec at 1 sec intervals. All experiments are conducted at room temperature.

Measurements

For each assay plate, responses (increase in peak fluorescence) in each well following addition of agonist (test, control and reference) are determined. These responses may be expressed as raw CFU (Corrected Fluorescence Units), as a % maximum ionomycin response or other unit as determined by the investigator.

Statistics

For test compound, control compound (Noerepinephrine (NE) bitartrate), and reference compound, the concentration producing a 50% increase in control response ($EC_{50}$) is determined using iterative curve-fitting methods. Excel spreadsheet or Kaleidagraph software are used to fit data to the general logistic function (E=B+$E_{max}$·$A^{nH}$/$A^{nH}$+$EC_{50}^{nH}$), where B is the corrected baseline fluorescence units (defined as zero), A is the concentration of agonist added and nH is the Hill slope (constrained to unity). $EC_{50}$ values and maxima ($E_{max}$) for each curve can be estimated objectively using this software.

In addition the intrinsic activity (α) is determined. Intrinsic activity is defined as the maximum response to test agonist divided by the maximum response to a full agonist acting through the same receptor. For these experiments, the full agonist is defined as Norepinephrine (NE) bitartrate (control). As used herein an agonist is a compound that elicits a maximal response greater than 50% of that of norpepinephrine with a $pEC_{50}$>5.5.

The compounds in Examples 1 through 19 are alpha-1A/L agonists. Representative $pEC_{50}$ and intrinsic activity (IA) values for these compounds are provided in Table 2.

TABLE 2

| Compound | $pEC_{50}$ | IA |
| --- | --- | --- |
| 1-(4,5-Dihydro-1H-imidazol-2-ylmethyl)-3-methanesulfonyl-2-methyl-1H-indole | 9.08 | 1.00 |
| 1-(4,5-Dihydro-1H-imidazol-2-ylmethyl)-3-methanesulfonyl-1H-indole | 8.64 | 1.07 |
| 1-(4,5-Dihydro-1H-imidazol-2-ylmethyl)-3-methanesulfonyl-6-methoxy-2-methyl-1H-indole | 8.00 | 1.05 |
| 1-(4,5-Dihydro-1Hmidazol-2-ylmethyl)-3-methanesulfonyl-2,5-dimethyl-1H-indole | 7.63 | 0.93 |
| 1-(4,5-Dihydro-1H-imidazol-2-ylmethyl)-3-methanesulfonyl-2-methyl-7-trifluoromethyl-1H-indole | 6.85 | 0.96 |
| 1-(4,5-Dihydro-1H-imidazol-2-ylmethyl)-3,4-bis-methanesulfonyl-2-methyl-1H-indole | 5.98 | 1.04 |
| 1-(4,5-Dihydro-1H-imidazol-2-ylmethyl)-3,6-bis-methanesulfonyl-2-methyl-1H-indole | 4.22 | 0.18 |
| 6-Bromo-1-(4,5-dihydro-1H-imidazol-2-ylmethyl)-1H-indole-3-carboxylic acid dimethylamide | 8.34 | 1.02 |
| 6-Chloro-1-(4,5-dihydro-1H-imidazol-2-ylmethyl)-1H-indole-3-sulfonic acid dimethylamide | 8.04 | 1.00 |

Example 22

Assays for Alpha-1A/L Adrenoceptor Activity

Compounds used in this example were from Sigma Chemical Co., St. Louis, Mo., U.S.A.) unless specified otherwise.

In Vitro: Male white New Zealand rabbits (3–3.5 kg) and Sprague-Dawley rats (250–400 g) were euthanized by $CO_2$ asphyxiation. The bladder (rabbit) or aorta (rat) were removed, extraneous tissue was dissected away, and tissues were placed in oxygenated Krebs' solution (mM: NaCl, 118.5; $NaHCO_3$, 25; dextrose, 5: KCl, 4.8; $CaCl_2$, 2.5; $MgSO_4$, 1.2 and $KH_2PO_4$, 1.2). Cocaine (30 μM), corticosterone (30 μM), ascorbic acid (100 μM), indomethacin (10 μM) and propranolol (1 μM) were added to the Krebs' solution to block neuronal uptake, extraneuronal uptake, auto-oxidation of catecholamines, prostanoid synthesis, beta-adrenoceptors, respectively. The alpha-2 adrenoceptor antagonist idazoxan (0.3 μM, Research Biochemicals, Inc., Natick, Mass., U.S.A.) and the calcium channel antagonist nitrendipine (1 μM, Research Biochemico International, Natick, Mass., U.S.A.) were added the Krebs' solution for rabbit and rat experiments, respectively. Strips of bladder neck (rabbit) approximately 0.8–1.2 cm in length and 2–3 mm in width and aortic rings (2–4 per rat) approximately 3 mm in width, cut as near the heart as possible, were suspended in water-jacketed tissue baths at a resting tension of 1. Tissues were maintained at 34° C. and bubbled continuously with an oxygen/carbon dioxide mixture.

Tissues were primed with norepinephrine (10 μM) and washed for 60 minutes before constructing a first cumulative concentration-effect to norepinephrine. Tissues were then washed for 60 minutes before constructing a second concentration-effect curve to a test agonist. The concentration producing the half maximal response ($pEC_{50}$) and the intrinsic activity (relative to norepinephrine) were recorded. Results for standards and representative compounds of the present invention were determined. Representative compounds of the invention showed activity in this assay.

In Vivo: Anesthetized Pig Urethra/Blood Pressure Model: Female Yucatan micropigs (12–35 kg; ≧10 months old) were anesthetized with ketamine (Aveco Co., Ft. Dodge, Iowa, U.S.A.) followed by pentobarbital (Schering Plough Animal Health Corp., Kenilworth, N.J., U.S.A.). A cuffed endotracheal tube was placed in the trachea and the pig mechanically ventilated with room air under positive pressure. The right or left femoral artery and vein were isolated and cannulated. One of the two cannula inserted into the femoral vein was used to infuse pentobarbital (5–20 mg/kg/hr) via an infusion pump. The second cannula was used to administer test compounds. The cannula inserted into the femoral artery was connected to a blood pressure transducer (Gould/Statham Sprectamed P23 series) for the measurement of aortic blood pressure. Needle electrodes were placed subcutaneously to record a limb lead II ECG and heart rate was monitored by a tachometer triggered by the R-wave of the ECG. Body heat was maintained with an Aquamatic hot water blanket, model K-20, and rectal temperature was continuously monitored with a YSI TeleThermometer, model 43TA.

Following a ventral midline laparotomy, both ureters were cannulated for the exteriorization of urine. The bladder was emptied and a water-filled balloon catheter (reservoir tip of a latex condom attached to PE-190 tubing) attached to an external pressure transducer was inserted through the bladder via a stab incision. The balloon catheter was advanced into the urethra and secured with silk ligatures. Correct placement of the balloon was verified by palpating the urethra when inflating and deflating the balloon.

Following the surgical preparation, blood gases (analyzed by a Nova Stat Profile 3 blood gas analyzer) and pH were adjusted to within normal limits by adjusting respiratory rate, tidal volume, and/or positive-end expiratory pressure. Intraurethral pressure was adjusted to an appropriate baseline (20–40 $cmH_2O$) by inflating or deflating the balloon. Following a 30 minute stabilization period, the pig was pretreated with a beta-adrenoceptor antagonist (propranolol; 100 μg/kg, iv), a non-selective alpha-2 adrenoceptor antagonist [8aR-(8aa,12aa,13aa)]-N-[3-[(5,8a,9,10,11,12a,13,13a- octahydro-3-methoxy-6H-isoquinol[2,1-g][1,3]naphthyridin-12(8H)-yl)-sulfonyl]propyl]-methanesulfonamide (for example, prepared by procedures described by Clark et al., European Patent Application No. 524004 A1) above for compounds according to the present invention) (300 µg/kg, iv) and a ganglionic antagonist (chlorisondamine; 200 µg/kg, iv, prepared according to the procedure described in U.S. Pat. No. 3,025,294). A single phenylephrine challenge (10 µg/kg, iv) was given to verify intraurethral and blood pressure responses. After the response returned to baseline, multiple escalating doses of agonists were administered intravenously and maximal intraurethral and diastolic blood pressure responses following each dose were recorded. Intervals between doses varied from 5–120 minutes to allow responses to return to baseline before giving the next dose. At the end of each experiment, pigs were euthanized by a lethal injection of pentobarbital. The maximum responses for intraurethral and diastolic blood pressure for standards and representative compounds of the invention were determined. Representative compounds of the invention showed activity in this assay.

In Vivo: Conscious Pig Urethra/Blood Pressure Model: Female Yucatan micropigs (12–35 kg; ≧10 months old) were trained to rest quietly in a sling for a week prior to surgery. Only those pigs which acclimated to the sling were used for the study. Pigs were surgically instrumented under aseptic conditions. A telemetry device (Data Science International, St. Paul, Minn., U.S.A., model TA11PAD-70) was implanted into the pig with the cannula potion of the device inserted into the right external iliac artery and advanced into the abdominal aorta. The transmitter portion of the device was placed in a pocket created under the skin in close proximity to the insertion point of the cannula. A vascular access port (Sims Deltec, St. Paul, Minn., U.S.A.) with a silicon catheter was implanted for intravenous administration of test compounds. The catheter portion was inserted into the left or right jugular vein with the port under the skin in the shoulder area. A strain-gauge transducer (SF Products, Madison, Wis., U.S.A.) was sutured to the urethra and the wire exteriorized dorsally. Pigs were allowed at least one week to recover from surgery.

One each experimental day, pigs were placed in the sling and allowed to stabilize before administering a phenylephrine prime (10 µg/kg, iv) to verify the placement of the needle in the vascular access port and calibration of the telemetry and strain-gauge probes. After urethral tension and blood pressure returned to baseline values, a non-cumulative dose-response curve to phenylephrine was constructed. Intervals between doses varied form 5–120 minutes to allow blood pressure to return to baseline levels. Sixty minutes after the last phenylephrine dose returned to baseline, a second non-cumulative curve to test compound was constructed. Responses to test compounds were expressed as a percentage of the maximum response obtained with phenylephrine. Representative compounds of the invention showed activity in this assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the Formula I:

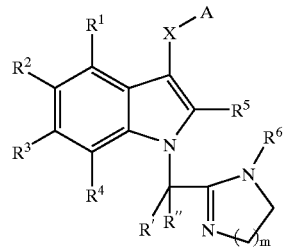

Formula I wherein:

X is —S(O)$_n$— or —C(O);

A is $C_{1-6}$alkyl, aryl, heteroaryl, hydroxyalkyl, or —(CH$_2$)$_p$—NR$^a$R$^b$;

$R^1$, $R^2$, $R^3$, and $R^4$ each independently is hydrogen, halogen, haloalkyl, $C_{1-6}$alkyl, hydroxy, $C_{1-6}$alkoxy, $C_{1-6}$alkylthio, $C_{1-6}$alkylsulfinyl, $C_{1-6}$alkylsulfonyl, $C_{1-6}$alkylsulfonylamino, $C_{1-6}$alkylaminosulfonyl, cyano, nitro, —NR$^a$R$^b$, phenyl, benzyl or benzyloxy, wherein said phenyl, benzyl and benzyloxy are optionally substituted with $C_{1-6}$alkyl, halogen, cyano, nitro, haloalkyl, or $C_{1-6}$alkoxy;

$R^5$ is hydrogen, $C_{1-6}$alkyl, $C_{1-6}$alkoxy, $C_{1-6}$alkoxyalkyl, $C_{1-6}$alkylthio, $C_{1-6}$alkylsulfinyl, $C_{1-6}$alkylsulfonyl, hydroxyalkyl, hydroxyalkylamino, halogen, haloalkyl, cyano, —NR$^a$R$^b$, —NR$^c$—$C_{1-6}$alkyl-NR$^a$R$^b$, or R$^5$ and A together form a $C_2$–$C_3$ alkylene radical;

$R^6$ is hydrogen or $C_{1-6}$alkyl;

R' and R" each independently is hydrogen or alkyl;

$R^a$, $R^b$, and $R^c$ each independently is hydrogen, alkyl, hydroxyalkyl, alkoxyalkyl, aminoalkyl, haloalkyl, alkenyl, alkynyl, cycloalkyl, cycloalkylalkyl, alkylthioalkyl, heterocyclyl, heterocyclylalkyl, aryl, arylalkyl, heteroaryl, heteroarylalkyl, or arylsulfonyl, or $R^a$ and $R^b$ together with the nitrogen they are attached to may also form a 5- to 7-membered non-aromatic heterocyclic ring optionally incorporating an additional ring heteroatom chosen from N, O, or S;

m is 1 or 2;

n is 0, 1 or 2 with the proviso that when n is 0, $R^5$ is not —NR$^a$R$^b$; and p is 0, 1 or 2;

or pharmaceutically acceptable salts thereof.

2. The compound of claim 1, wherein A is $C_{1-6}$alkyl.

3. The compound of claim 2, wherein X is —SO$_2$—.

4. The compound of claim 1, wherein $R^5$ is hydrogen or $C_{1-6}$alkyl.

5. The compound of claim 1, wherein $R^1$, $R^2$, $R^3$, and $R^4$ each independently is hydrogen, halogen, haloalkyl, or $C_{1-6}$alkyl.

6. The compound of claim 3, wherein $R^1$, $R^2$, $R^3$, and $R^4$ each independently is hydrogen, halogen, haloalkyl, or $C_{1-6}$alkyl.

7. The compound of claim 6, wherein $R^1$, $R^2$, $R^3$, and $R^4$ are hydrogen.

8. The compound of claim 6, wherein one of $R^1$, $R^2$, $R^3$, and $R^4$ is halogen, and the others are hydrogen.

9. The compound of claim 6, wherein m is 1.

10. The compound of claim 6, wherein m is 2.

11. The compound of claim 4, wherein $R^5$ is hydrogen.

12. The compound of claim 11, wherein n is 2.

13. The compound of claim 12, wherein $R^1$, $R^2$, $R^3$, and $R^4$ each independently is hydrogen, halogen, haloalkyl, $C_{1-6}$alkyl.

14. The compound of claim 13, wherein one of $R^1$, $R^2$, $R^3$, and $R^4$ is halogen, and the others are hydrogen.

15. The compound of claim 13, wherein $R^1$, $R^2$, $R^3$, and $R^4$ are hydrogen.

16. The compound of claim 13, wherein A is $C_{1-6}$alkyl, alkenyl or cycloalkylalkyl.

17. The compound of claim 4, wherein $R^5$ is methyl, ethyl, n-propyl, isopropyl or hydroxyethyl.

18. The compound of claim 17, wherein n is 2.

19. The compound of claim 18, wherein $R^1$, $R^2$, $R^3$, and $R^4$ each independently is hydrogen, halogen, haloalkyl, or $C_{1-6}$alkyl.

20. The compound of claim 19, wherein one of $R^1$, $R^2$, $R^3$, and $R^4$ is halogen, and the others are hydrogen.

21. The compound of claim 19, wherein $R^1$, $R^2$, $R^3$, and $R^4$ are hydrogen.

22. The compound of claim 19, wherein A is $C_{1-6}$alkyl.

23. The compound of claim 1, wherein X is —$SO_2$— and A is —$(CH_2)_p$—$NR^aR^b$.

24. The compound of claim 23, wherein p is 0 and $R^a$ and $R^b$ are $C_{1-6}$alkyl.

25. The compound of claim 1, wherein X is —C(O).

26. The compound of claim 25, wherein A is —$(CH_2)_p$—$NR^aR^b$.

27. The compound of claim 26, wherein p is 0 and $R^a$ and $R^b$ are $C_{1-6}$alkyl.

28. The compound of claim 27, wherein one of $R^1$, $R^2$, $R^3$, and $R^4$ is halogen, and the others are hydrogen.

29. The compound of claim 27, wherein $R^3$ is halogen and $R^1$, $R^2$ and $R^4$ are hydrogen.

30. The compound of claim 26, wherein p is 0 and $R^a$ and $R^b$ are hydrogen.

31. The compound of claim 26, wherein p is 0 and one of $R^a$ and $R^b$ is hydrogen and the other is $C_{1-6}$alkyl.

32. A pharmaceutical composition comprising a therapeutically effective amount of a compound of the Formula I:

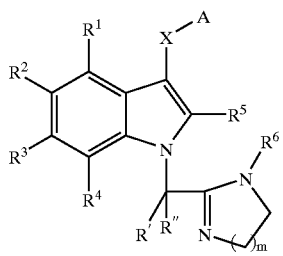

Formula I wherein:
X is —$S(O)_n$— or —C(O)—;
A is $C_{1-6}$alkyl, aryl, heteroaryl, hydroxyalkyl, or —$(CH_2)_p$—$NR^aR^b$;
$R^1$, $R^2$, $R^3$, and $R^4$ each independently is hydrogen, halogen, haloalkyl, $C_{1-6}$alkyl, hydroxy, $C_{1-6}$alkoxy, $C_{1-6}$alkylthio, $C_{1-6}$alkylsulfinyl, $C_{1-6}$alkylsulfonyl, $C_{1-6}$alkylsulfonylamino, $C_{1-6}$alkylaminosulfonyl, cyano, nitro, —$NR^aR^b$, phenyl, benzyl or benzyloxy, wherein said phenyl, benzyl and benzyloxy are optionally substituted with $C_{1-6}$alkyl, halogen, cyano, nitro, haloalkyl, or $C_{1-6}$alkoxy;
$R^5$ is hydrogen, $C_{1-6}$alkyl, $C_{1-6}$alkoxy, $C_{1-6}$alkoxyalkyl, $C_{1-6}$alkylthio, $C_{1-6}$alkylsulfinyl, $C_{1-6}$alkylsulfonyl, hydroxyalkyl, hydroxyalkylamino, halogen, haloalkyl, cyano, —$NR^aR^b$, —$NR^c$—$C_{1-6}$alkyl-$NR^aR^b$, or $R^5$ and A together form a $C_2$-$C_3$ alkylene radical;
$R^6$ is hydrogen or $C_{1-6}$alkyl;
R' and R" each independently is hydrogen or alkyl;
$R^a$, $R^b$, and $R^c$ each independently is hydrogen, alkyl, hydroxyalkyl, alkoxyalkyl, aminoalkyl, haloalkyl, alkenyl, alkynyl, cycloalkyl, cycloalkylalkyl, alkylthioalkyl, heterocyclyl, heterocyclylalkyl, aryl, arylalkyl, heteroaryl, heteroarylalkyl, or arylsulfonyl, or $R^a$ and $R^b$ together with the nitrogen they are attached to may also form a 5- to 7-membered non-aromatic heterocyclic ring optionally incorporating an additional ring heteroatom chosen from N, O, or S;
m is 1 or 2;
n is 0, 1 or 2; and
p is 0, 1 or 2;
or pharmaceutically acceptable salts or solvates thereof.

33. A method for treating a disorder modulated by alpha-1A/L adrenoceptors, wherein the disorder is chosen from the group consisting of urge incontinence, stress incontinence, overflow incontinence, functional incontinence, and nasal congestion, said method comprising administering to a subject in need of such treatment, a safe and effective amount of an alpha-1A/L adrenoceptor agonist compound of the Formula I:

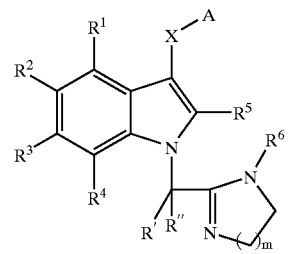

Formula I wherein:
X is —$S(O)_n$— or —C(O)—;
A is $C_{1-6}$alkyl, aryl, heteroaryl, hydroxyalkyl, or —$(CH_2)_p$—$NR^aR^b$;
$R^1$, $R^2$, $R^3$, and $R^4$ each independently is hydrogen, halogen, haloalkyl, $C_{1-6}$alkyl, hydroxy, $C_{1-6}$alkoxy, $C_{1-6}$alkylthio, $C_{1-6}$alkylsulfinyl, $C_{1-6}$alkylsulfonyl, $C_{1-6}$alkylsulfonylamino, $C_{1-6}$alkylaminosulfonyl, cyano, nitro, —$NR^aR^b$, phenyl, benzyl or benzyloxy, wherein said phenyl, benzyl and benzyloxy are optionally substituted with $C_{1-6}$alkyl, halogen, cyano, nitro, haloalkyl, or $C_{1-6}$alkoxy;
$R^5$ is hydrogen, $C_{1-6}$alkyl, $C_{1-6}$alkoxy, $C_{1-6}$alkoxyalkyl, $C_{1-6}$alkylthio, $C_{1-6}$alkylsulfinyl, $C_{1-6}$alkylsulfonyl, hydroxyalkyl, hydroxyalkylamino, halogen, haloalkyl, cyano, —$NR^aR^b$, —$NR^c$—$C_{1-6}$alkyl-$NR^aR^b$, or $R^5$ and A together form a $C_2$-$C_3$ alkylene radical;
$R^6$ is hydrogen or $C_{1-6}$alkyl;
R' and R" each independently is hydrogen or alkyl;
$R^a$, $R^b$, and $R^c$ each independently is hydrogen, alkyl, hydroxyalkyl, alkoxyalkyl, aminoalkyl, haloalkyl, alkenyl, alkynyl, cycloalkyl, cycloalkylalkyl, alkylthioalkyl, heterocyclyl, heterocyclylalkyl, aryl, arylalkyl, heteroaryl, heteroarylalkyl, or arylsulfonyl, or $R^a$ and $R^b$ together with the nitrogen they are attached to may also form a 5- to 7-membered non-aromatic heterocyclic ring optionally incorporating an additional ring heteroatom chosen from N, O, or S;

m is 1 or 2;

n is 0, 1 or 2; and p is 0, 1 or 2;

or pharmaceutically acceptable salts thereof.

34. A method of treating urinary incontinence, said method comprising administering to a subject in need of such treatment a safe and effective amount of a compound of the Formula I:

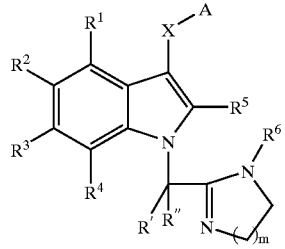

Formula I wherein:

X is $—S(O)_n—$ or $—C(O)—$;

A is $C_{1-6}$alkyl, aryl, heteroaryl, hydroxyalkyl, or $—(CH_2)_p—NR^aR^b$;

$R^1$, $R^2$, $R^3$, and $R^4$ each independently is hydrogen, halogen, haloalkyl, $C_{1-6}$alkyl, hydroxy, $C_{1-6}$alkoxy, $C_{1-6}$alkylthio, $C_{1-6}$alkylsulfinyl, $C_{1-6}$alkylsulfonyl, $C_{1-6}$alkylsulfonylamino, $C_{1-6}$alkylaminosulfonyl, cyano, nitro, $—NR^aR^b$, phenyl, benzyl or benzyloxy, wherein said phenyl, benzyl and benzyloxy are optionally substituted with $C_{1-6}$alkyl, halogen, cyano, nitro, haloalkyl, or $C_{1-6}$alkoxy;

$R^5$ is hydrogen, $C_{1-6}$alkyl, $C_{1-6}$alkoxy, $C_{1-6}$alkoxyalkyl, $C_{1-6}$alkylthio, $C_{1-6}$alkylsulfinyl, $C_{1-6}$alkylsulfonyl, hydroxyalkyl, hydroxyalkylamino, halogen, haloalkyl, cyano, $—NR^aR^b$, $—NR^c—C_{1-6}$alkyl-$NR^aR^b$, or $R^5$ and A together form a $C_2$–$C_3$ alkylene radical;

$R^6$ is hydrogen or $C_{1-6}$alkyl;

R' and R" each independently is hydrogen or alkyl;

$R^a$, $R^b$, and $R^c$ each independently is hydrogen, alkyl, hydroxyalkyl, alkoxyalkyl, aminoalkyl, haloalkyl, alkenyl, alkynyl, cycloalkyl, cycloalkylalkyl, alkylthioalkyl, heterocyclyl, heterocyclylalkyl, aryl, arylalkyl, heteroaryl, heteroarylalkyl, or arylsulfonyl, or $R^a$ and $R^b$ together with the nitrogen they are attached to may also form a 5- to 7-membered non-aromatic heterocyclic ring optionally incorporating an additional ring heteroatom chosen from N, O, or S;

m is 1 or 2;

n is 0, 1 or 2; and p is 0, 1 or 2;

or pharmaceutically acceptable salts thereof.

35. A method of treating nasal disorder, said method comprising administering to a mammal in need of such treatment a safe and effective amount of a compound of the Formula I:

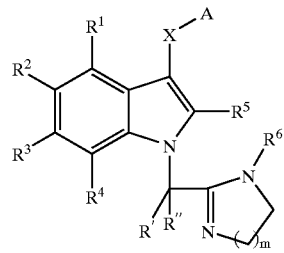

Formula I wherein:

X is $—S(O)_n—$ or $—C(O)$;

A is $C_{1-6}$alkyl, aryl, heteroaryl, hydroxyalkyl, or $—(CH_2)_p—NR^aR^b$;

$R^1$, $R^2$, $R^3$, and $R^4$ each independently is hydrogen, halogen, haloalkyl, $C_{1-6}$alkyl, hydroxy, $C_{1-6}$alkoxy, $C_{1-6}$alkylthio, $C_{1-6}$alkylsulfinyl, $C_{1-6}$alkylsulfonyl, $C_{1-6}$alkylsulfonylamino, $C_{1-6}$alkylaminosulfonyl, cyano, nitro, $—NR^aR^b$, phenyl, benzyl or benzyloxy, wherein said phenyl, benzyl and benzyloxy are optionally substituted with $C_{1-6}$alkyl, halogen, cyano, nitro, haloalkyl, or $C_{1-6}$alkoxy;

$R^5$ is hydrogen, $C_{1-6}$alkyl, $C_{1-6}$alkoxy, $C_{1-6}$alkoxyalkyl, $C_{1-6}$alkylthio, $C_{1-6}$alkylsulfinyl, $C_{1-6}$alkylsulfonyl, hydroxyalkyl, hydroxyalkylamino, halogen, haloalkyl, cyano, $—NR^aR^b$, $—NR^c—C_{1-6}$alkyl-$NR^aR^b$, or $R^5$ and A together form a $C_2$–$C_3$ alkylene radical;

$R^6$ is hydrogen or $C_{1-6}$alkyl;

R' and R" each independently is hydrogen or alkyl;

$R^a$, $R^b$, and $R^c$ each independently is hydrogen, alkyl, hydroxyalkyl, alkoxyalkyl, aminoalkyl, haloalkyl, alkenyl, alkynyl, cycloalkyl, cycloalkylalkyl, alkylthioalkyl, heterocyclyl, heterocyclylalkyl, aryl, arylalkyl, heteroaryl, heteroarylalkyl, or arylsulfonyl, or $R^a$ and $R^b$ together with the nitrogen they are attached to may also form a 5- to 7-membered non-aromatic heterocyclic ring optionally incorporating an additional ring heteroatom chosen from N, O, or S;

m is 1 or 2;

n is 0, 1 or 2; and p is 0, 1 or 2;

or pharmaceutically acceptable salts thereof.

36. The method of claim 33, wherein the disorder is stress incontinence.

37. The method of claim 33, wherein the disorder is urge incontinence.

38. The method of claim 35, wherein the disorder is nasal congestion.

39. The method of claim 35, wherein the disorder is sinusitis or otitis.

40. A process for preparing a compound as claimed in claim 1 which comprises reacting a compound having a Formula f:

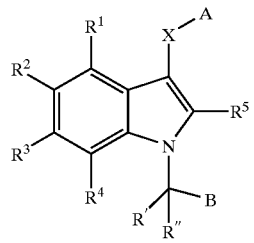
Formula f
wherein B is a cyano or a carboxylic acid or ester group, and $R^1$, $R^2$, $R^3$, $R^4$, $R^5$, $R^6$, R', R", n, X and A are as defined in claim 1,
with an appropriate alkylene diamine to provide a compound of the Formula
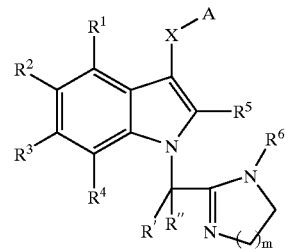
Formula I
wherein $R^1$, $R^2$, $R^3$, $R^4$, $R^5$, $R^6$, R', R", n, m, X and A are as defined in claim 1.
* * * * *

UNITED STATES PATENT AND TRADEMARK OFFICE
CERTIFICATE OF CORRECTION

PATENT NO.   : 6,852,726 B2
DATED        : February 8, 2005
INVENTOR(S)  : Robert Greenhouse et al.

It is certified that error appears in the above-identified patent and that said Letters Patent is hereby corrected as shown below:

Column 130,
Line 17, "or –C(O);" should read -- or –C(O)-; --;

Column 131,
Line 25, "wherein X is –C(O)." should read -- wherein X is –C(O)-. --;

Column 134,
Line 17, "or –C(O);" should read -- or –C(O)-; --.

Signed and Sealed this

Thirteenth Day of September, 2005

JON W. DUDAS
*Director of the United States Patent and Trademark Office*